United States Patent
Jang et al.

(10) Patent No.: US 10,205,103 B2
(45) Date of Patent: Feb. 12, 2019

(54) CONDENSED CYCLIC COMPOUND AND ORGANIC LIGHT-EMITTING DEVICE INCLUDING THE SAME

(71) Applicant: SAMSUNG DISPLAY CO., LTD., Yongin-si, Gyeonggi-do (KR)

(72) Inventors: Hyungseok Jang, Yongin-si (KR); Youngkook Kim, Yongin-si (KR); Jongwoo Kim, Yongin-si (KR); Jino Lim, Yongin-si (KR); Seokhwan Hwang, Yongin-si (KR)

(73) Assignee: SAMSUNG DISPLAY CO., LTD., Yongin-si, Gyeonggi-do (KR)

( * ) Notice: Subject to any disclaimer, the term of this patent is extended or adjusted under 35 U.S.C. 154(b) by 149 days.

(21) Appl. No.: 14/970,016

(22) Filed: Dec. 15, 2015

(65) Prior Publication Data

US 2016/0240790 A1 Aug. 18, 2016

(30) Foreign Application Priority Data

Feb. 13, 2015 (KR) .................. 10-2015-0022715

(51) Int. Cl.

| H01L 51/00 | (2006.01) |
| C07D 311/78 | (2006.01) |
| C07D 405/12 | (2006.01) |
| C07D 407/14 | (2006.01) |
| C07D 407/12 | (2006.01) |
| H01L 51/50 | (2006.01) |

(52) U.S. Cl.
CPC ........ H01L 51/0061 (2013.01); C07D 311/78 (2013.01); C07D 405/12 (2013.01); C07D 407/12 (2013.01); C07D 407/14 (2013.01); H01L 51/006 (2013.01); H01L 51/0073 (2013.01); H01L 51/0081 (2013.01); H01L 51/5056 (2013.01)

(58) Field of Classification Search
CPC ... C07D 311/78; C07D 407/12; C07D 407/14
See application file for complete search history.

(56) References Cited

U.S. PATENT DOCUMENTS

| 6,465,115 | B2 | 10/2002 | Shi et al. | |
| 6,596,415 | B2 | 7/2003 | Shi et al. | |
| 9,425,416 | B2 * | 8/2016 | Jung | H01L 51/0094 |
| 9,842,995 | B2 * | 12/2017 | Jung | H01L 51/0061 |
| 2009/0004485 | A1 | 1/2009 | Zheng et al. | |
| 2013/0001527 | A1 * | 1/2013 | Han | C07D 401/14 257/40 |
| 2013/0002527 | A1 * | 1/2013 | Kim | H01L 27/3272 345/82 |
| 2013/0202782 | A1 * | 8/2013 | Mandlik | H05B 33/10 427/66 |
| 2013/0306958 | A1 | 11/2013 | Ito et al. | |
| 2014/0248561 | A1 | 9/2014 | Echigo et al. | |
| 2014/0361266 | A1 * | 12/2014 | Jung | H01L 51/0094 257/40 |
| 2016/0233428 | A1 * | 8/2016 | Kim | H01L 51/0061 |
| 2017/0028378 | A1 * | 2/2017 | Hamers | B01J 19/121 |
| 2017/0062720 | A1 * | 3/2017 | Kim | H01L 51/0072 |
| 2017/0092869 | A1 * | 3/2017 | Mun | H01L 51/0061 |

FOREIGN PATENT DOCUMENTS

| JP | 2007-123863 A | | 5/2007 |
| JP | 2014-141414 | * | 8/2014 |
| JP | 2014-141414 A | | 8/2014 |
| JP | 2014-141416 A | | 8/2014 |
| KR | 10-2014-0032948 A | | 3/2014 |
| WO | WO 2012/157474 A1 | | 11/2012 |
| WO | WO 2013/024779 A1 | | 2/2013 |
| WO | WO 2015/178585 | * | 11/2015 |

OTHER PUBLICATIONS

Machine translation of JP 2014-141414, published on Aug. 7, 2014.*
Kumar, Sen-Gupta, Hemendra, "Condensation of Ketones with Phenols. Part I. Condensation with a-Naphthol", Journal of the Chemical Society, Transcations, 1914, 399.

* cited by examiner

*Primary Examiner* — Anca Eoff
(74) *Attorney, Agent, or Firm* — Lee & Morse, P.C.

(57) ABSTRACT

A condensed cyclic compound and an organic light-emitting device, the condensed cyclic compound being represented by the following Formula 1:

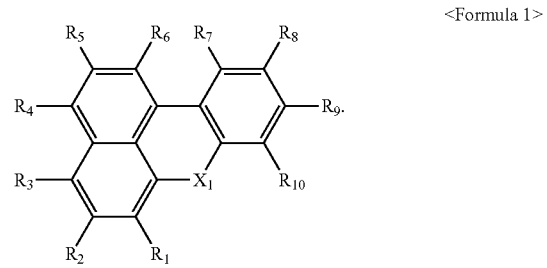

<Formula 1>

17 Claims, 1 Drawing Sheet

10

| 190 |
| 150 |
| 110 |

CONDENSED CYCLIC COMPOUND AND ORGANIC LIGHT-EMITTING DEVICE INCLUDING THE SAME

CROSS-REFERENCE TO RELATED APPLICATION

Korean Patent Application No. 10-2015-0022715, filed on Feb. 13, 2015, in the Korean Intellectual Property Office, and entitled: "Condensed Cyclic Compound and Organic Light-Emitting Device Including the Same," is incorporated by reference herein in its entirety.

BACKGROUND

1. Field

Embodiments relate to a condensed cyclic compound and an organic light-emitting device including the same.

2. Description of the Related Art

Organic light emitting devices are self-emission devices that have wide viewing angles, high contrast ratios, short response times, and excellent brightness, driving voltage, and response speed characteristics, and produce full-color images.

The organic light-emitting device may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, may be recombined in the emission layer to produce excitons. These excitons may change from an excited state to a ground state, thereby generating light.

SUMMARY

Embodiments are directed to a condensed cyclic compound and an organic light-emitting device including the same.

One or more exemplary embodiments include a condensed cyclic compound represented by Formula 1:

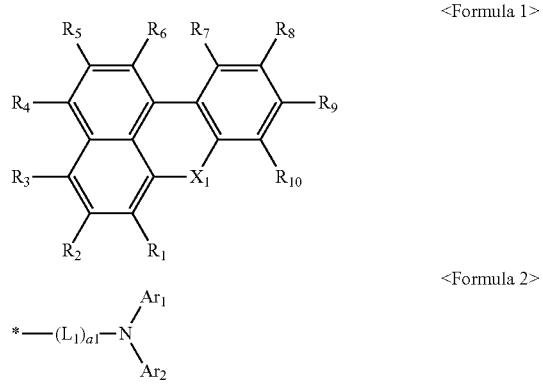

<Formula 1>

<Formula 2> wherein in Formulae 1 and 2, $X_1$ may be selected from an oxygen atom (O) and a sulfur atom (S);

each $L_1$ may independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a1 may be an integer selected from 0 to 3, and when a1 is two or more, a plurality of $L_1$ may be identical or different, $Ar_1$ and $Ar_2$ may each independently be selected from a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group and a substituted or unsubstituted monovalent non-aromatic condensed heteropolycyclic group;

$R_1$ to $R_{10}$ may each independently be selected from a group represented by Formula 2, a hydrogen, a deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$); and one selected from $R_1$ to $R_{10}$ may be a group represented by Formula 2, wherein at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{11}$)($Q_{12}$)($Q_{13}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{21}$)($Q_{22}$)($Q_{23}$); and —Si($Q_{31}$)($Q_{32}$)($Q_{33}$);

wherein $Q_1$ to $Q_3$, $Q_{11}$ to $Q_{13}$, $Q_{21}$ to $Q_{23}$, and $Q_{31}$ to $Q_{33}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

One or more exemplary embodiments include an organic light-emitting device including a first electrode; a second electrode facing the first electrode; and an organic layer between the first electrode and the second electrode, the organic layer including an emission layer, wherein the organic layer comprises at least one of the condensed cyclic compounds.

BRIEF DESCRIPTION OF THE DRAWING

Features will be apparent to those of skill in the art by describing in detail exemplary embodiments with reference to the attached drawing in which:

FIG. 1 illustrates a schematic view of an organic light-emitting device according to an exemplary embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURE, the dimensions of layers and regions may be exaggerated for clarity of illustration. Like reference numerals refer to like elements throughout.

A condensed cyclic compound according to an exemplary embodiment may represented by Formula 1, below.

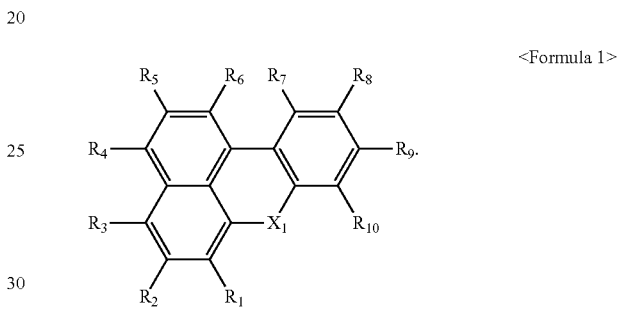

<Formula 1>

$X_1$ in Formula 1 may be, e.g., an oxygen atom (O) or a sulfur atom (S). In an implementation, $X_1$ may be O.

$R_1$ to $R_{10}$ in Formula 1 may each independently be selected from or include, e.g., a group represented by Formula 2, a hydrogen, a deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$).

One selected from $R_1$ to $R_{10}$ in Formula 1 may be a group represented by the following Formula 2.

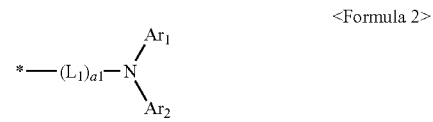

<Formula 2>

In Formula 2, each $L_1$ may independently be selected from or include, e.g., a substituted or unsubstituted $C_3$-$C_{10}$ cycloalkylene group, a substituted or unsubstituted C₁-C₁₀ heterocycloalkylene group, a substituted or unsubstituted C₃-C₁₀ cycloalkenylene group, a substituted or unsubstituted C₁-C₁₀ heterocycloalkenylene group, a substituted or unsubstituted C₆-C₆₀ arylene group, a substituted or unsubstituted C₁-C₆₀ heteroarylene group, a substituted or unsubstituted divalent non-aromatic condensed polycyclic group, and a substituted or unsubstituted divalent non-aromatic condensed heteropolycyclic group.

For example, each L₁ in Formula 2 may independently be selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group and an imidazopyrimidinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C₁-C₂₀ alkyl group, a C₁-C₂₀ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

In an implementation, each L₁ in Formula 2 may independently be a group represented by one of the following Formulae 3-1 to 3-35.

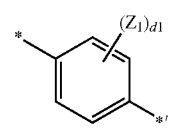

Formula 3-1

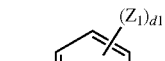

Formula 3-2

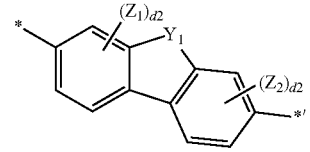

Formula 3-3

-continued
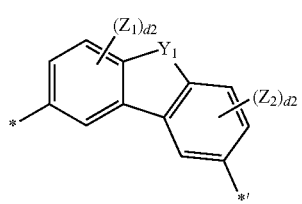
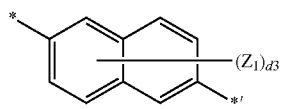
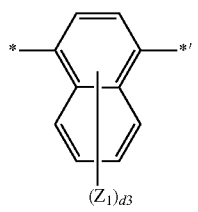
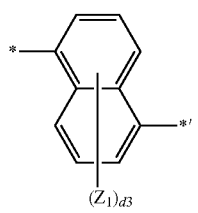
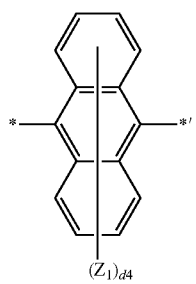
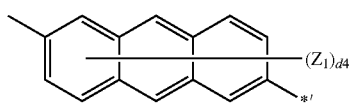
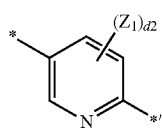
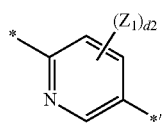
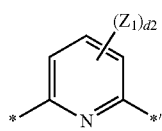
-continued
Formula 3-4
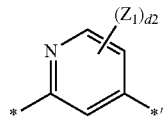
Formula 3-5
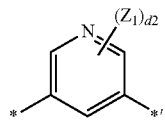
Formula 3-6
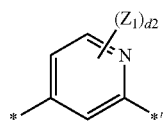
Formula 3-7

Formula 3-8
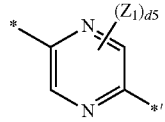
Formula 3-9
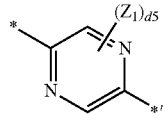
Formula 3-10
Formula 3-11
Formula 3-12
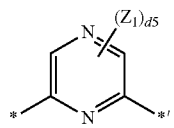
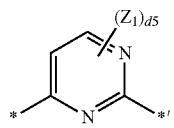
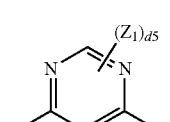
Formula 3-13
Formula 3-14
Formula 3-15
Formula 3-16
Formula 3-17
Formula 3-18
Formula 3-19
Formula 3-20
Formula 3-21
Formula 3-22
Formula 3-23
Formula 3-24

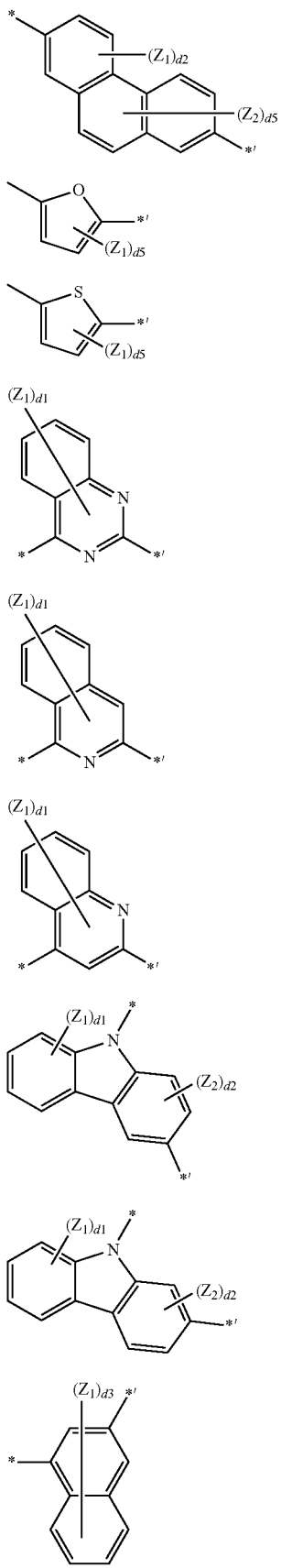

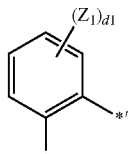

Formula 3-25

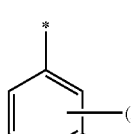

Formula 3-34

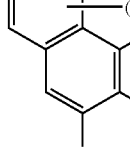

Formula 3-35

Formula 3-26

Formula 3-27

Formula 3-28

Formula 3-29

Formula 3-30

Formula 3-31

Formula 3-32

Formula 3-33

In Formulae 3-1 to 3-35, $Y_1$ may be, e.g., O, S, $C(Z_3)(Z_4)$, $N(Z_5)$, or $Si(Z_6)(Z_7)$;

$Z_1$ to $Z_7$ may each independently be selected from or include, e.g., a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, d1 may be an integer selected from 1 to 4, d2 may be an integer selected from 1 to 3, d3 may be an integer selected from 1 to 6, d4 may be an integer selected from 1 to 8, d5 may be 1 or 2, d6 may be an integer selected from 1 to 5, * and *' each indicate a binding site to a neighboring atom.

In an implementation, each $L_1$ in Formula 2 may independently be selected from:

a phenylene group, a naphthylene group, a pyridinylene group, a dibenzofuranylene group, and a dibenzothiophenylene group; and a phenylene group, a naphthylene group, a pyridinylene group, a dibenzofuranylene group, and a dibenzothiophenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a phenyl group, a naphthyl group, a pyridinyl group, a pyrimidinyl group, and a triazinyl group.

In an implementation, each $L_1$ in Formula 2 may independently be a group represented by one of the following Formulae 4-1 to 4-29.

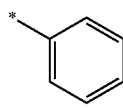

Formula 4-1

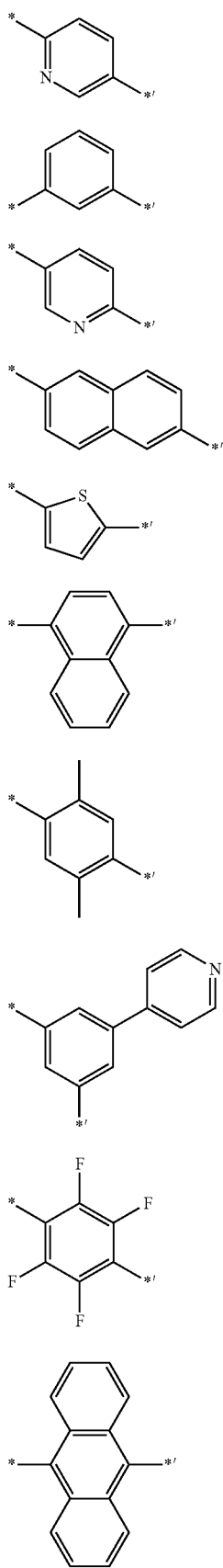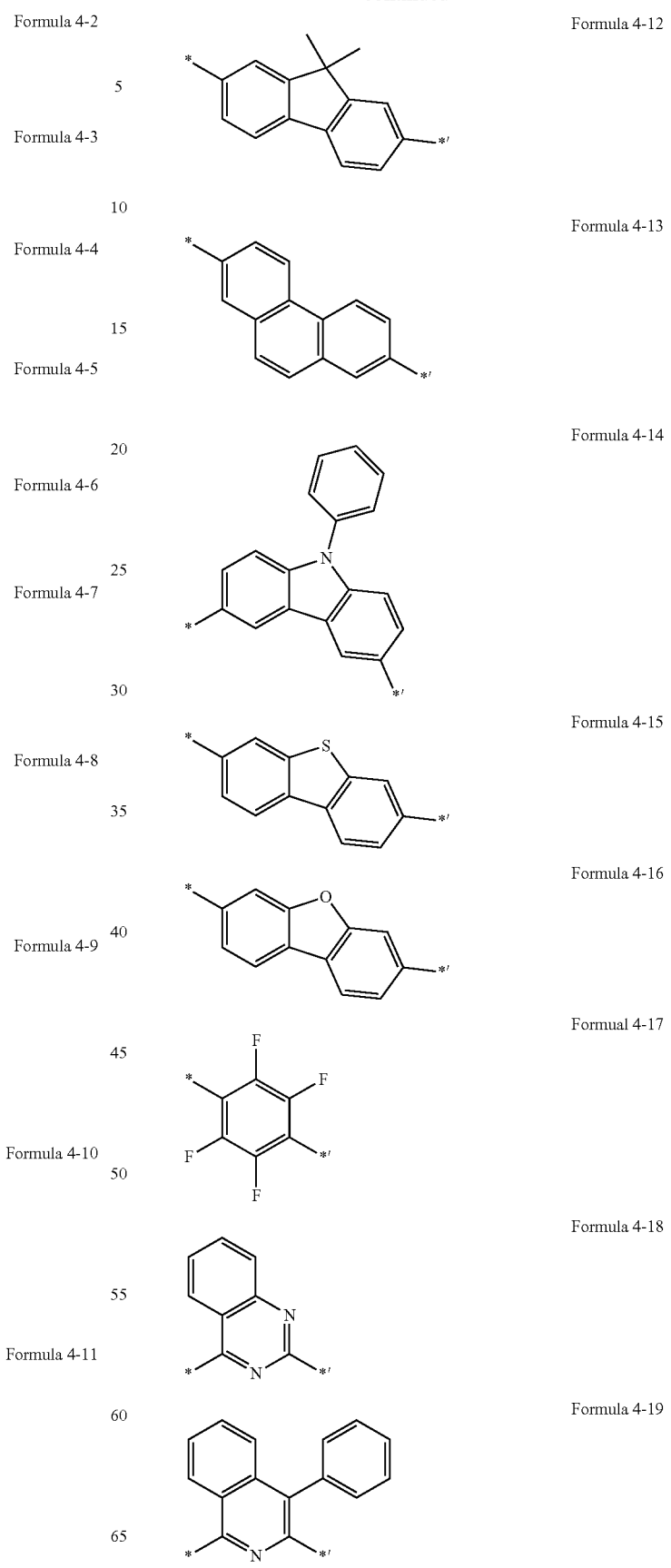

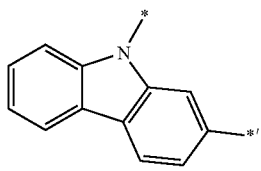

Formula 4-20

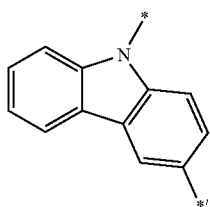

Formula 4-21

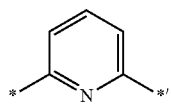

Formula 4-22

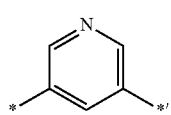

Formula 4-23

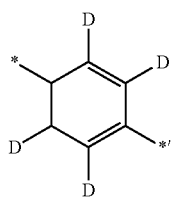

Formula 4-24

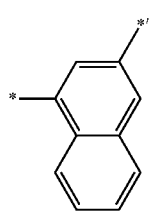

Formula 4-25

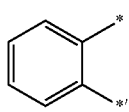

Formula 4-26

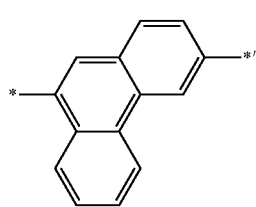

Formula 4-27

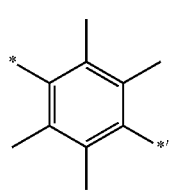

Formula 4-28

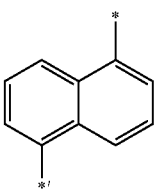

Formula 4-29

In Formulae 4-1 to 4-29, * and *' each indicate a binding site to a neighboring atom.

a1 in Formula 2 may be an integer selected from, e.g., 0 to 3. a1 indicates the number of $L_1$ in Formula 2, and when a1 is two or more, a plurality of $L_1$ may be identical or different. For example, when a1 is 0, *-$(L_1)_{a1}$-*' is a single bond. In an implementation, a1 may be, e.g., 0, 1, or 2. In an implementation, a1 may be, e.g., 0 or 1.

$Ar_1$ and $Ar_2$ in Formula 2 may each independently be selected from or include, e.g., a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, $Ar_1$ and $Ar_2$ in Formula 2 may each independently be selected from or include:

a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted spiro-fluorenyl group, a substituted or unsubstituted benzofluorenyl group, a substituted or unsubstituted dibenzofluorenyl group, a substituted or unsubstituted phenalenyl group, a substituted or unsubstituted phenanthrenyl group, a substituted or unsubstituted anthracenyl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pentacenyl group, a substituted or unsubstituted rubicenyl group, a substituted or unsubstituted coronenyl group, a substituted or unsubstituted ovalenyl group, a substituted or unsubstituted pyrrolyl group, a substituted or unsubstituted thiophenyl group, a substituted or unsubstituted furanyl group, a substituted or unsubstituted imidazolyl group, a substituted or unsubstituted pyrazolyl group, a substituted or unsubstituted thiazolyl group, a substituted or unsubstituted isothiazolyl group, a substituted or unsubstituted oxazolyl group, a substituted or unsubstituted isoxazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted isoquinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzoimidazolyl group, a substituted or unsubstituted benzofuranyl group, a substituted or unsubstituted benzothiophenyl group, a substituted or unsubstituted isobenzothiazolyl group, a substituted or unsubstituted benzoxazolyl group, a substituted or unsubstituted isobenzoxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted benzocarbazolyl group, a substituted or unsubstituted dibenzocarbazolyl group, a substituted or unsubstituted thiadiazolyl group, a substituted or unsubstituted imidazopyridinyl group, a substituted or unsubstituted imidazopyrimidinyl group, —Si($Q_1$)($Q_2$)($Q_3$), and —B($Q_4$)($Q_5$).

At least one substituent of the substituted phenyl group, substituted pentalenyl group, substituted indenyl group, substituted naphthyl group, substituted azulenyl group, substituted heptalenyl group, substituted indacenyl group, substituted group, substituted fluorenyl group, substituted spiro-fluorenyl group, substituted benzofluorenyl group, substituted dibenzofluorenyl group, substituted phenalenyl group, substituted phenanthrenyl group, substituted anthracenyl group, substituted fluoranthenyl group, substituted triphenylenyl group, substituted pyrenyl group, substituted chrysenyl group, substituted naphthacenyl group, substituted picenyl group, substituted perylenyl group, substituted pentaphenyl group, substituted hexacenyl group, substituted pentacenyl group, substituted rubicenyl group, substituted coronenyl group, substituted ovalenyl group, substituted pyrrolyl group, substituted thiophenyl group, substituted furanyl group, substituted imidazolyl group, substituted pyrazolyl group, substituted thiazolyl group, substituted isothiazolyl group, substituted oxazolyl group, substituted isoxazolyl group, substituted pyridinyl group, substituted pyrazinyl group, substituted pyrimidinyl group, substituted pyridazinyl group, substituted isoindolyl group, substituted indolyl group, substituted indazolyl group, substituted purinyl group, substituted quinolinyl group, substituted isoquinolinyl group, substituted benzoquinolinyl group, substituted phthalazinyl group, substituted naphthyridinyl group, substituted quinoxalinyl group, substituted quinazolinyl group, substituted cinnolinyl group, substituted carbazolyl group, substituted phenanthridinyl group, substituted acridinyl group, substituted phenanthrolinyl group, substituted phenazinyl group, substituted benzoimidazolyl group, substituted benzofuranyl group, substituted benzothiophenyl group, substituted isobenzothiazolyl group, substituted benzoxazolyl group, substituted isobenzoxazolyl group, substituted triazolyl group, substituted tetrazolyl group, substituted oxadiazolyl group, substituted triazinyl group, substituted benzocarbazolyl group, substituted dibenzocarbazolyl group, substituted thiadiazolyl group, substituted imidazopyridinyl group, and substituted imidazopyrimidinyl group may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof and a phosphoric acid or a salt thereof;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, and a dibenzocarbazolyl group;

a phenyl group, a naphthyl group, a pyridinyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, and a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and a pyridinyl group; and —Si($Q_{31}$)($Q_{32}$)($Q_{33}$), wherein $Q_{31}$ to $Q_{33}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, and a carbazolyl group.

In an implementation, $Ar_1$ and $Ar_2$ in Formula 2 may each independently be a group represented by one of the following Formulae 5-1 to 5-16.

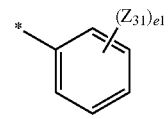

Formula 5-1

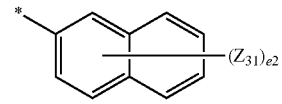

Formula 5-2

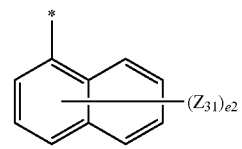

Formula 5-3

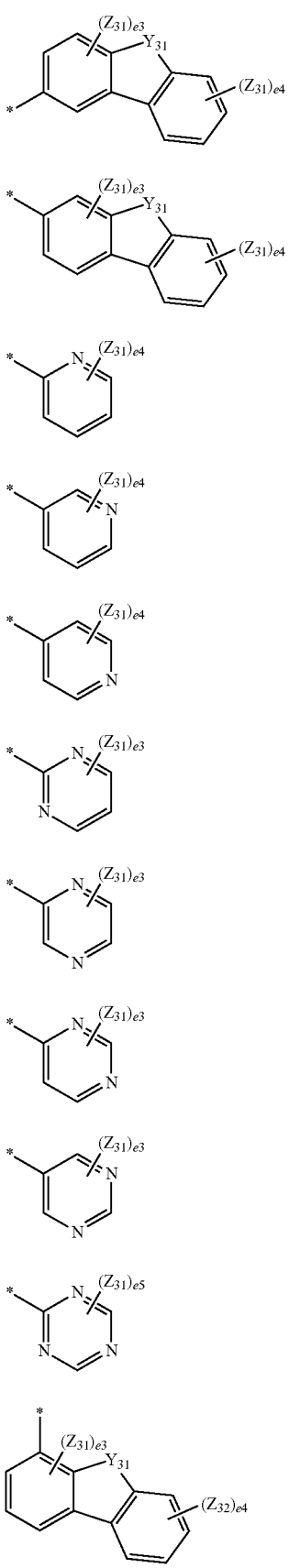

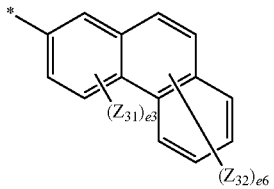

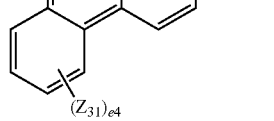

In Formulae 5-1 to 5-16, $Y_{31}$ may be, e.g., O, S, $C(Z_{33})(Z_{34})$, $N(Z_{35})$, or $Si(Z_{36})(Z_{37})$;

$Z_{31}$ to $Z_{37}$ may each independently be selected from, e.g., a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, and a dibenzocarbazolyl group;

a phenyl group, a naphthyl group, a pyridinyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, and a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and a pyridinyl group; and —$Si(Q_{31})(Q_{32})(Q_{33})$ $Q_{31}$ to $Q_{33}$ may each independently be selected from, e.g., a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, and a carbazolyl group.

e1 may be an integer selected from 1 to 5, e2 may be an integer selected from 1 to 7, e3 may be an integer selected from 1 to 3, e4 may be an integer selected from 1 to 4, e5 may be 1 or 2, e6 may be an integer selected from 1 to 6, and * indicates a binding site to a neighboring atom.

In an implementation, $Ar_1$ and $Ar_2$ in Formula 2 may each independently be a group represented by one of the following Formulae 6-1 to 6-35.

Formula 6-1
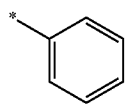

Formula 6-2
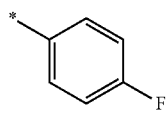

Formula 6-3
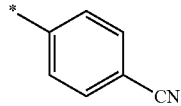

Formula 6-4
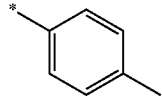

Formula 6-5
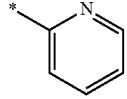

Formula 6-6
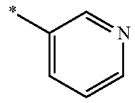

Formula 6-7
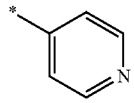

Formula 6-8
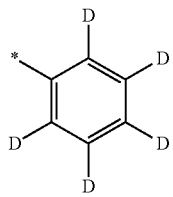

Formula 6-9
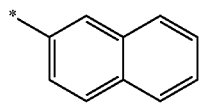

Formula 6-10
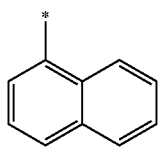

Formula 6-11
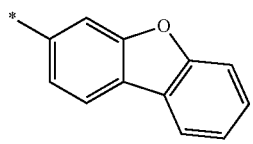

Formula 6-12
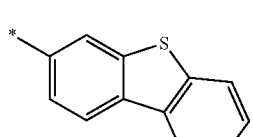

Formula 6-13
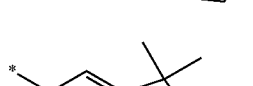

Formual 6-14
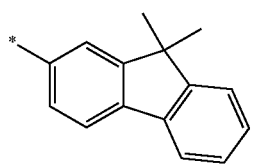

Formula 6-15
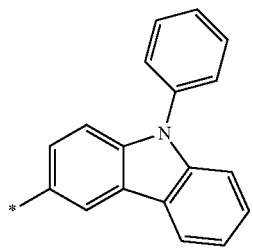

Formula 6-16
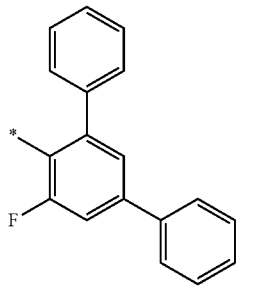

Formula 6-17
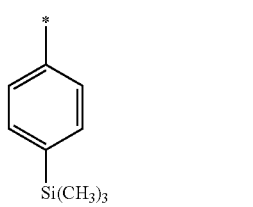

Formual 6-18
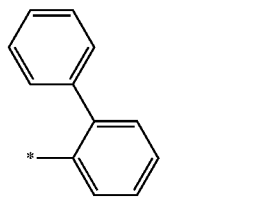

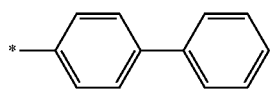

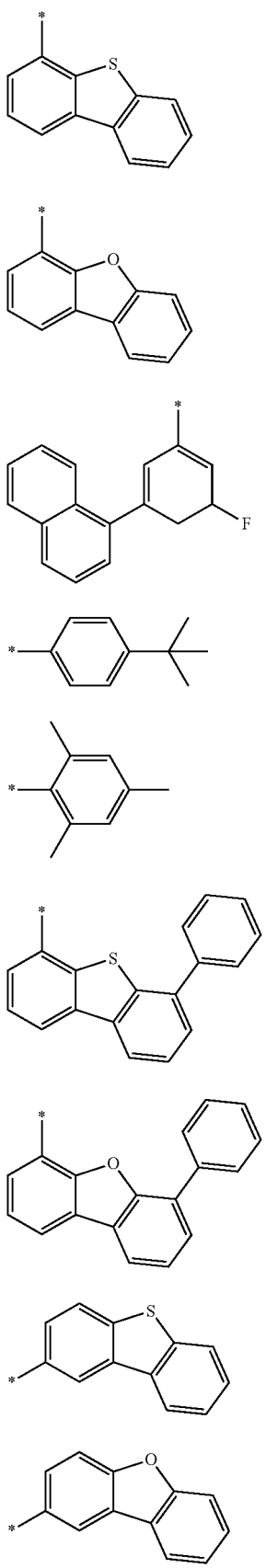
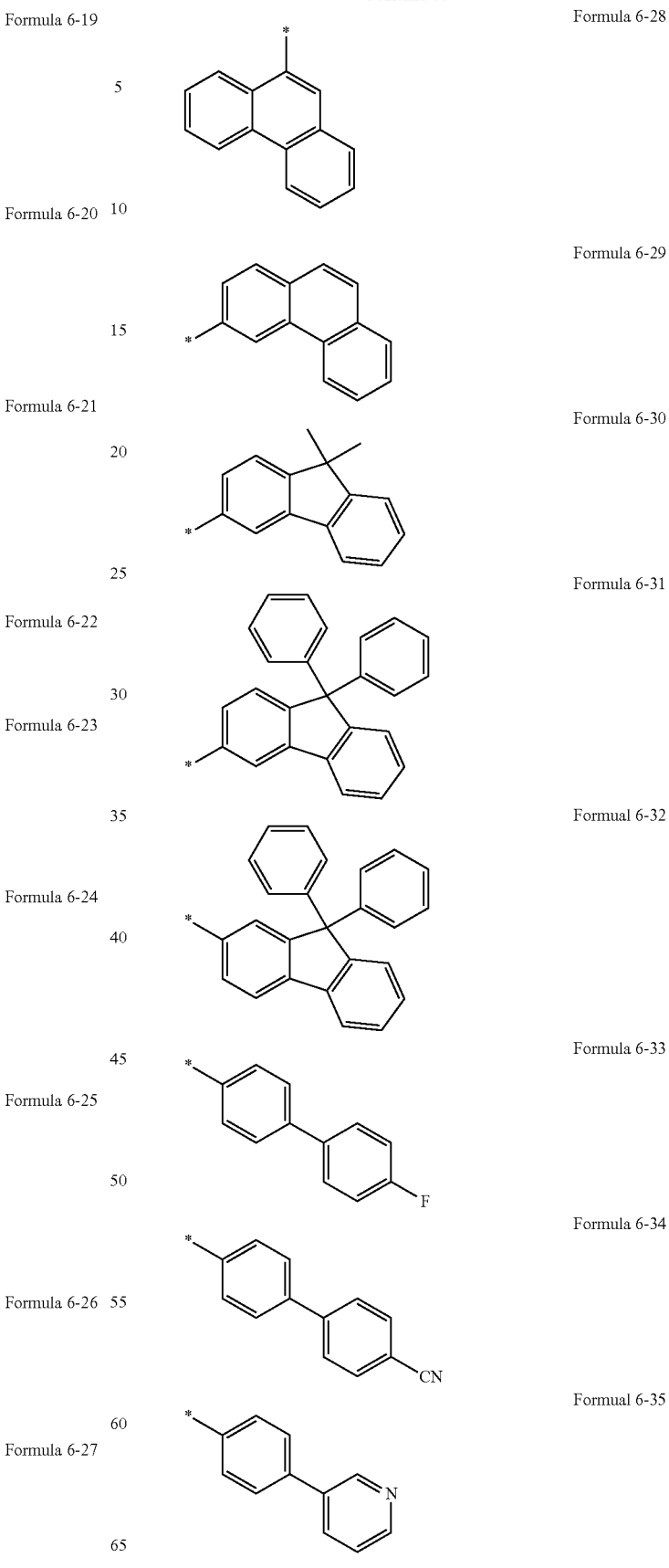

* in Formulae 6-1 to 6-35 indicates a binding site to a neighboring atom.

In an implementation, $R_1$ to $R_{10}$ in Formula 1 may each independently be selected from:

a group represented by Formula 2, a hydrogen, a deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, an imidazopyrimidinyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ may each independently be selected from a $C_1$-$C_{10}$ alkyl group, a $C_1$-$C_{10}$ alkoxy group, a phenyl group, and a naphthyl group.

In an implementation, $R_1$ to $R_{10}$ in Formula 1 may each independently be selected from:

a group represented by Formula 2, a hydrogen, a deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a phenyl group, a naphthyl group, a pyridinyl group, a pyrimidinyl group, and a triazinyl group;

a phenyl group, a naphthyl group, a pyridinyl group, a pyrimidinyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ may each independently be selected from a $C_1$-$C_{10}$ alkyl group, a $C_1$-$C_{10}$ alkoxy group, a phenyl group, and a naphthyl group.

One selected from $R_1$ to $R_{10}$ in Formula 1 may be the group represented by Formula 2. For example, one selected from $R_3$, $R_4$, and $R_9$ in Formula 1 may be the group represented by Formula 2.

In an implementation, the condensed cyclic compound represented by Formula 1 may be represented by one of the following Formulae 1-1 to 1-7.

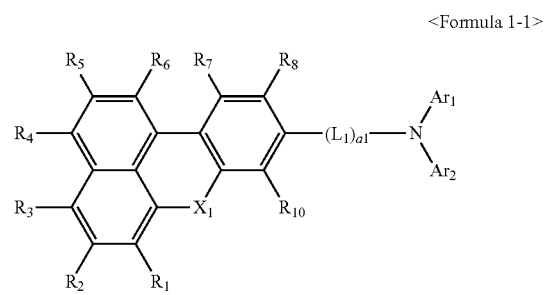

<Formula 1-1>

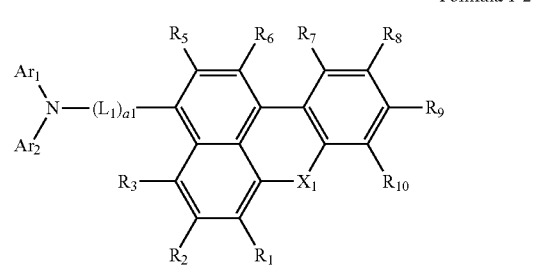

<Formula 1-2>

-continued

<Formula 1-3>
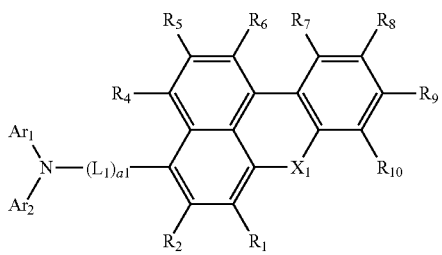

<Formula 1-4>
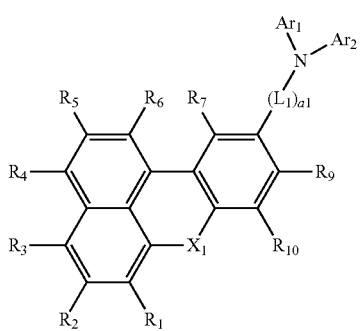

<Formula 1-5>
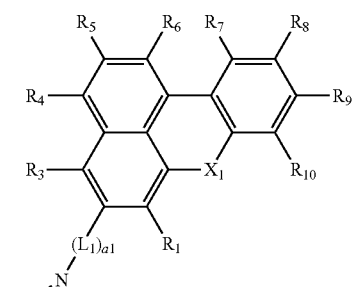

<Formula 1-6>
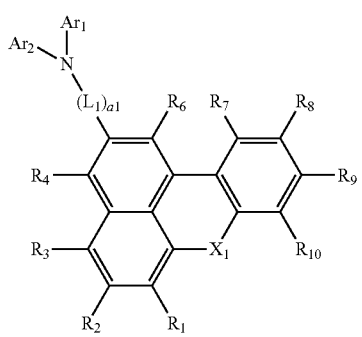

<Formula 1-7>
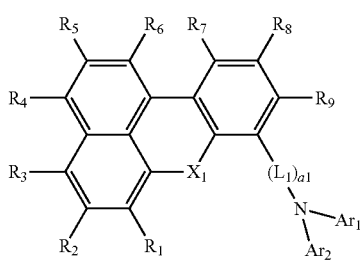

In Formulae 1-1 to 1-7, descriptions of $X_1$, $L_1$, a1, $Ar_1$, $Ar_2$, and $R_1$ to $R_{10}$ may be the same as described above.

In an implementation, a1 in Formulae 1-1 to 1-7 may be 0 or 1. In an implementation, in Formulae 1-1 to 1-7, $Ar_1=Ar_2$; or $Ar_1 \neq Ar_2$.

In an implementation, in Formulae 1-1 to 1-7, $R_1$ to $R_{10}$ may each independently be selected from, e.g., a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a pyridinyl group, a pyrimidinyl group, and a triazinyl group, each $L_1$ may independently be a group represented by one of Formula 3-1 to Formula 3-35, a1 may be 0, 1, or 2, and $Ar_1$ and $Ar_2$ may each independently be a group represented by one of Formulae 5-1 to 5-16.

In an implementation, in Formulae 1-1 to 1-7, $R_1$ to $R_{10}$ may each be a hydrogen, each $L_1$ may independently be a group represented by one of Formulae 4-1 to 4-29, a1 may be 0 or 1, and $Ar_1$ and $Ar_2$ may each independently be a group represented by one of Formulae 6-1 to 6-35.

In an implementation, the condensed cyclic compound represented by Formula 1 may be represented by one of the following Formulae 1-1(A), 1-1(B), 1-2(A), 1-2(B), 1-3(A), and 1-3(B).

<Formula 1-1(A)>
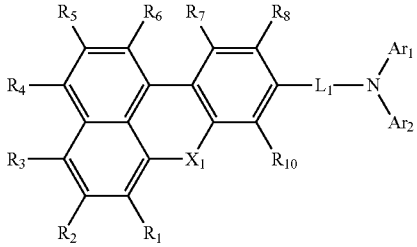

<Formula 1-1(B)>
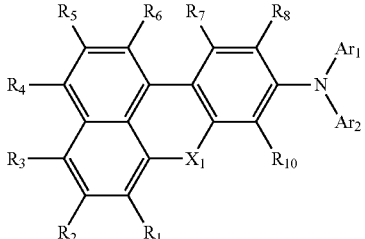

<Formula 1-2(A)>
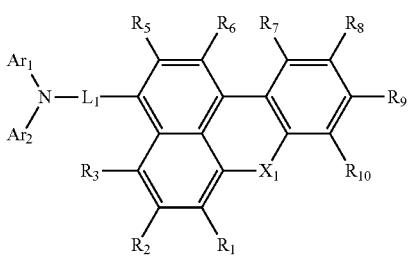

<Formula 1-2(B)>

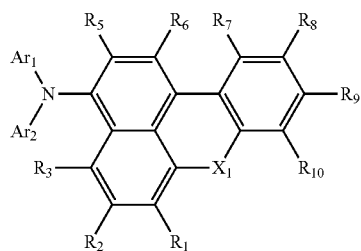

<Formula 1-3(A)>

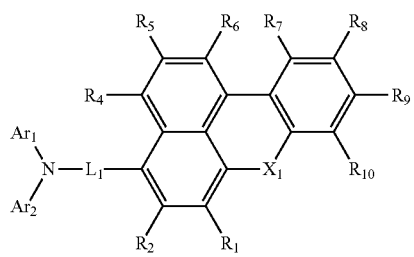

<Formula 1-3(B)>

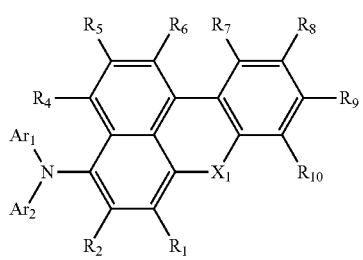

In Formulae 1-1(A), 1-1(B), 1-2(A), 1-2(B), 1-3(A), and 1-3(B), descriptions of $X_1$, $L_1$, $Ar_1$, $Ar_2$, and $R_1$ to $R_{10}$ may be the same as described above.

In an implementation, in the formulae above, $R_1$ to $R_{10}$ may each independently be selected from, e.g., a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a pyridinyl group, a pyrimidinyl group, and a triazinyl group, $L_1$ may be, e.g., a represented by one of Formula 3-1 to Formula 3-35, and $Ar_1$ and $Ar_2$ may each independently be, e.g., a group represented by one of Formulae 5-1 to 5-16.

In an implementation, in the Formulae above, $R_1$ to $R_{10}$ may be, e.g., a hydrogen, $L_1$ may be, e.g., a group represented by one of Formulae 4-1 to 4-29, $Ar_1$ and $Ar_2$ may each independently be, e.g., a group represented by one of Formulae 6-1 to 6-35.

In an implementation, the condensed cyclic compound represented by Formula 1 may be one of the following Compounds 1 to 102.

1

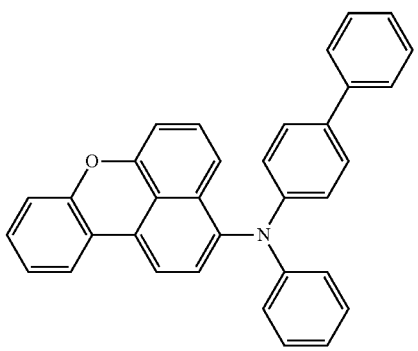

2

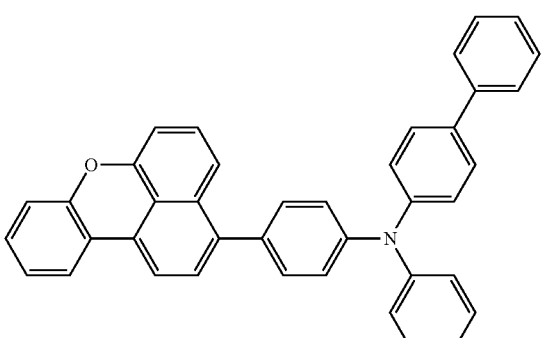

3

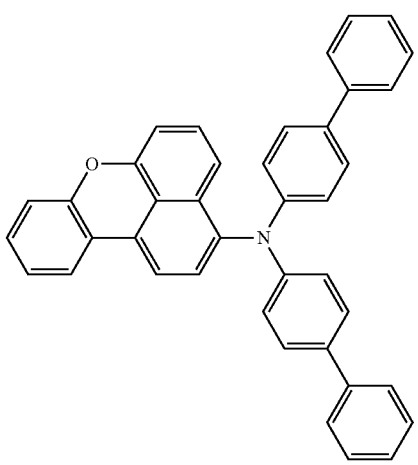

4

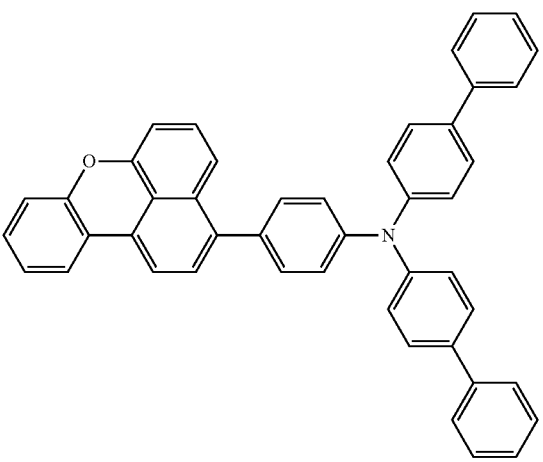

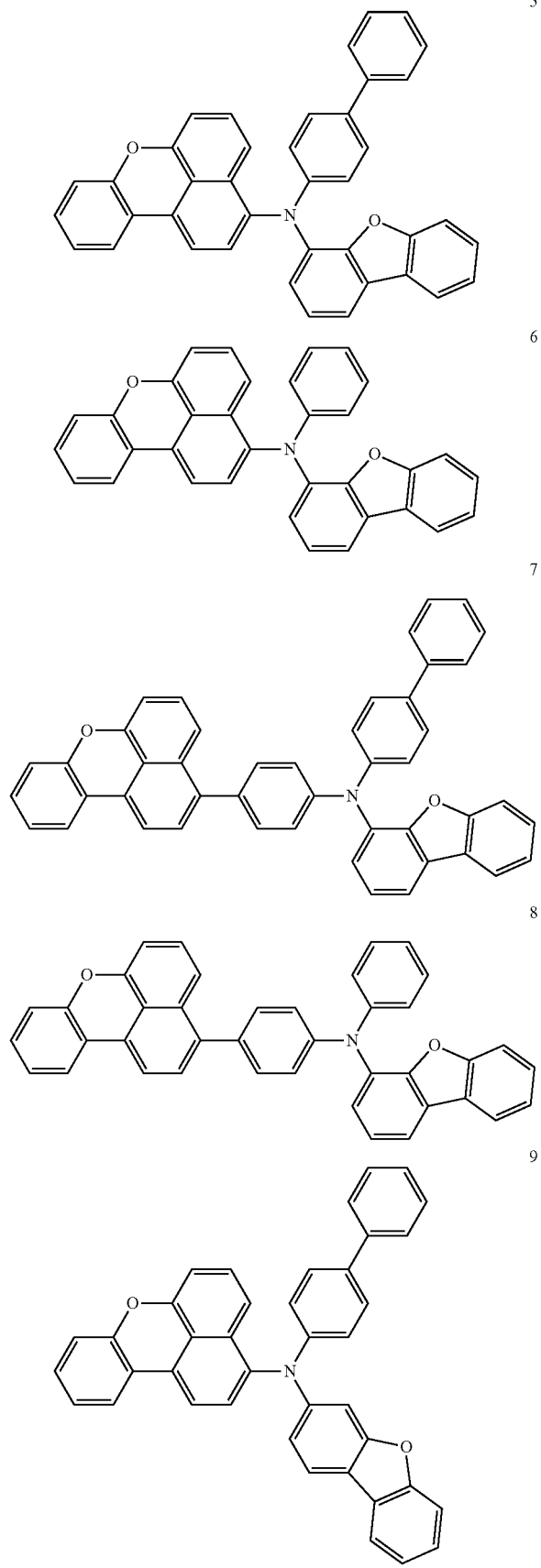
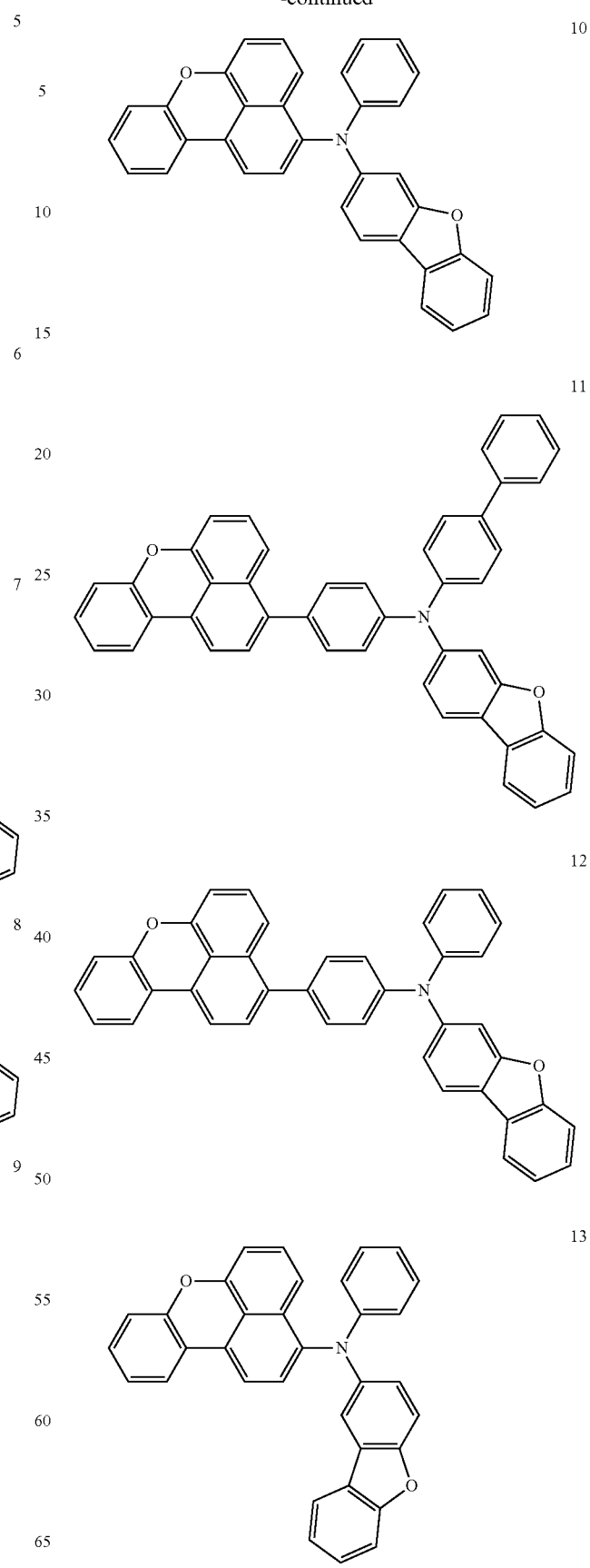

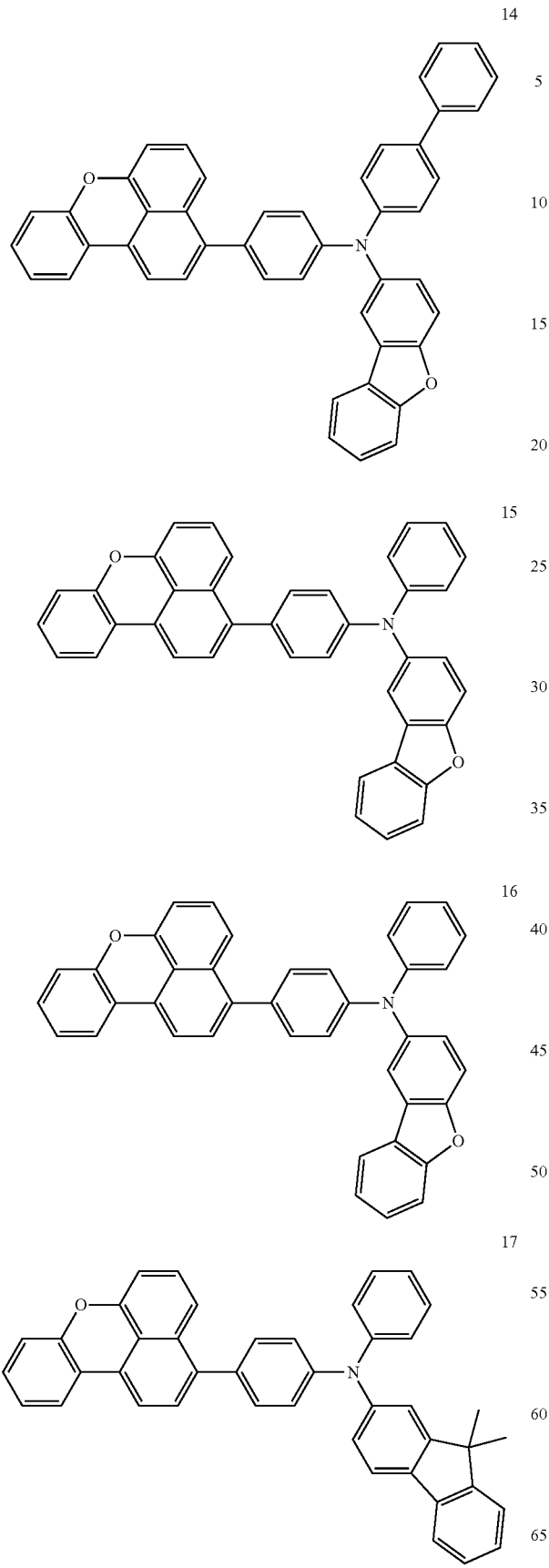
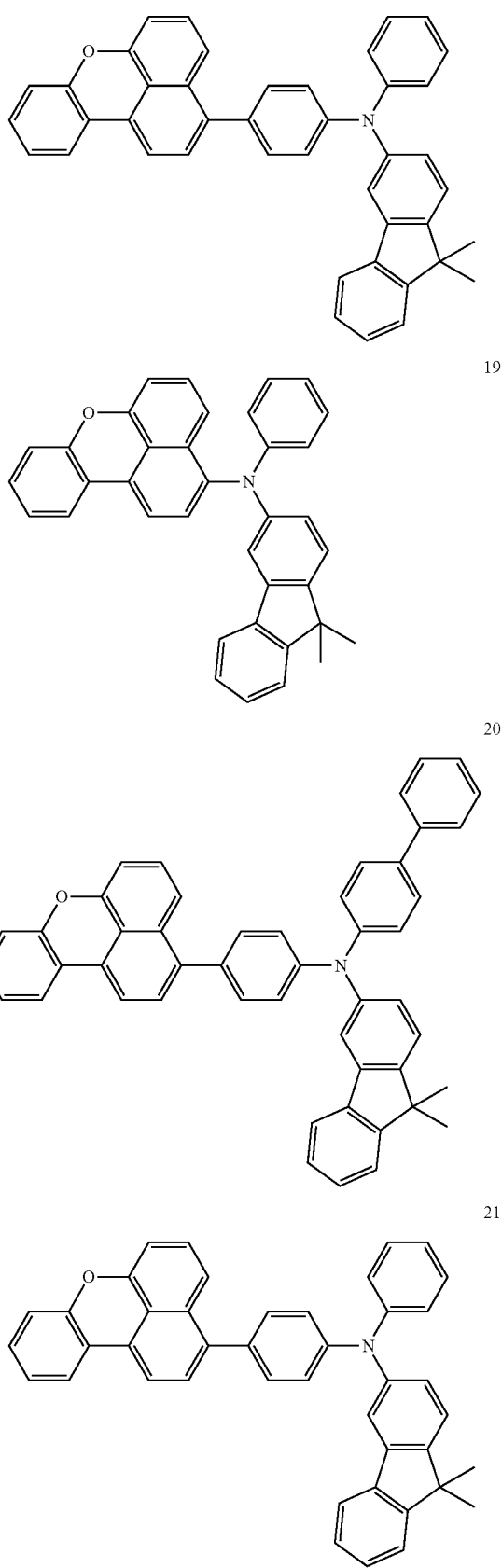

22
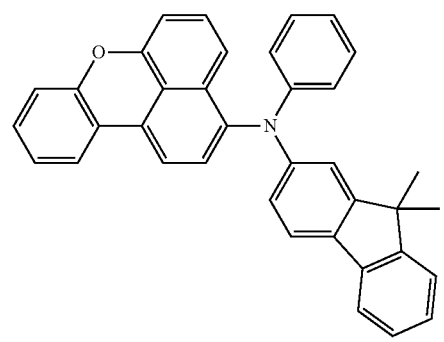
23
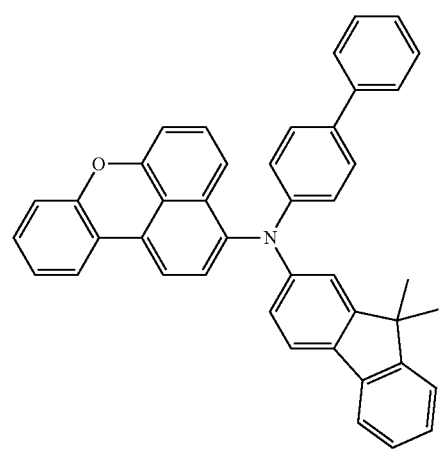
24
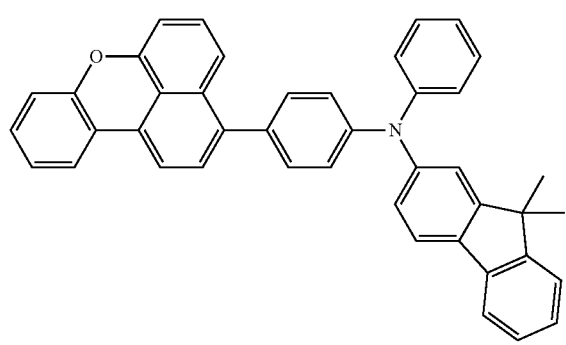
25
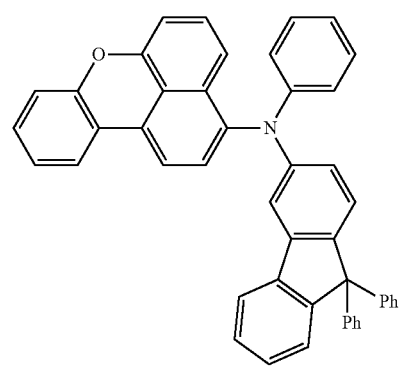
26
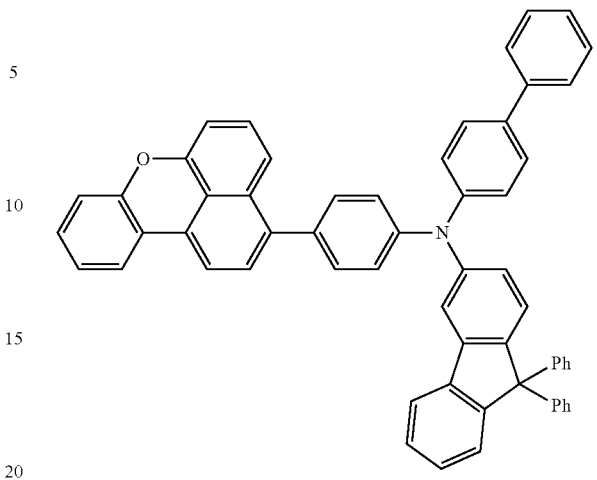
27
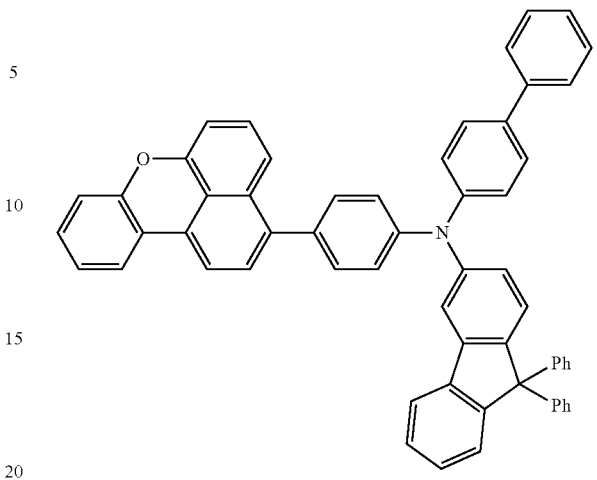
28
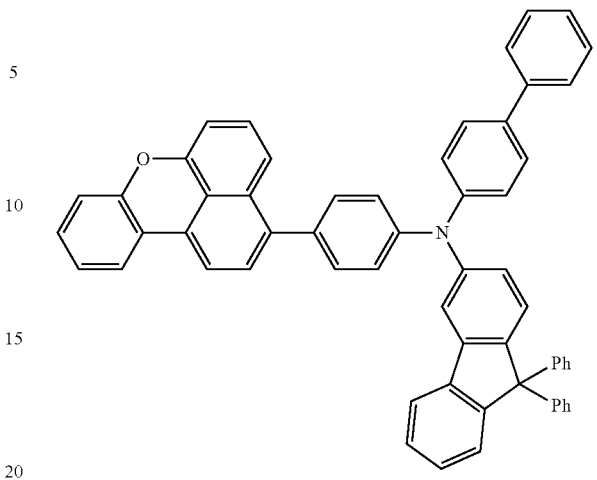
29
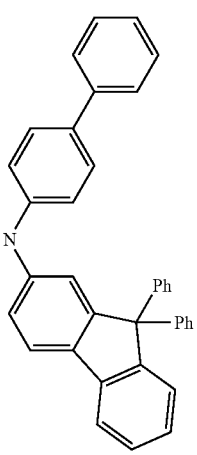

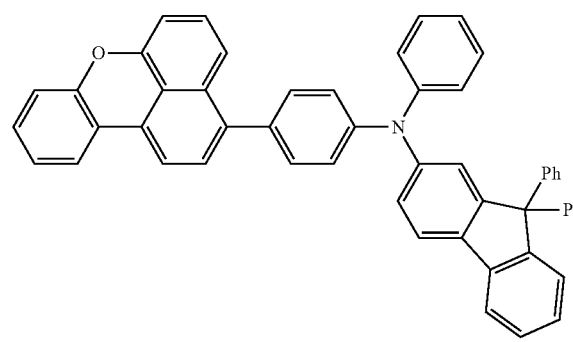
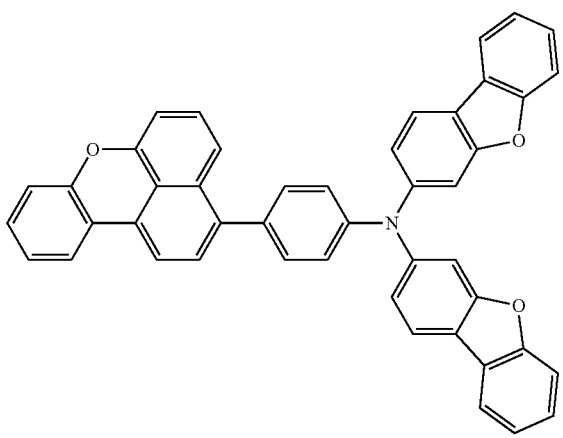
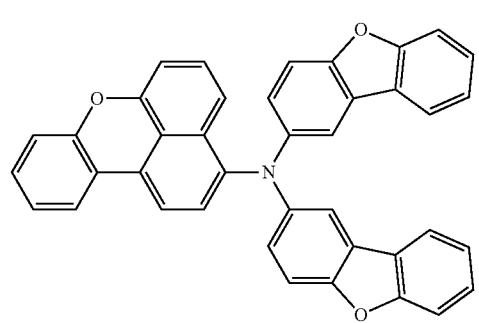
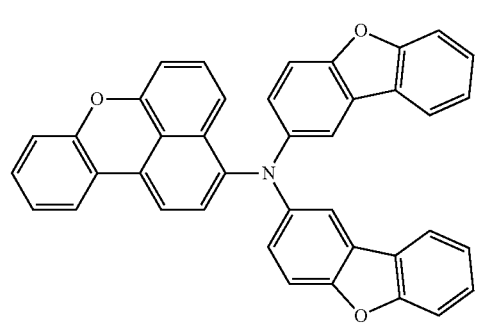
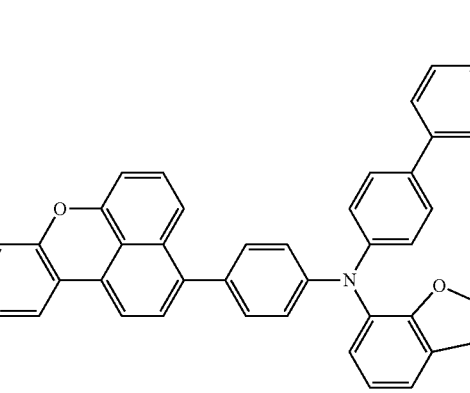

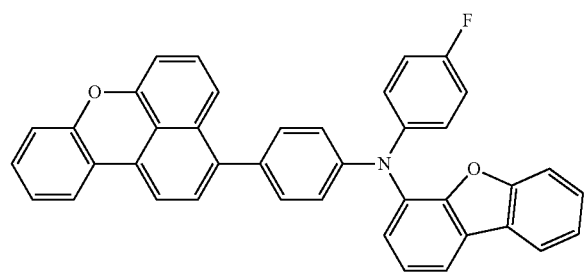
38
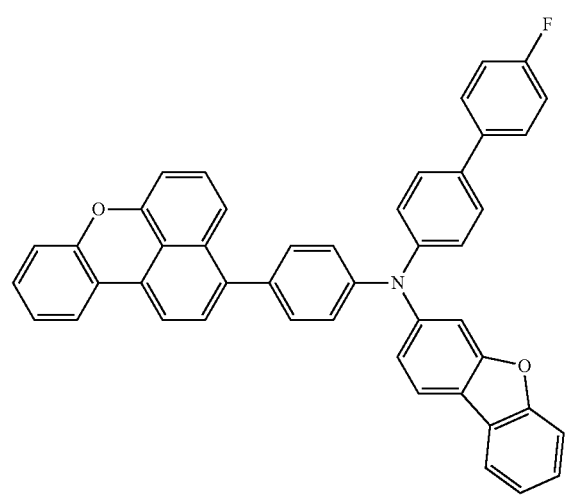
39
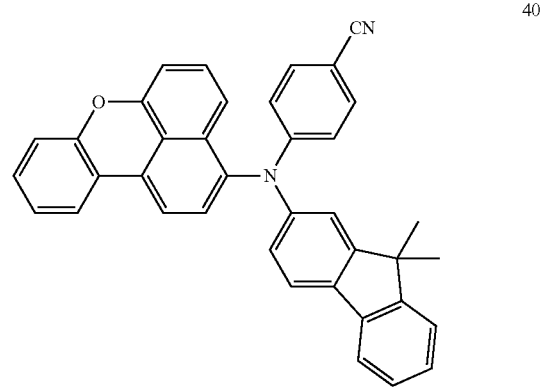
40
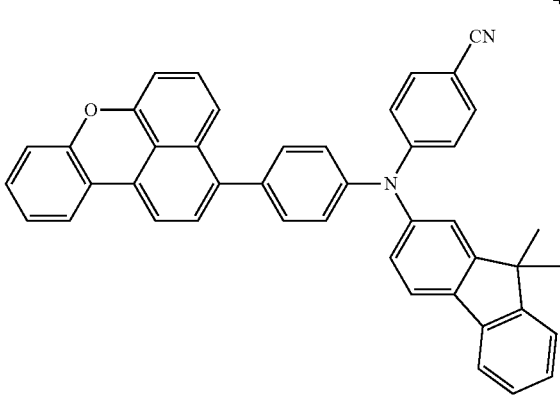
42
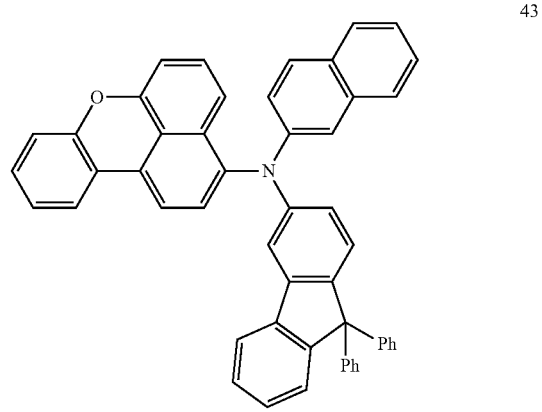
43
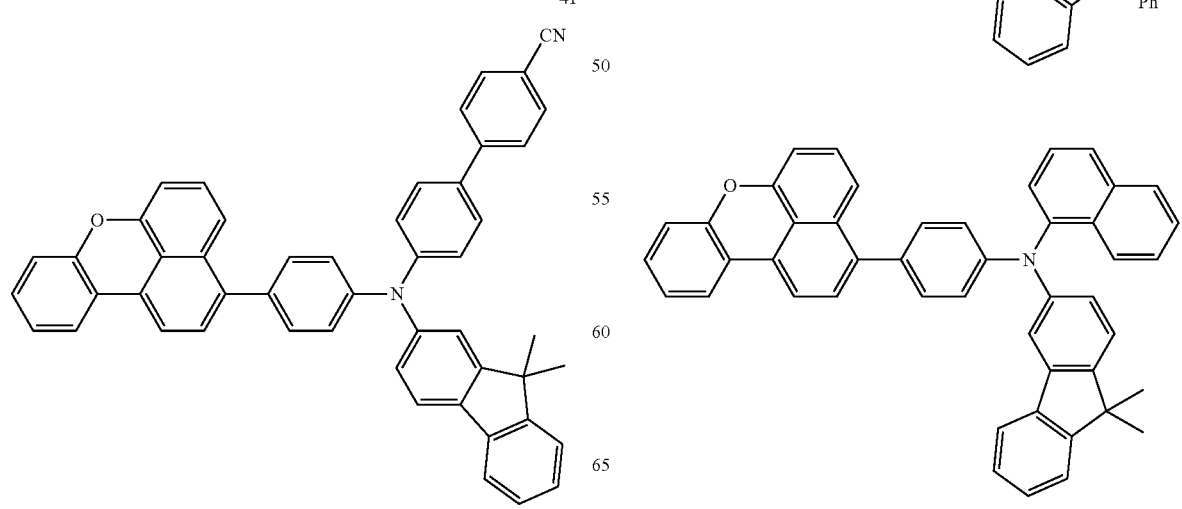

46
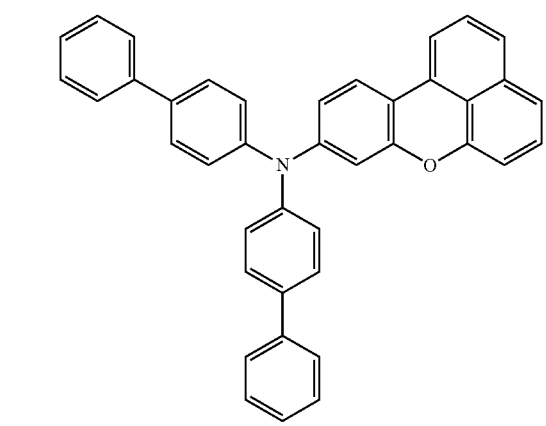
47
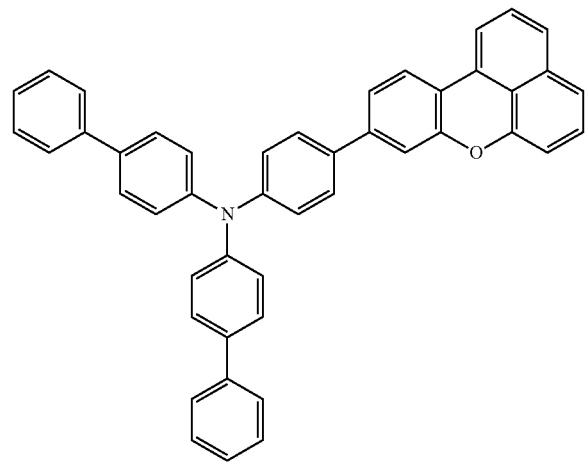
48
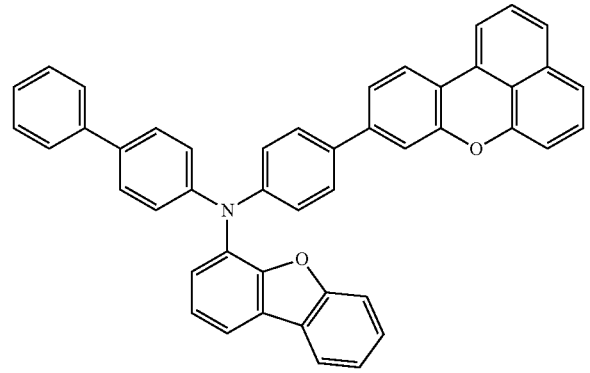
49
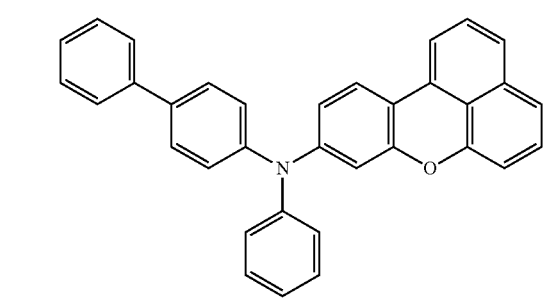
50
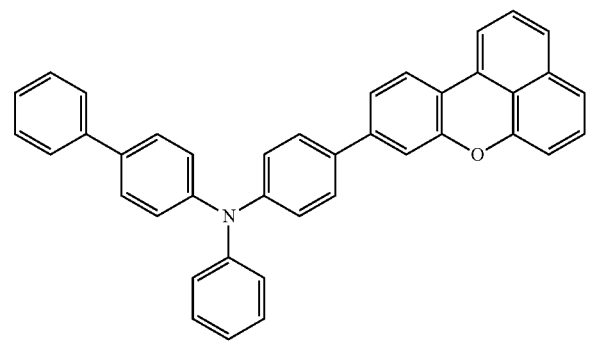
51
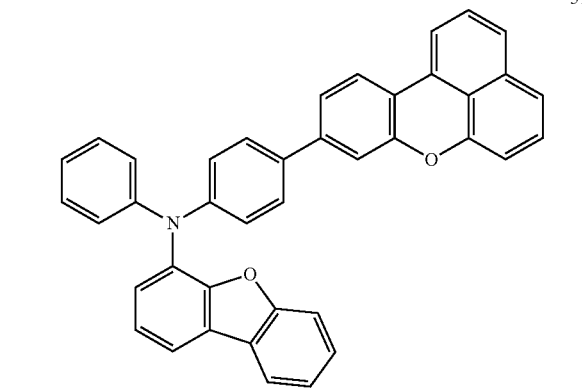
52
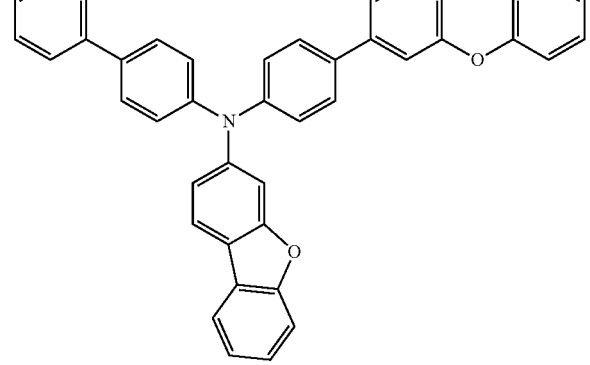
53
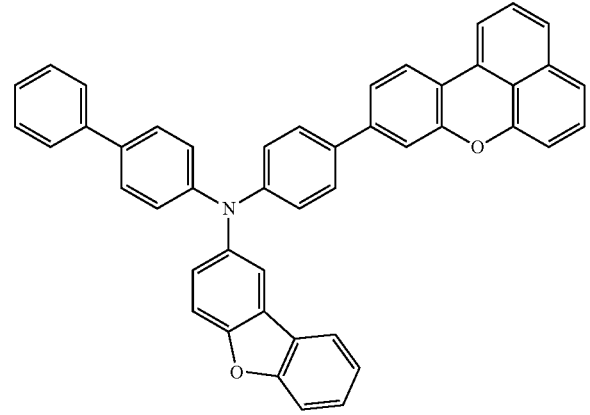

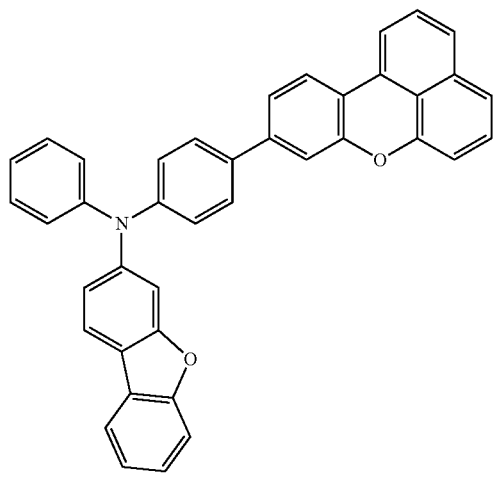
54
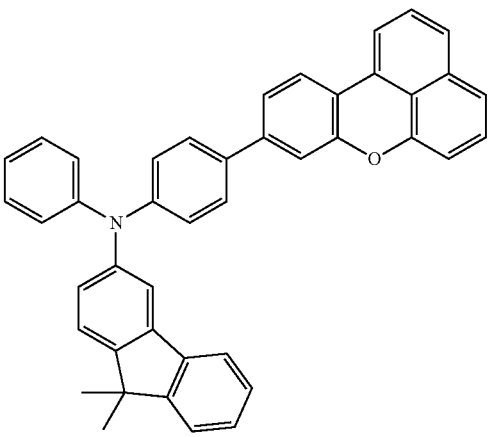
57
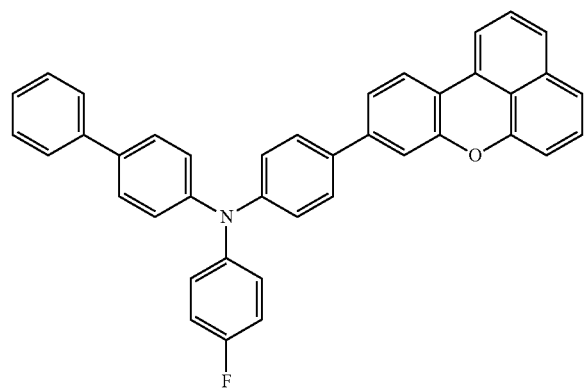
55
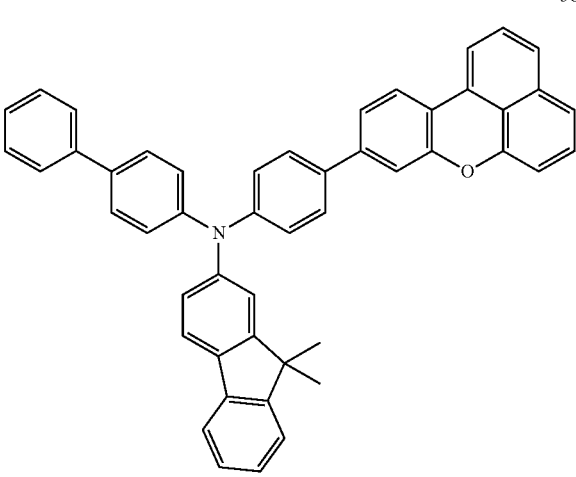
58
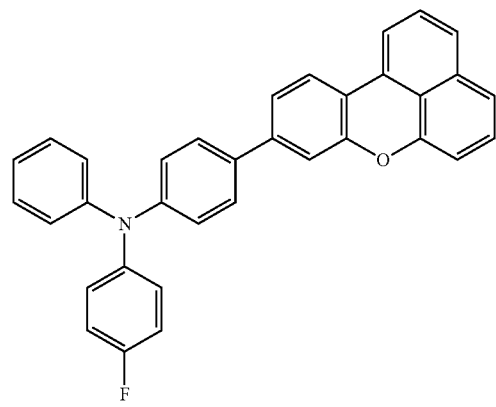
56
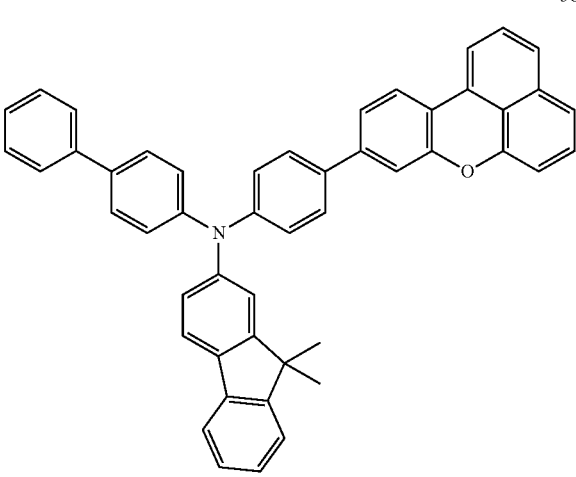
59

60
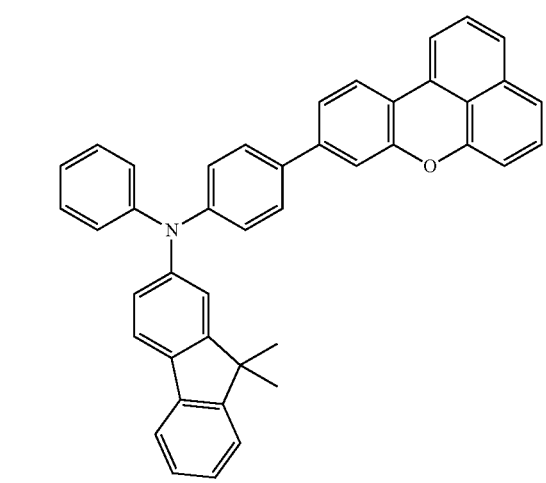
61
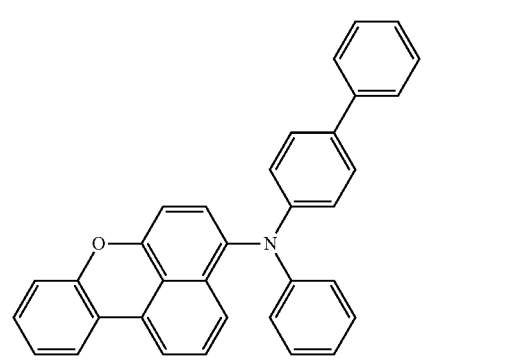
62
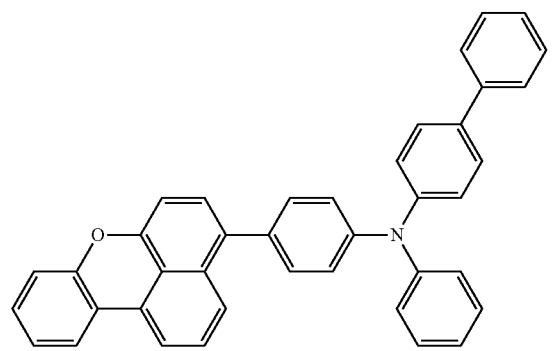
63
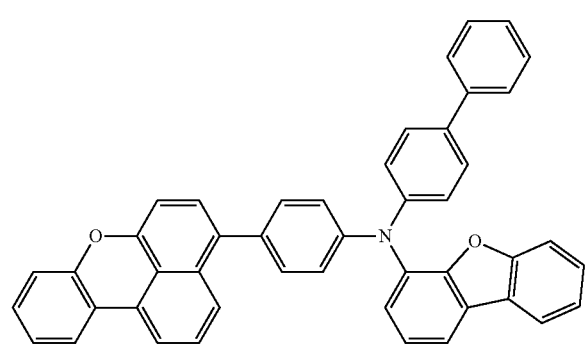
64
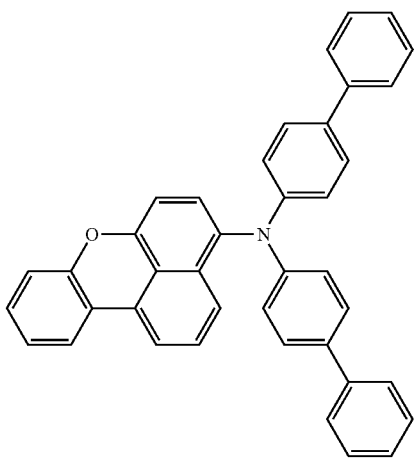
65
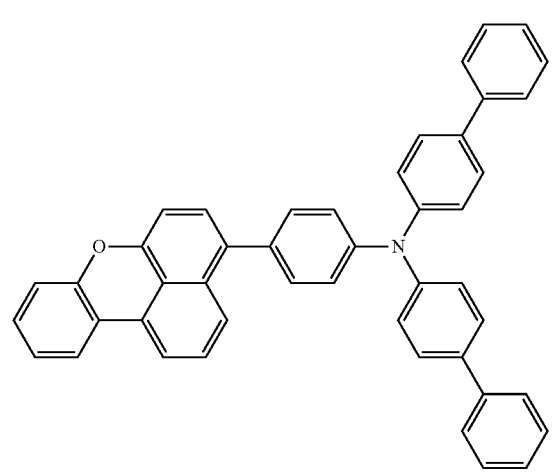
66
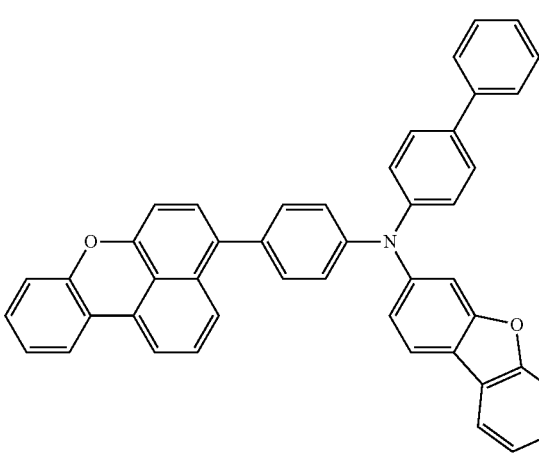

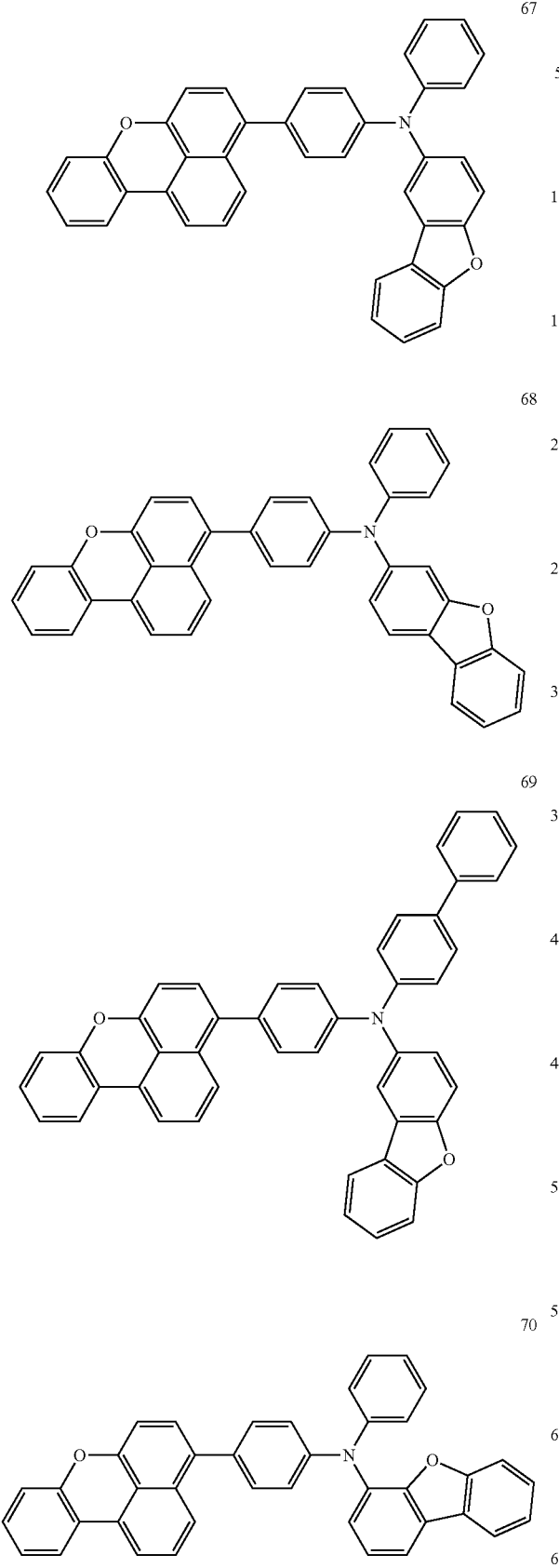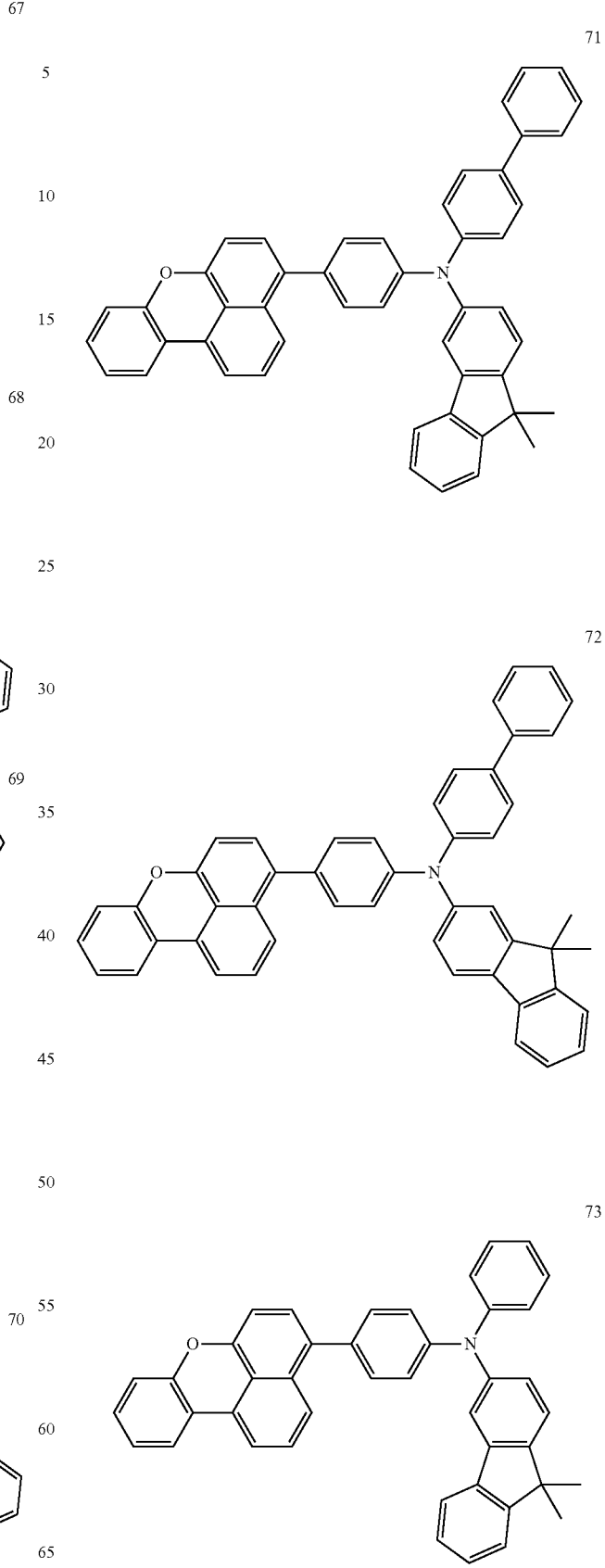

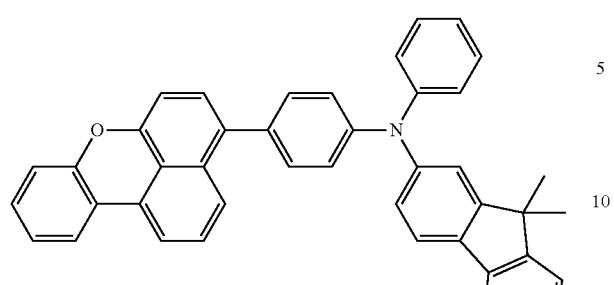
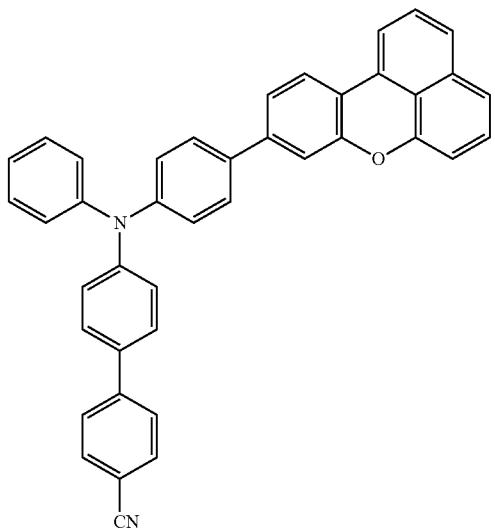
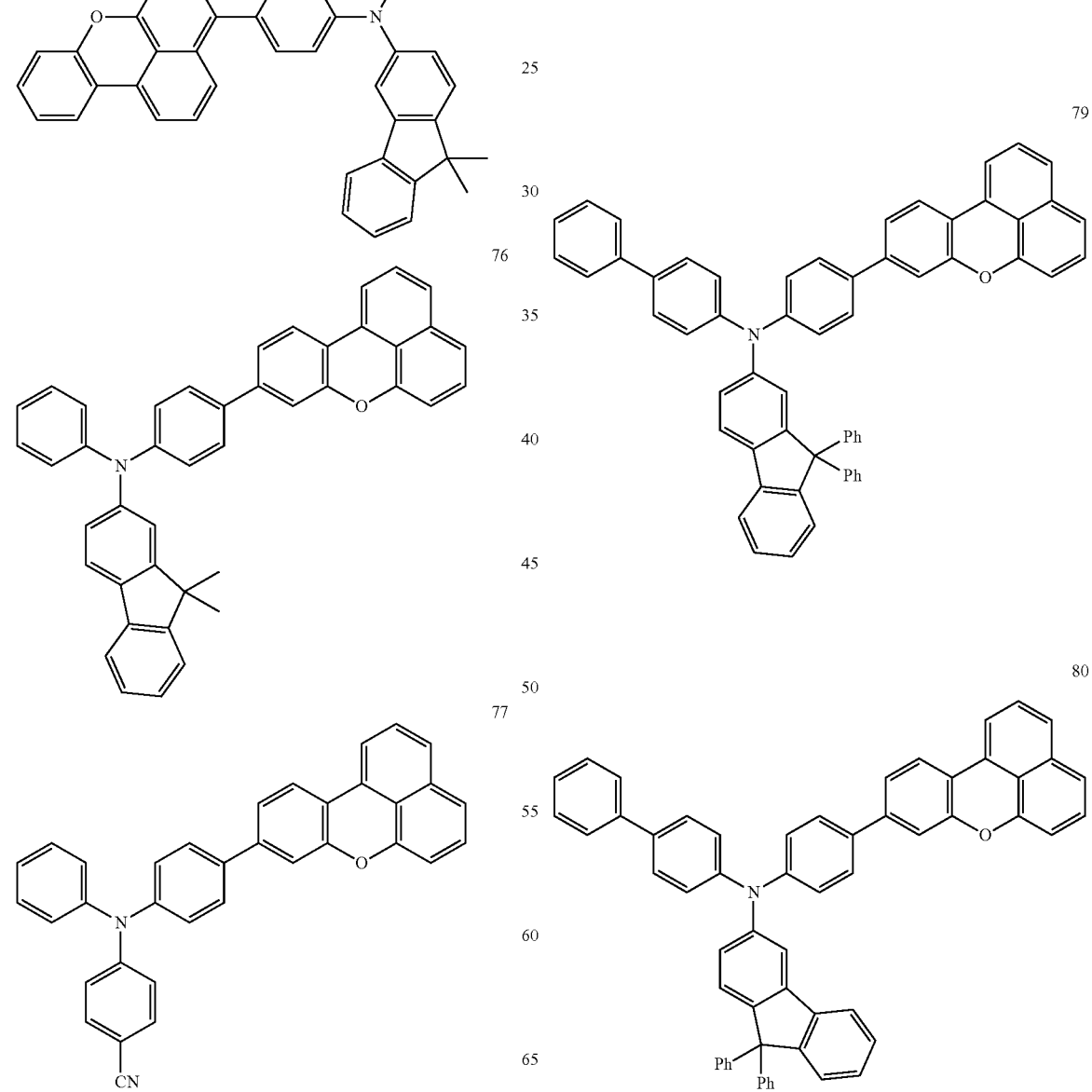

81
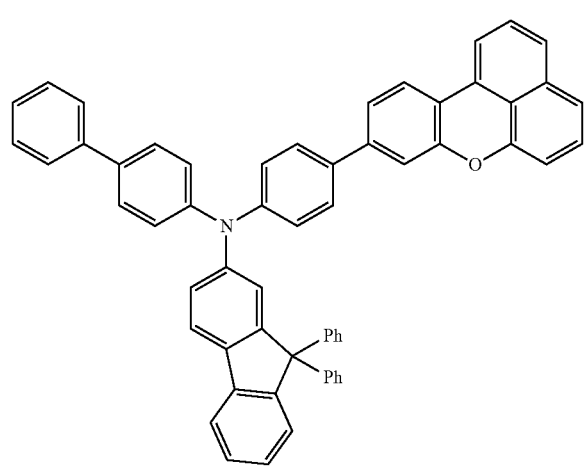
82
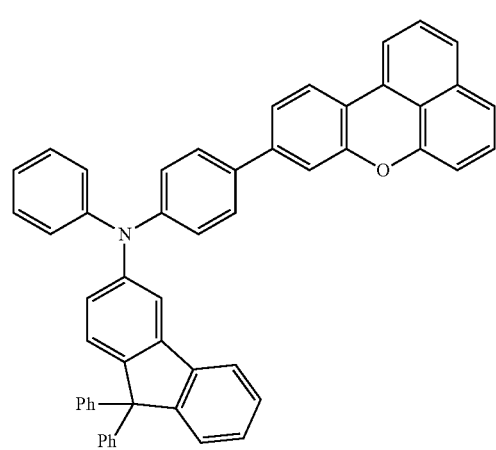
83
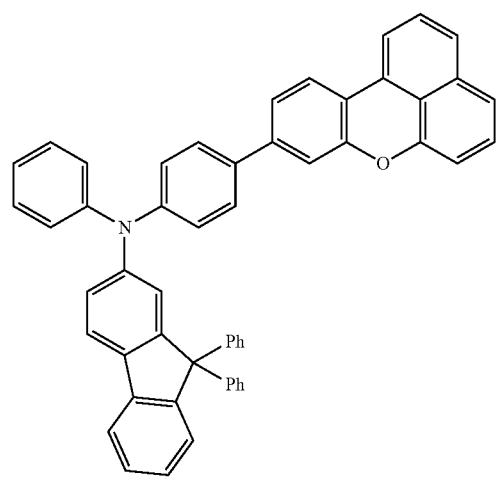
84
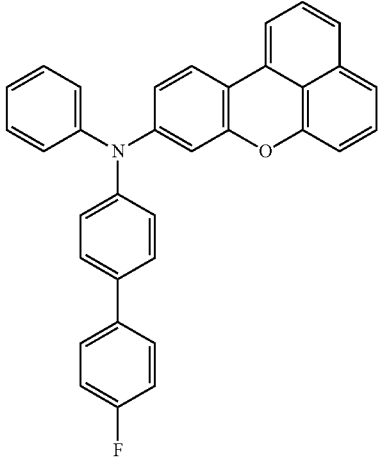
85
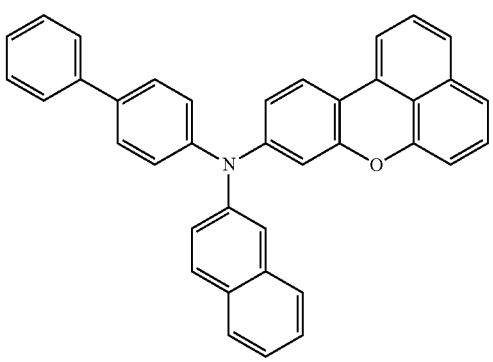
86
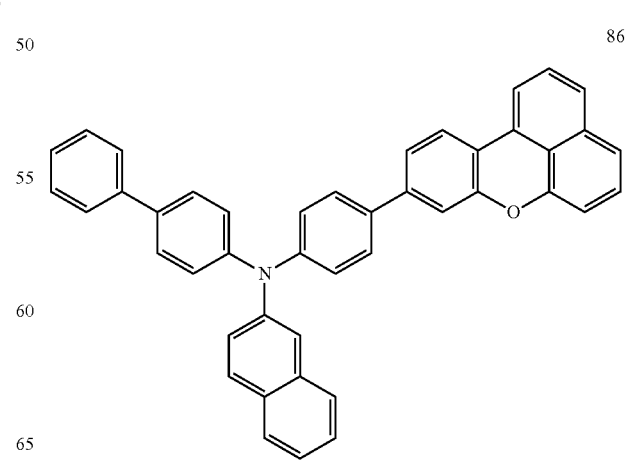

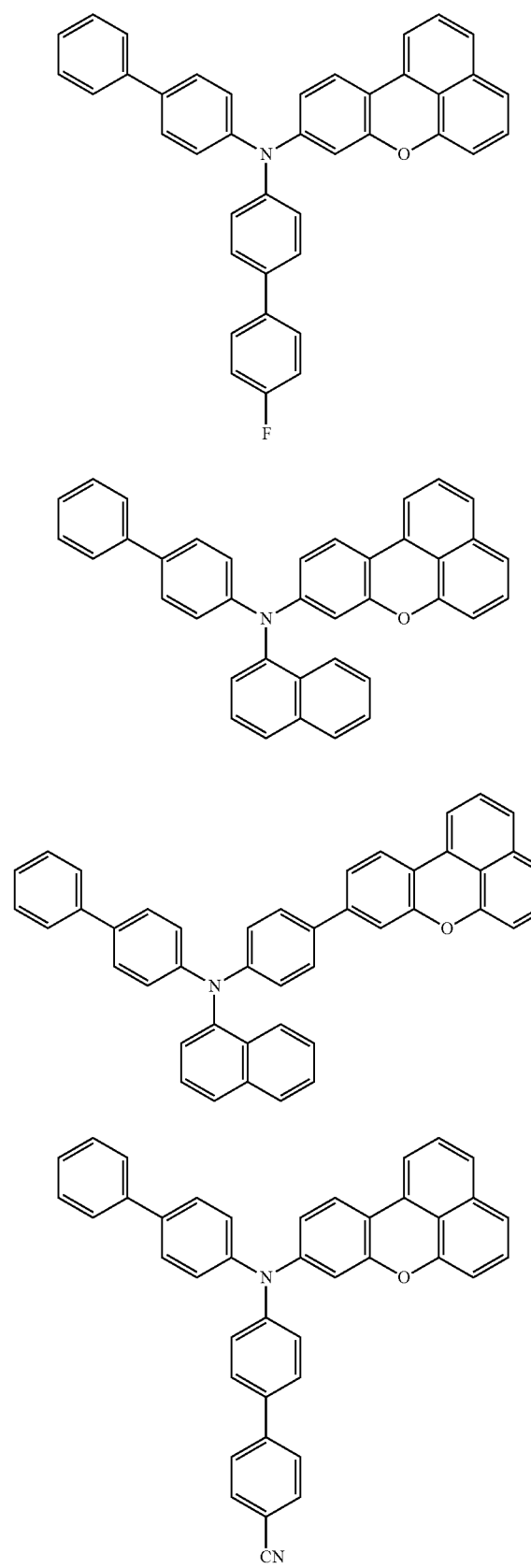

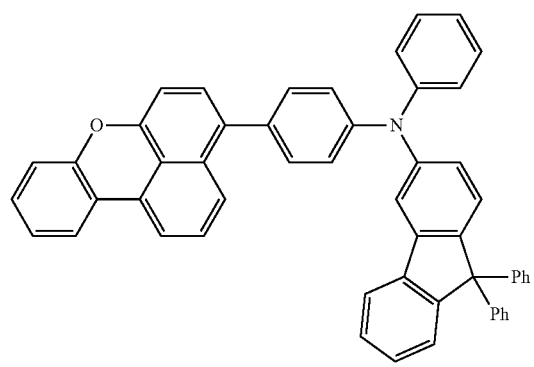
94
95
96
97
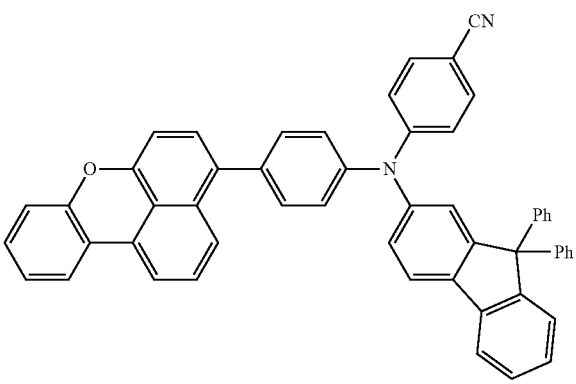
98
99
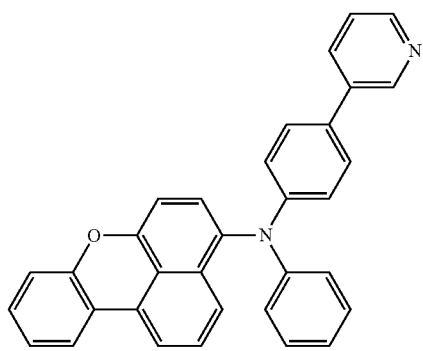
100
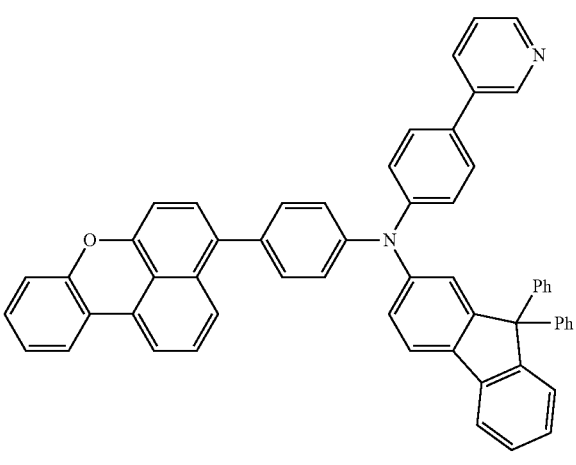
101
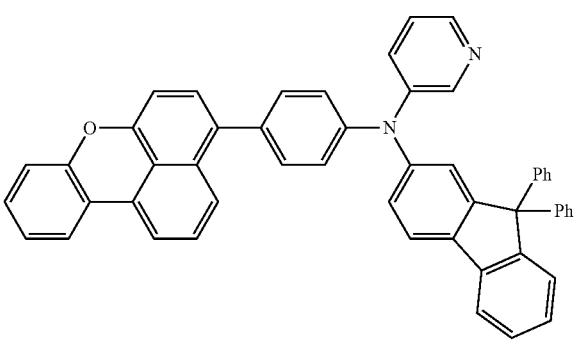

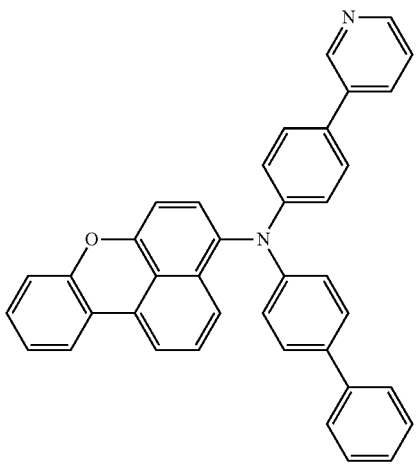

102

Regarding the condensed cyclic compound represented by Formula 1, one selected from $R_1$ to $R_{10}$ may be the group represented by Formula 2, e.g., a "monoamine-based compound" or "monoamine-based moiety."

The condensed cyclic compound represented by Formula 1 may include an amine group in its molecular structure. Due to the presence of the amine group, the condensed cyclic compound may have a high glass transition temperature (Tg) or a high melting point. Accordingly, a heat resistance to Joule heating (occurring inside an organic layer or between an organic layer and an electrode) and a resistance to high temperature environments may increase. Thus, an organic light-emitting device including the condensed cyclic compound represented by Formula 1 may have high durability during preserving and driving.

The condensed cyclic compound represented by Formula 1 may be a benzozanthene derivative. Accordingly, due to hydrogen adjacent to oxygen, the condensed cyclic compound may be easily linked to other condensed cyclic compounds represented by Formula 1 via a hydrogen bond. Thus, when deposition films are formed, a packing density may be increased, faciliating hole mobility. By doing so, excellent hole delivery charactersitics may be obtained. The condensed cyclic compound represented by Formula 1 may be an amine-based or amine-containing compound in which an amine is linked to a benzozanthene core. Accordingly, the condensed cyclic compound may have excellent hole delivery capability, and an organic light-emitting device including the condensed cyclic compound may have a long lifespan.

The condensed cyclic compound represented by Formula 1 may have a planar structure, which facilitates stacking. Accordingly, when deposition films are formed, holes may be allowed to easily migrate, providing excellent hole delivery characteristics. Also, when deposition films are formed, excellent film stability may be obtained. Thus, an organic light-emitting device including the condensed cyclic compound may have excellent film stability.

The condensed cyclic compound represented by Formula 1 may be a monoamine-based or monoamine-containing compound having a single amine group in its molecular structure. Accordingly, the condensed cyclic compound may have an asymmetric structure. Thus, compared to a diamine-based compound having two amine groups in its molecular structure, in the condensed cyclic compound according to an embodiment, a dipole may easily occur. Accordingly, the condensed cyclic compound according to an embodiment may have a stronger polarity than the diamine-based compound, thereby showing higher hole and electron delivery characteristics.

The condensed cyclic compound represented by Formula 1 may be synthesized by a suitable organic synthetic method. A synthesis method of the condensed cyclic compound may be understood in the art in view of the following embodiments.

At least one condensed cyclic compound of Formula 1 may be used or included between a pair of electrodes of an organic light-emitting device. In an implementation, the condensed cyclic compound may be included in a hole transport region, e.g., a hole transport layer. In an implementation, the condensed cyclic compound may be included in an emission layer. For example, an organic light-emitting device according to an embodiment may include: a first electrode; a second electrode facing the first electrode; and an organic layer between the first electrode and the second electrode, the organic layer including an emission layer, wherein the organic layer includes at least one of the condensed cyclic compounds represented by Formula 1 described above.

The expression that "(an organic layer) includes at least one condensed cyclic compound" used herein may include a case in which "(an organic layer) includes identical condensed cyclic compounds represented by Formula 1 and a case in which (an organic layer) includes two or more different condensed cyclic compounds represented by Formula 1.

For example, the organic layer may include, as the condensed cyclic compound, only Compound 1. In this regard, Compound 1 may exist in an emission layer of the organic light-emitting device. In some embodiments, the organic layer may include, as the condensed cyclic compound, Compound 1 and Compound 2. In this regard, Compound 1 and Compound 2 may exist in an identical layer (for example, Compound 1 and Compound 2 may all exist in an emission layer), or different layers (for example, Compound 1 may exist in a hole transport layer and Compound 2 may exist in an emission layer).

The organic layer may include i) a hole transport region that is disposed between the first electrode (anode) and the emission layer and includes at least one of a hole injection layer, a hole transport layer, a buffer layer, and an electron blocking layer, and ii) an electron transport region that is disposed between the emission layer and the second electrode (cathode) and includes at least one selected from a hole blocking layer, an electron transport layer, and an electron injection layer. At least one of the hole transport region and the emission layer may include at least one of the condensed cyclic compound represented by Formula 1. For example, the hole transport region may include the hole transport layer, wherein the hole transport layer may include at least one of the condensed cyclic compound represented by Formula 1.

The term "organic layer" used herein refers to a single layer and/or a plurality of layers disposed between the first electrode and the second electrode of an organic light-emitting device. A material included in the "organic layer" is not limited to an organic material.

FIG. 1 illustrates a schematic view of an organic light-emitting device 10 according to an embodiment. The organic light-emitting device 10 may include a first electrode 110, an organic layer 150, and a second electrode 190.

Hereinafter, the structure of an organic light-emitting device according to an embodiment and a method of manufacturing an organic light-emitting device according to an embodiment will be described in connection with FIG. 1.

In FIG. 1, a substrate may be additionally disposed under the first electrode 110 or above the second electrode 190. The substrate may be a glass substrate or transparent plastic substrate, each with excellent mechanical strength, thermal stability, transparency, surface smoothness, ease of handling, and water-resistance.

The first electrode 110 may be formed by depositing or sputtering a material for forming the first electrode on the substrate. When the first electrode 110 is an anode, the material for the first electrode 110 may be selected from materials with a high work function to facilitate hole injection. The first electrode 110 may be a reflective electrode or a transmissive electrode. The material for the first electrode 110 may be a transparent and highly conductive material, e.g., indium tin oxide (ITO), indium zinc oxide (IZO), tin oxide ($SnO_2$), and zinc oxide (ZnO). When the first electrode 110 is a semi-transmissive electrode or a reflective electrode, as a material for forming the first electrode, at least one of magnesium (Mg), aluminum (Al), aluminum-lithium (Al—Li), calcium (Ca), magnesium-indium (Mg—In), magnesium-silver (Mg—Ag) may be used.

The first electrode 110 may have a single-layer structure, or a multi-layer structure including two or more layers. For example, the first electrode 110 may have a three-layered structure of ITO/Ag/ITO.

An organic layer 150 may be disposed on the first electrode 110. The organic layer 150 may include an emission layer.

The organic layer 150 may further include a hole transport region between the first electrode and the emission layer, and/or an electron transport region between the emission layer and the second electrode.

The hole transport region may include at least one selected from a hole injection layer (HIL), a hole transport layer (HTL), a buffer layer, and an electron blocking layer (EBL). The electron transport region may include at least one selected from a hole blocking layer (HBL), an electron transport layer (ETL), and an electron injection layer (EIL).

The hole transport region may have a single-layered structure formed of a single material, a single-layered structure formed of a plurality of different materials, or a multi-layered structure having a plurality of layers formed of a plurality of different materials.

For example, the hole transport region may have a single-layered structure formed of a plurality of different materials, or a structure of hole injection layer/hole transport layer, a structure of hole injection layer/hole transport layer/buffer layer, a structure of hole injection layer/buffer layer, a structure of hole transport layer/buffer layer, or a structure of hole injection layer/hole transport layer/electron blocking layer, wherein layers of each structure are sequentially stacked from the first electrode 110 in this stated order.

When the hole transport region includes a hole injection layer, the hole injection layer may be formed on the first electrode 110 by using various methods, such as vacuum deposition, spin coating casting, a Langmuir-Blodgett (LB) method, ink-jet printing, laser-printing, or laser-induced thermal imaging.

When a hole injection layer is formed by vacuum deposition, for example, the vacuum deposition may be performed at a temperature of a deposition temperature of about 100 to about 500° C., at a vacuum degree of about $10^{-8}$ to about $10^{-3}$ torr, and at a deposition rate of about 0.01 to about 100 Å/sec in consideration of a compound for a hole injection layer to be deposited, and the structure of a hole injection layer to be formed.

When a hole injection layer is formed by spin coating, the spin coating may be performed at a coating rate of about 2000 rpm to about 5000 rpm, and at a temperature of about 80° C. to 200° C. in consideration of a compound for a hole injection layer to be deposited, and the structure of a hole injection layer to be formed.

When the hole transport region includes a hole transport layer, the hole transport layer may be formed on the first electrode 110 or the hole injection layer by using various methods, such as vacuum deposition, spin coating, casting, a LB method, ink-jet printing, laser-printing, or laser-induced thermal imaging. When the hole transport layer is formed by vacuum deposition or spin coating, deposition and coating conditions for the hole transport layer may be determined by referring to the deposition and coating conditions for the hole injection layer.

The hole transport region may include the condensed cyclic compound represented by Formula 1. For example, the hole transport region may include the hole transport layer, and the hole transport layer may include the condensed cyclic compound represented by Formula 1.

In an implementation, the hole transport region may include at least one selected from m-MTDATA, TDATA, 2-TNATA, NPB, β-NPB, TPD, Spiro-TPD, Spiro-NPB, α-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (PANI/CSA), (polyaniline)/poly(4-styrenesulfonate) (Pani/PSS), a compound represented by Formula 201 below, and a compound represented by Formula 202 below.

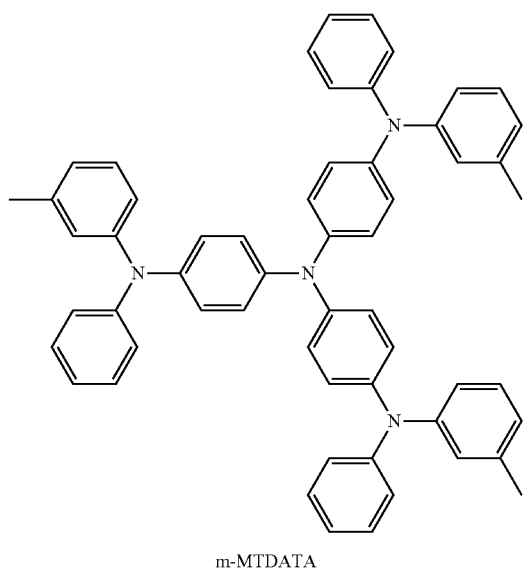

m-MTDATA

-continued
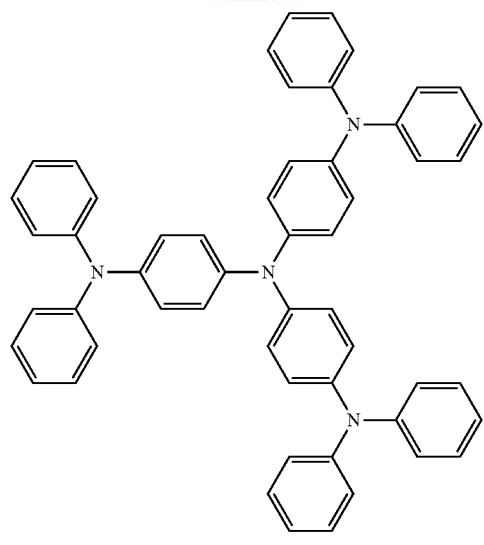
TDATA
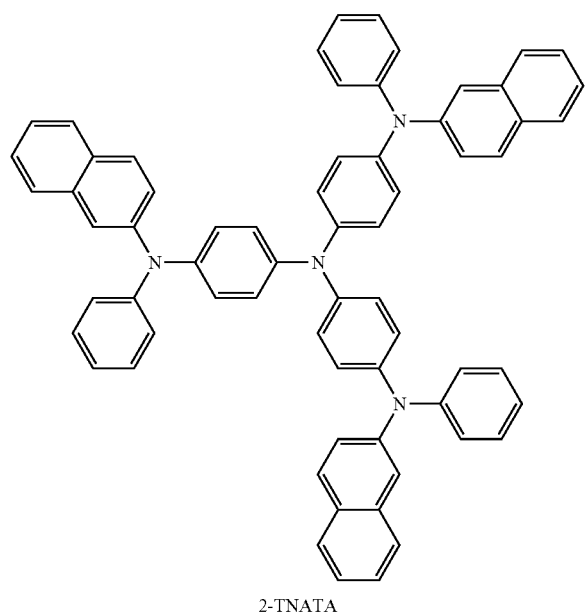
2-TNATA
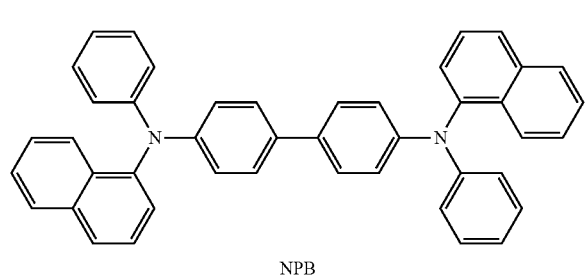
NPB
-continued
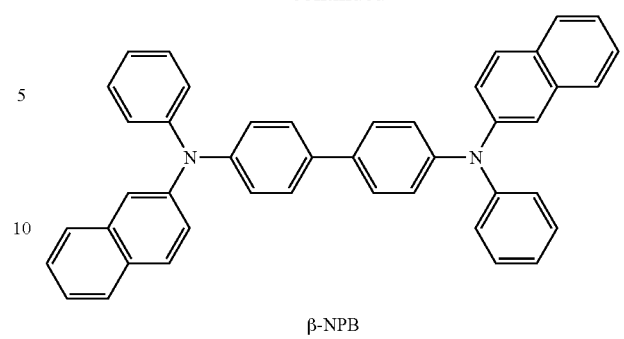
β-NPB
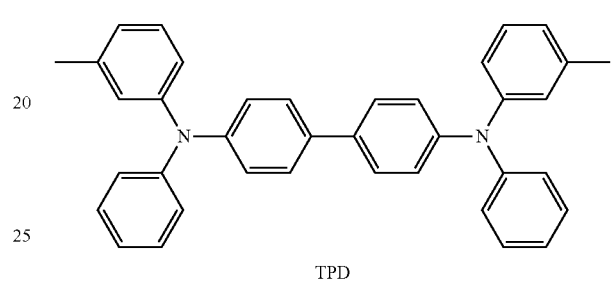
TPD
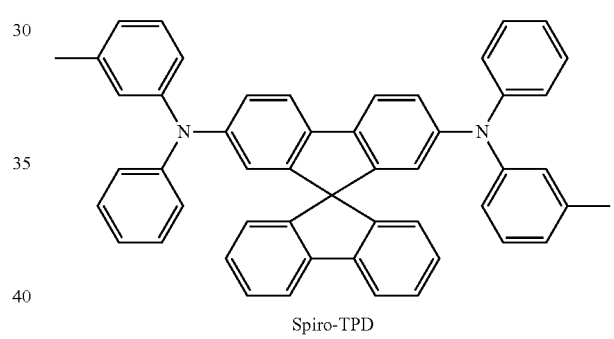
Spiro-TPD
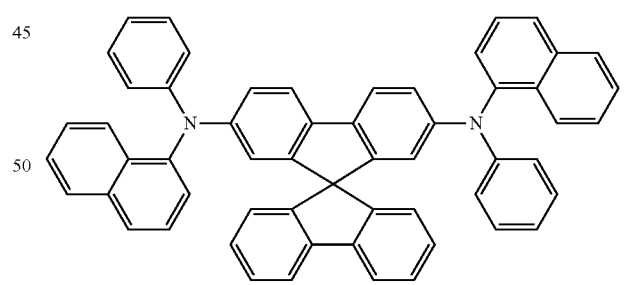
Spiro-NPB
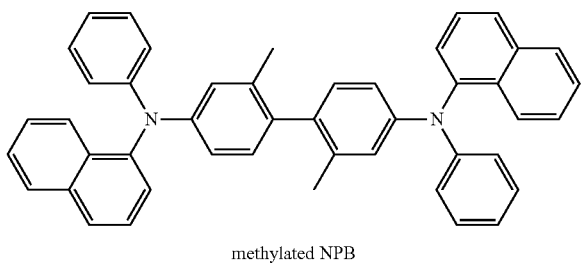
methylated NPB

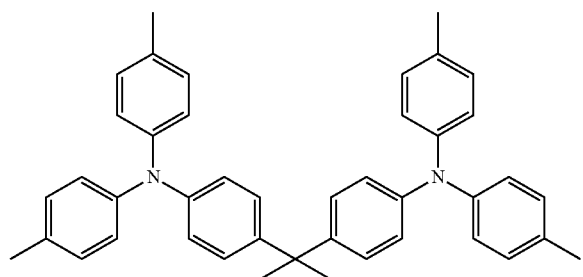

TAPC

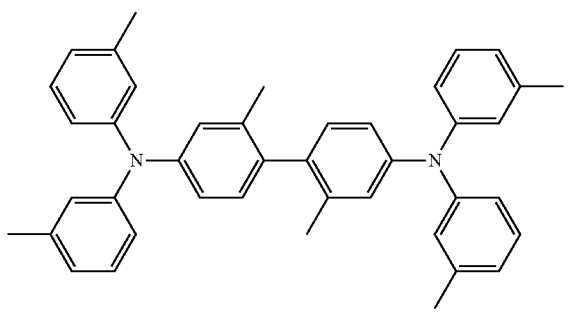

HMTPD

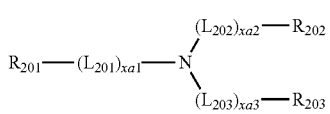

<Formula 201>

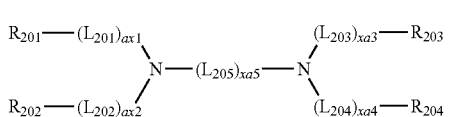

<Formula 202>

In Formulae 201 and 202, $L_{201}$ to $L_{205}$ may be the same as explained in connection with $L_1$;

xa1 to xa4 may be each independently selected from 0, 1, 2, and 3;

xa5 may be selected from 1, 2, 3, 4, and 5; and $R_{201}$ to $R_{204}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, in Formulae 201 and 202, $L_{201}$ to $L_{205}$ may each independently be selected from a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 may each independently be 0, 1, or 2;

xa5 may be 1, 2, or 3;

$R_{201}$ to $R_{204}$ may each independently be selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

The compound represented by Formula 201 may be represented by Formula 201A:

<Formula 201A>

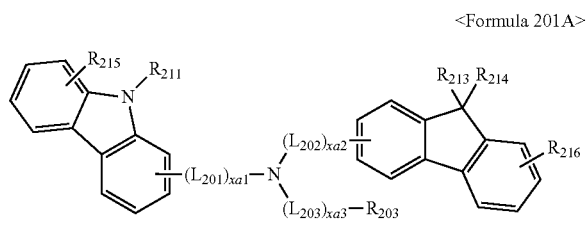

For example, the compound represented by Formula 201 may be represented by Formula 201A-1 below:

<Formula 201A-1>

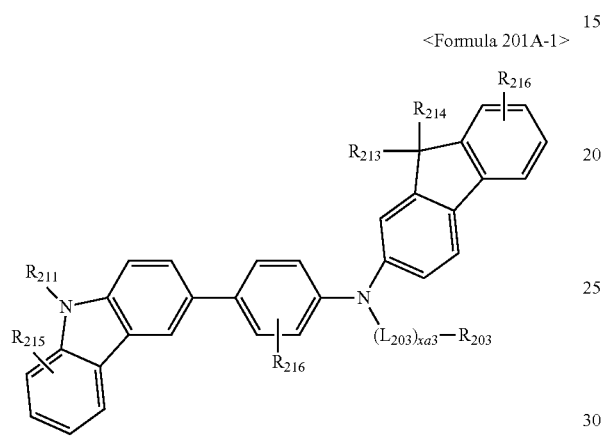

For example, the compound represented by Formula 202 may be represented by Formula 202A below:

<Formula 202A>

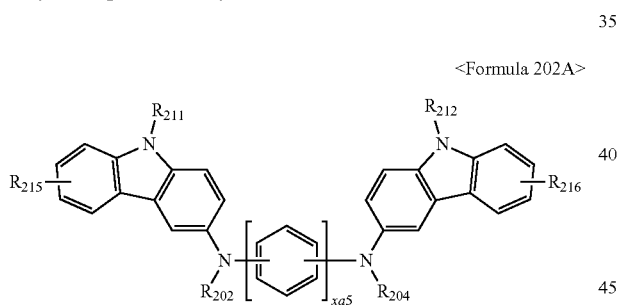

$L_{201}$ to $L_{203}$, xa1 to xa3, xa5, and $R_{202}$ to $R_{204}$ in Formulae 201A, 201A-1, and 202A are already described above, $R_{211}$ is the same as defined in connection with $R_{203}$, and $R_{213}$ to $R_{216}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

The compound represented by Formula 201, and the compound represented by Formula 202 may include compounds HT1 to HT20 illustrated below.

HT1

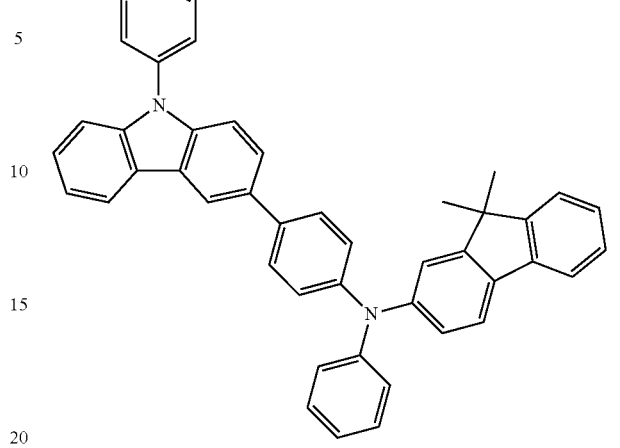

HT2

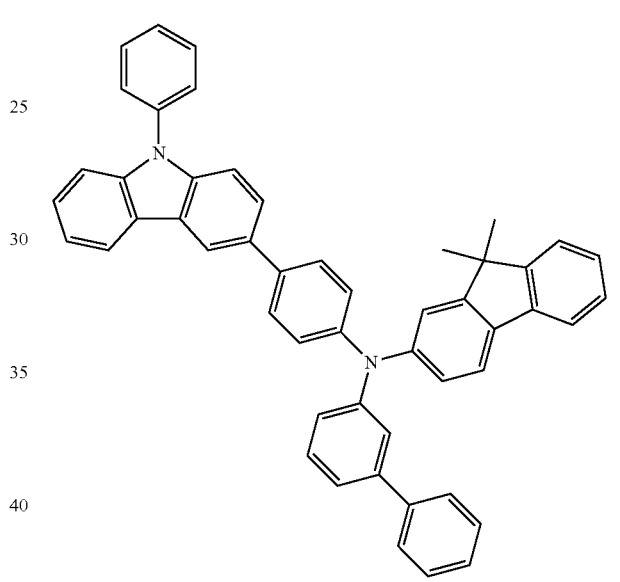

HT3

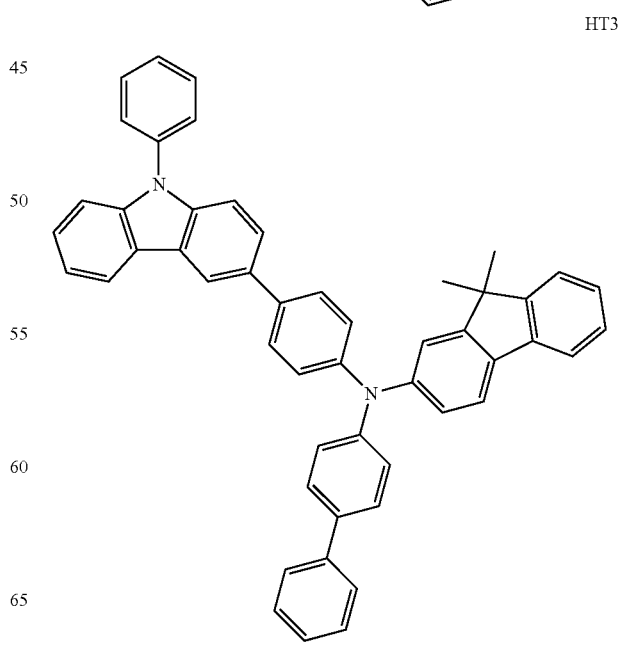

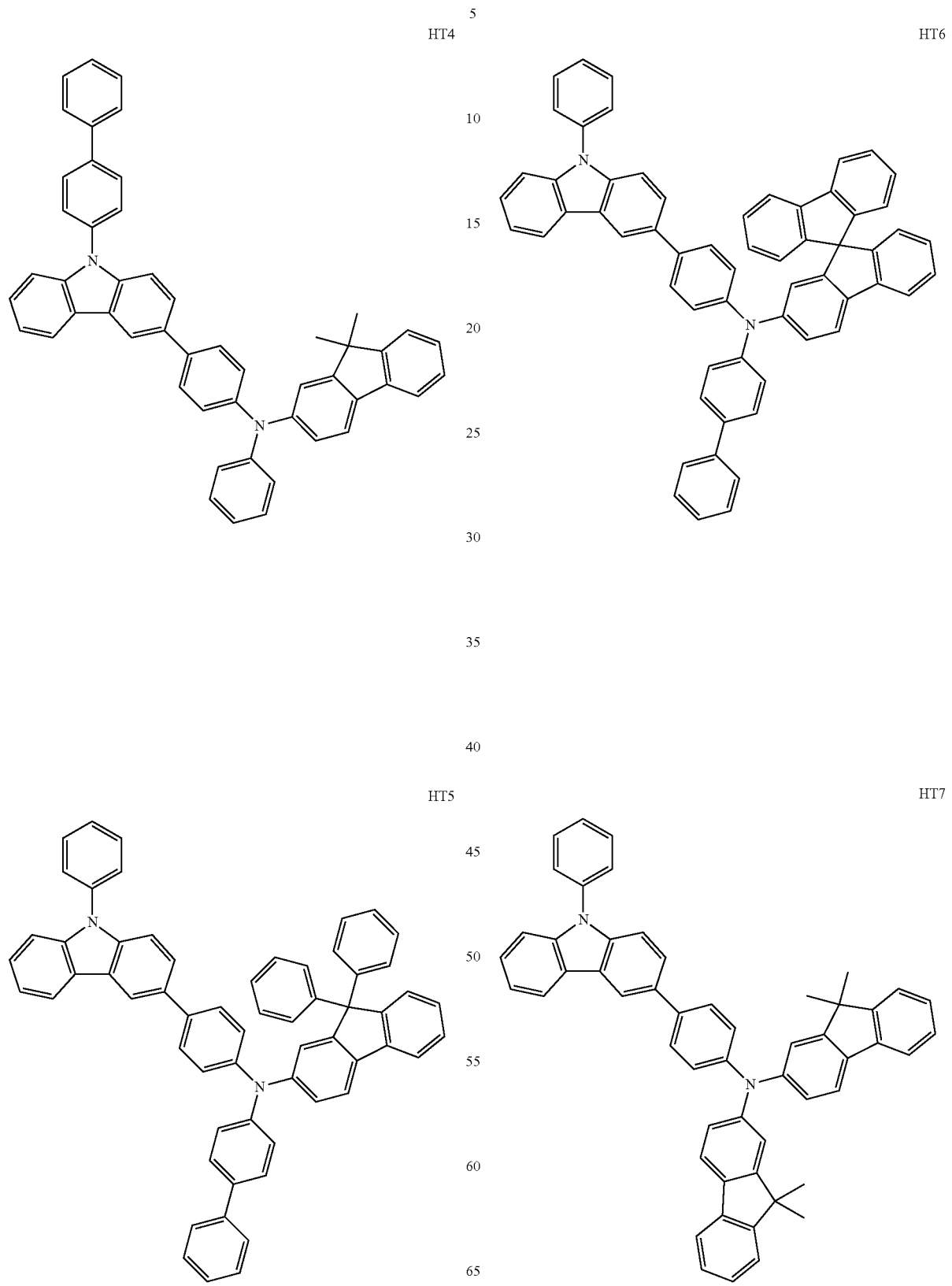

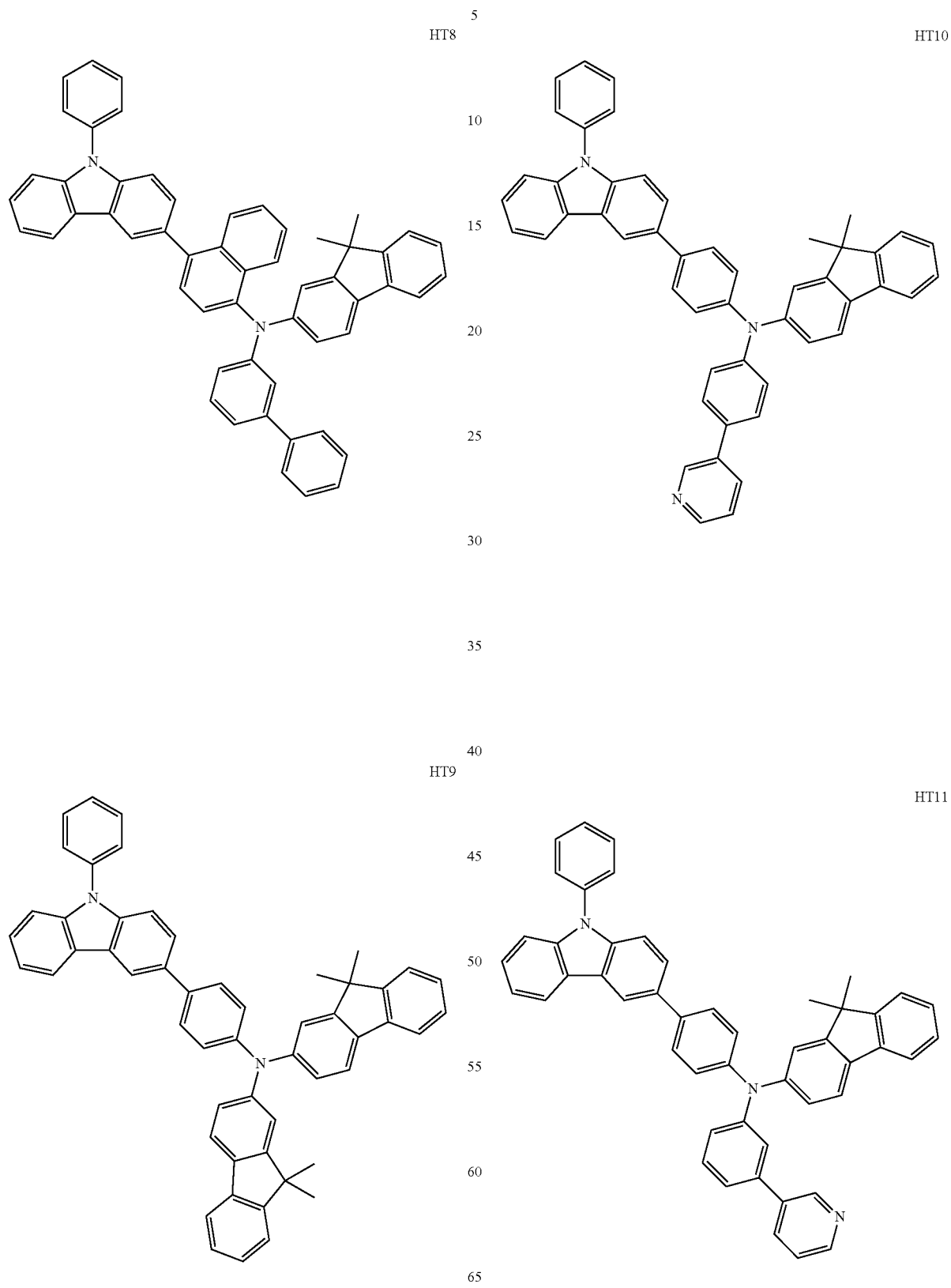

HT12
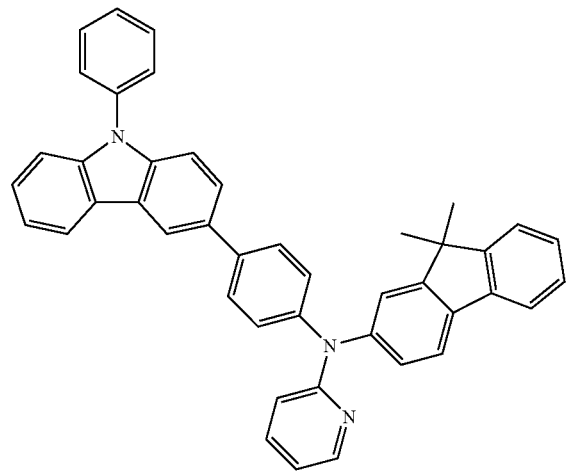
HT13
HT14
HT15
HT16
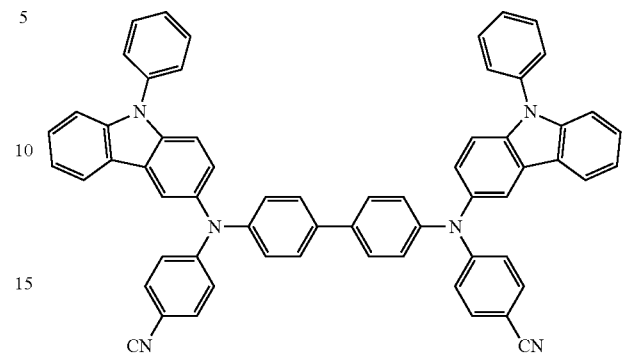
HT17
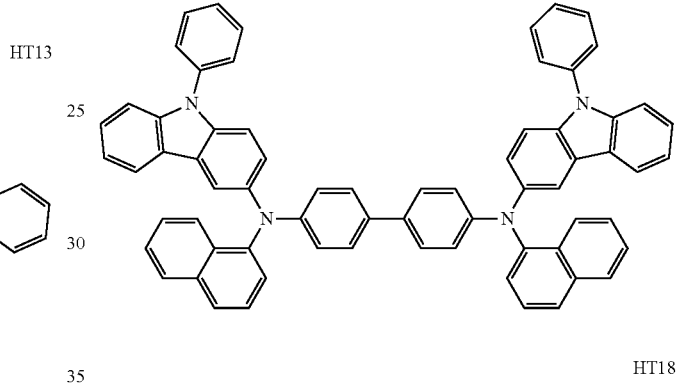
HT18
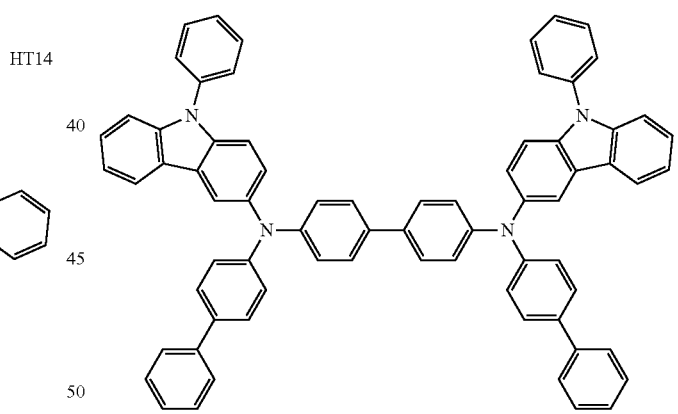
HT19
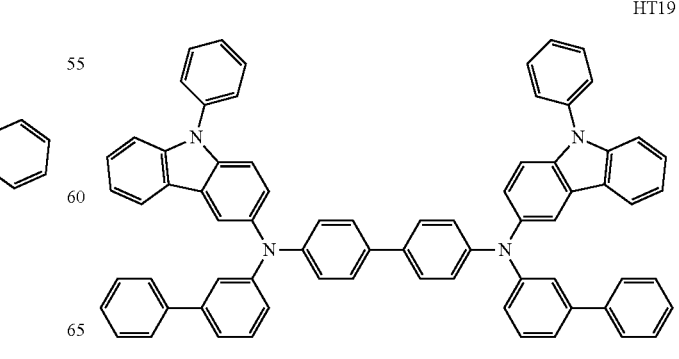

HT20

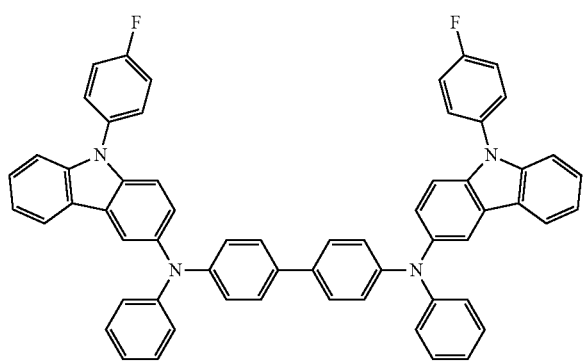

A thickness of the hole transport region may be in a range of about 100 Å to about 10000 Å, for example, about 100 Å to about 1000 Å. When the hole transport region includes a hole injection layer and a hole transport layer, the thickness of the hole injection layer may be in a range of about 100 Å to about 10000 Å, and for example, about 100 Å to about 1000 Å, and the thickness of the hole transport layer may be in a range of about 50 Å to about 2000 Å, and for example, about 100 Å to about 1500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or unhomogeneously dispersed in the hole transport region.

The charge-generation material may be, e.g., a p-dopant. The p-dopant may be one selected from a quinone derivative, a metal oxide, and a cyano group-containing compound. For example, non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide, and Compound HT-D1 illustrated below.

<Compound HT-D1>

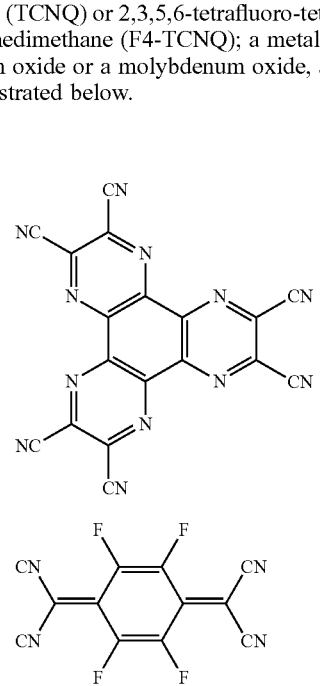

<F4-TCNQ>

The hole transport region may further include, in addition to the hole injection layer and the hole transport layer, at least one of a buffer layer and an electron blocking layer. Since the buffer layer may compensate for an optical resonance distance according to a wavelength of light emitted from the emission layer, light-emission efficiency of a formed organic light-emitting device may be improved. For use as a material included in the buffer layer, materials that are included in the hole transport region may be used. The electron blocking layer prevents injection of electrons from the electron transport region.

An emission layer may be formed on the first electrode 110 or the hole transport region by using various methods, such as vacuum deposition, spin coating, casting, a LB method, ink-jet printing, laser-printing, or laser-induced thermal imaging. When the emission layer is formed by vacuum deposition or spin coating, deposition and coating conditions for the emission layer may be determined by referring to the deposition and coating conditions for the hole injection layer.

When the organic light-emitting device 10 is a full color organic light-emitting device, the emission layer may be patterned into a red emission layer, a green emission layer, or a blue emission layer, according to a sub pixel. In some embodiments, the emission layer may have a stacked structure of a red emission layer, a green emission layer, and a blue emission layer, or may include a red-light emission material, a green-light emission material, and a blue-light emission material, which are mixed with each other in a single layer, to emit white light.

The emission layer may include a host and a dopant.

The host may include at least one selected from TPBi, TBADN, ADN (also referred to as "DNA"), CBP, CDBP, and TCP:

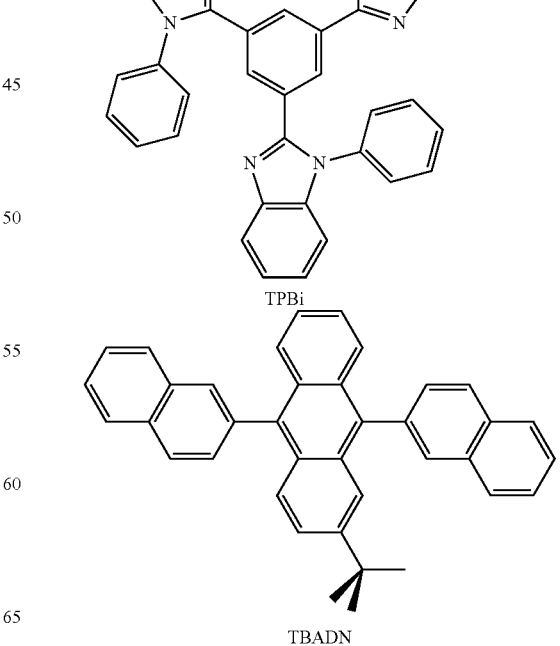

TPBi

TBADN

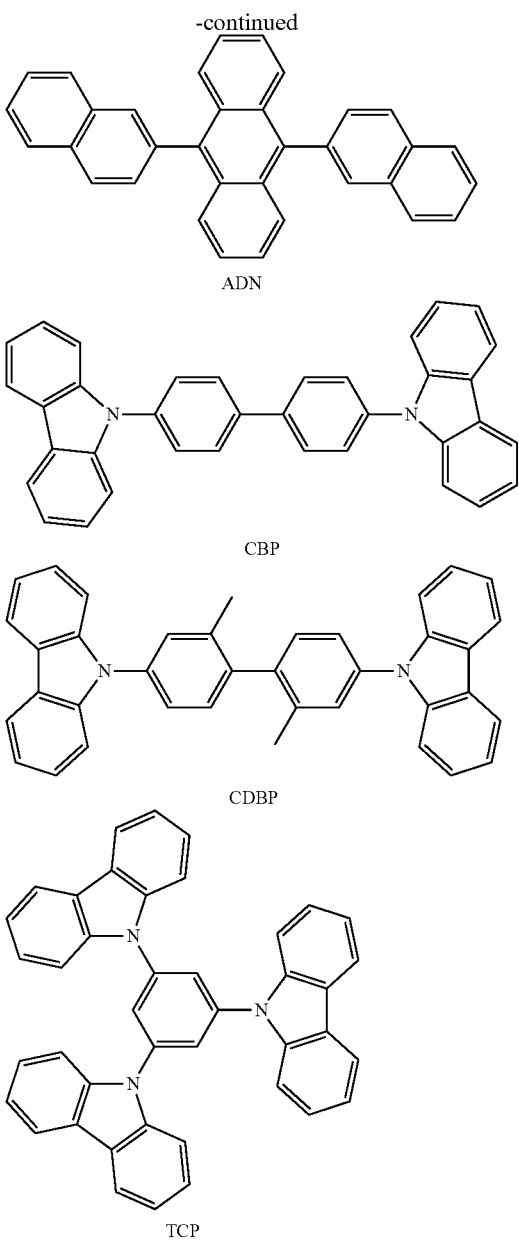

ADN

CBP

CDBP

TCP

In some embodiments, the host may include a compound represented by Formula 301 below.

$$Ar_{301}\text{-}[(L_{301})_{xb1}\text{-}R_{301}]_{xb2}$$ <Formula 301> wherein in Formula 301, $Ar_{301}$ may be selected from a naphthalene, a heptalene, a fluorenene, a spiro-fluorenene, a benzofluorenene, a dibenzofluorenene, a phenalene, a phenanthrene, an anthracene, a fluoranthene, a triphenylene, a pyrene, a chrysene, a naphthacene, a picene, a perylene, a pentaphene, and an indenoanthracene;

a naphthalene group, a heptalene group, a fluorenene group, a spiro-fluorenene group, a benzofluorenene group, a dibenzofluorenene group, a phenalene group, a phenanthrene group, a anthracene group, a fluoranthene group, a triphenylene group, a pyrene group, a chrysene group, a naphthacene group, a picene group, a perylene group, a pentaphene group, and an indenoanthracene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si$(Q_{301})(Q_{302})(Q_{303})$ (wherein $Q_{301}$ to $Q_{303}$ are each independently selected from a hydrogen, a $C_1$-$C_{60}$ alkyl group, a $C_2$-$C_{60}$ alkenyl group, a $C_1$-$C_{60}$ aryl group, and a $C_1$-$C_{60}$ heteroaryl group);

$L_{301}$ may be the same as explained in connection with $L_1$;

$R_{301}$ may be selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazol group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 may be selected from 0, 1, 2, and 3;

xb2 may be selected from 1, 2, 3, and 4.

wherein in Formula 301,

L$_{301}$ may be selected from a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

R$_{301}$ may be selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group.

For example, the host may include a compound represented by Formula 301A below:

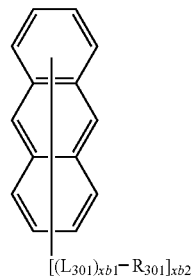

<Formula 301A>

Descriptions of substituents of Formula 301A may be understood by referring to the descriptions provided herein.

The compound represented by Formula 301 may include at least one of Compounds H1 to H42:

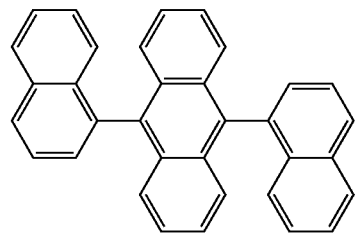

H1

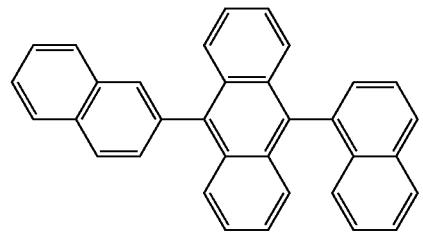

H2

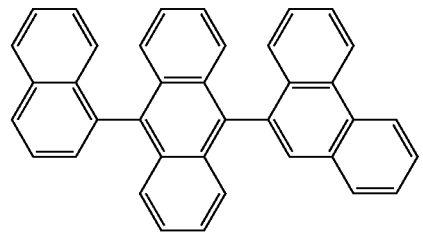

H3

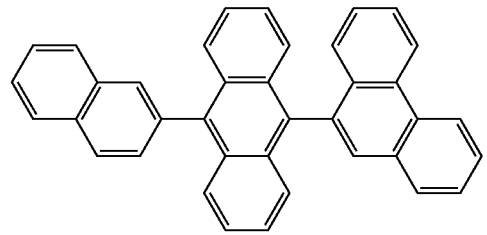

H4

-continued
H5
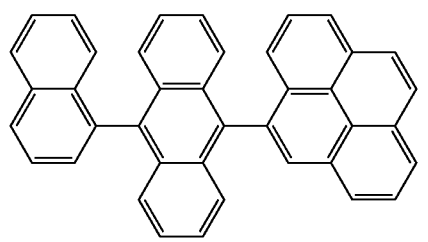
H6
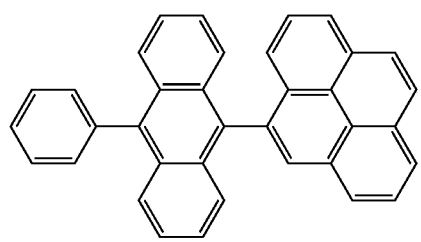
H7
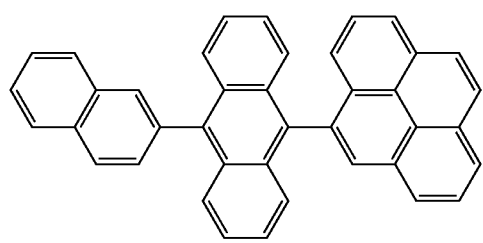
H8
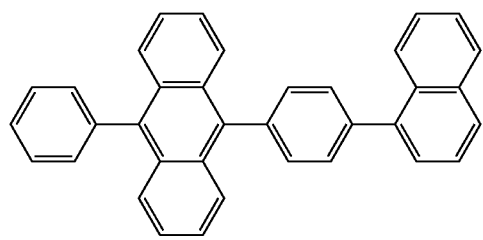
H9
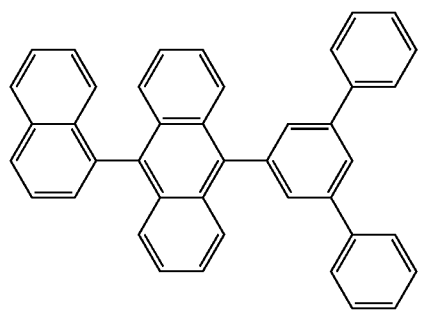
H10
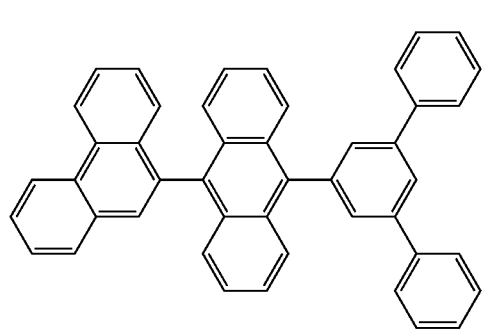
-continued
H11
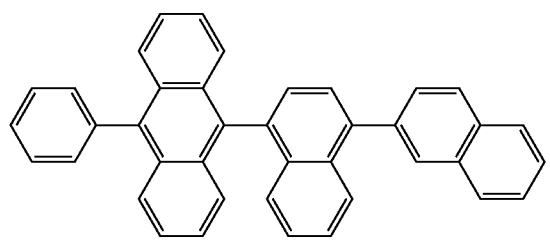
H12
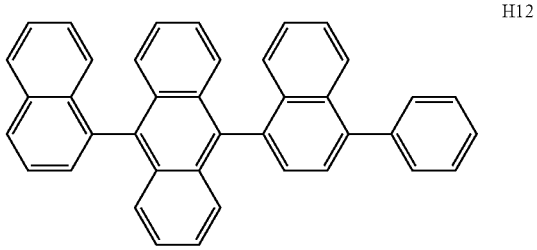
H13
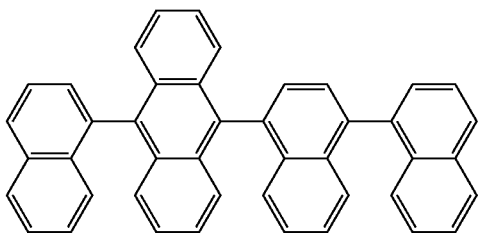
H14
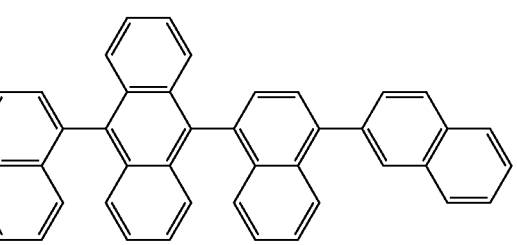
H15
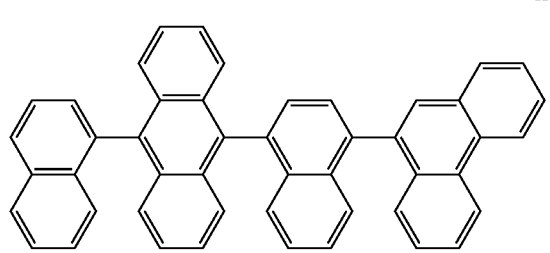
H16
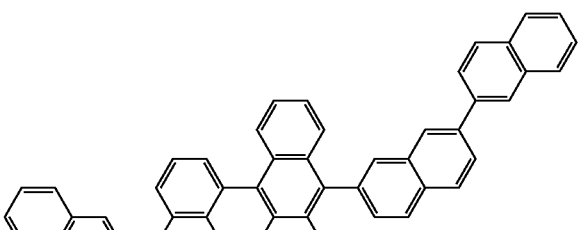

H17
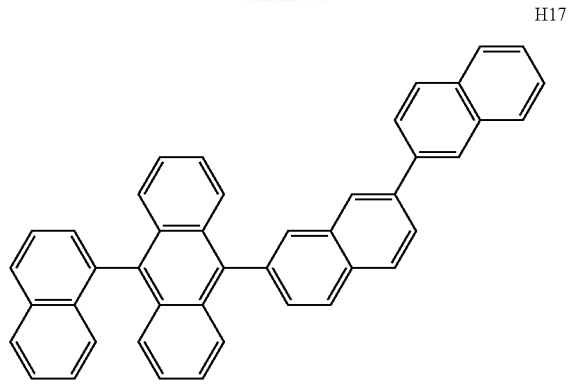
H18
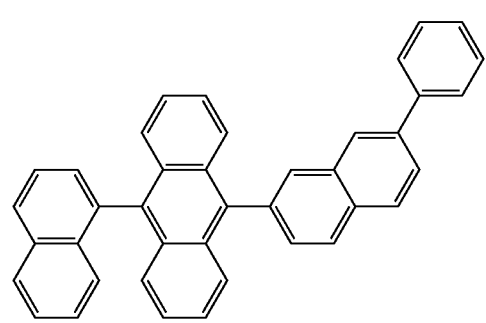
H19
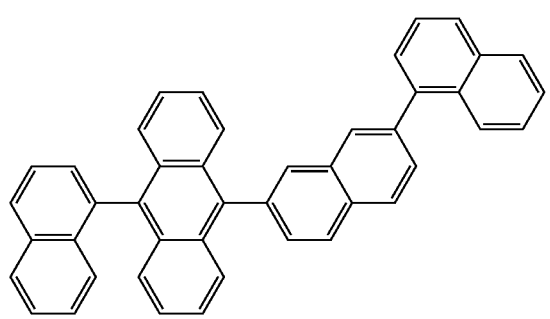
H20
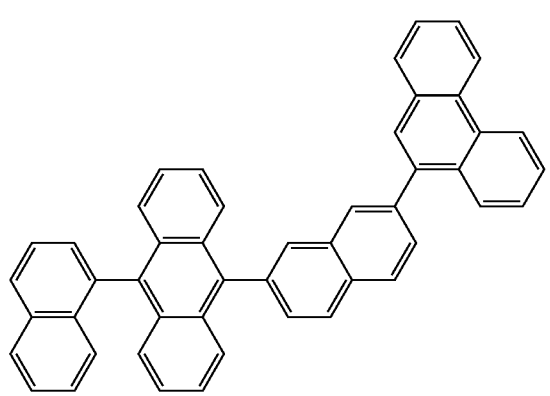
H21
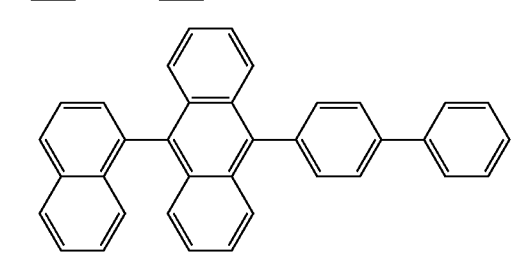
H22
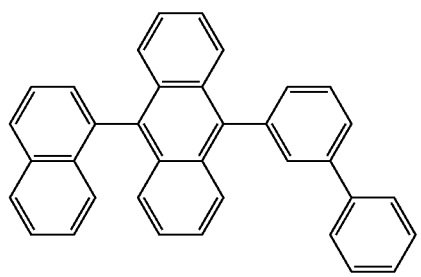
H23
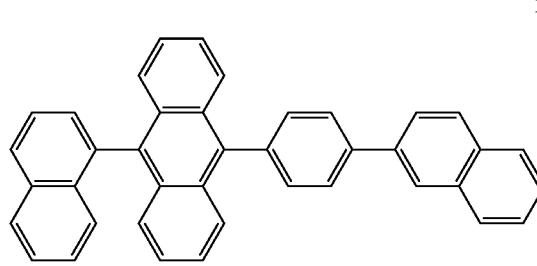
H24
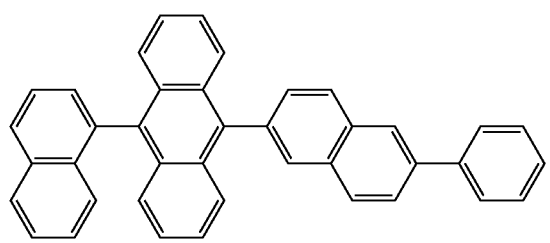
H25
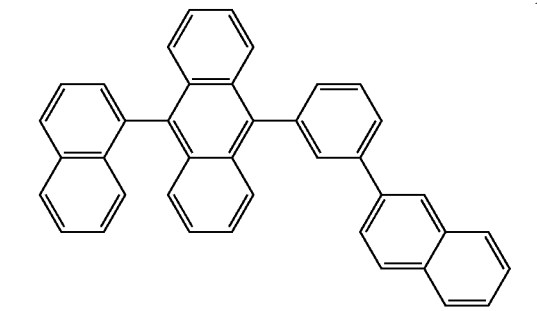
H26
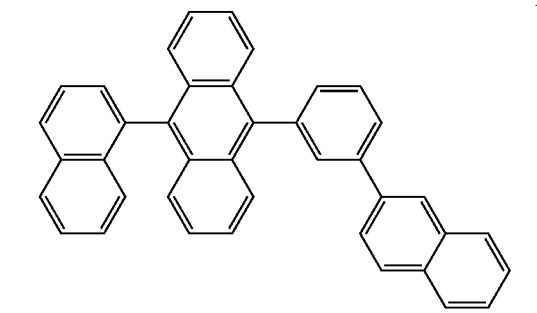

H27
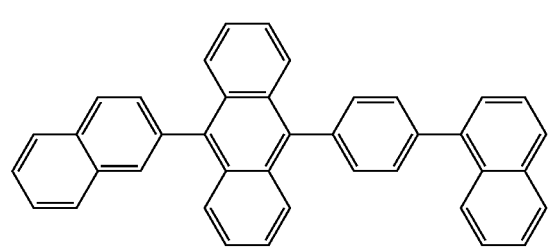
H28
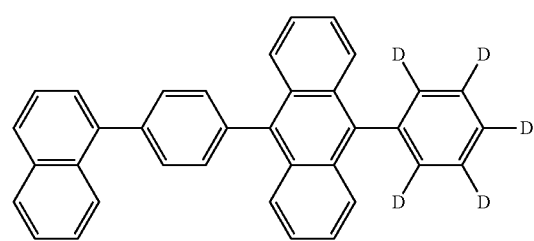
H29
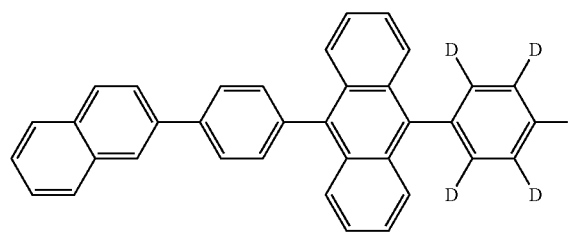
H30
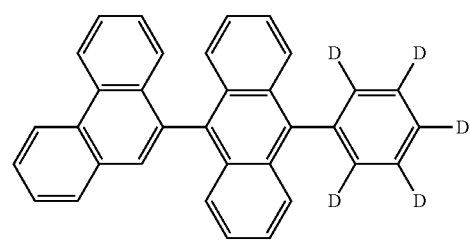
H31
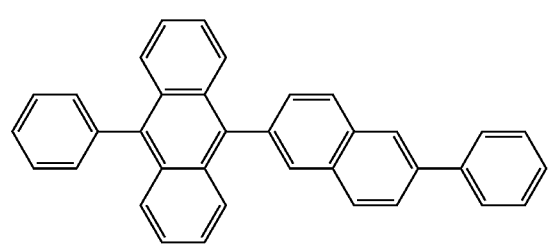
H32
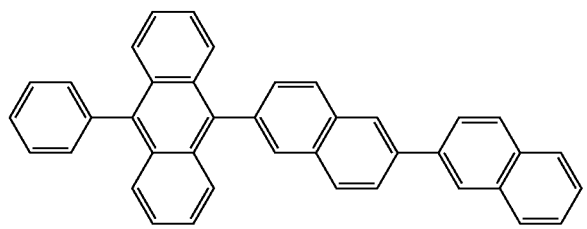
H33
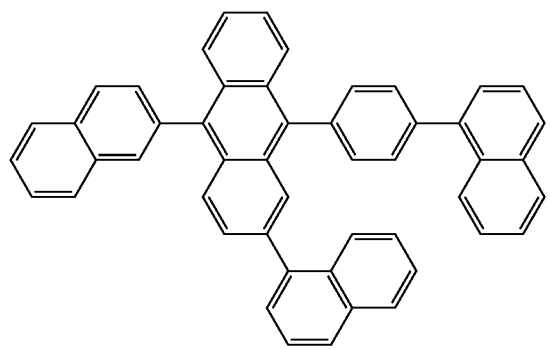
H34
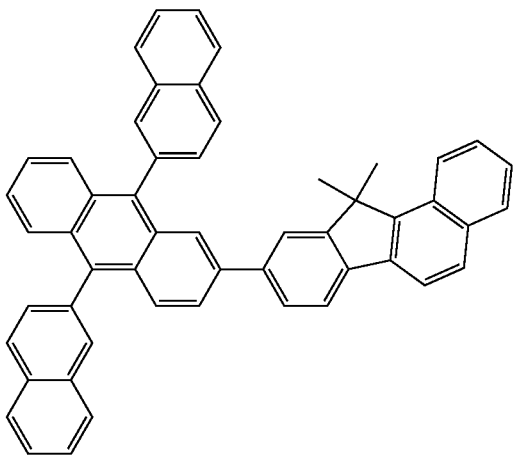
H35
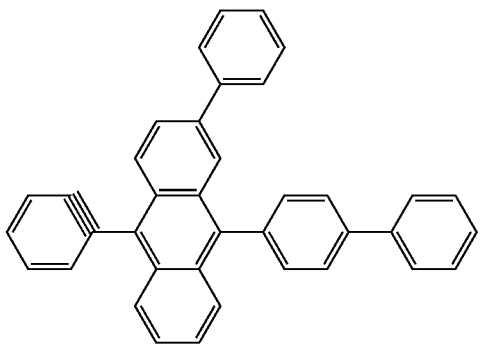

-continued
H36
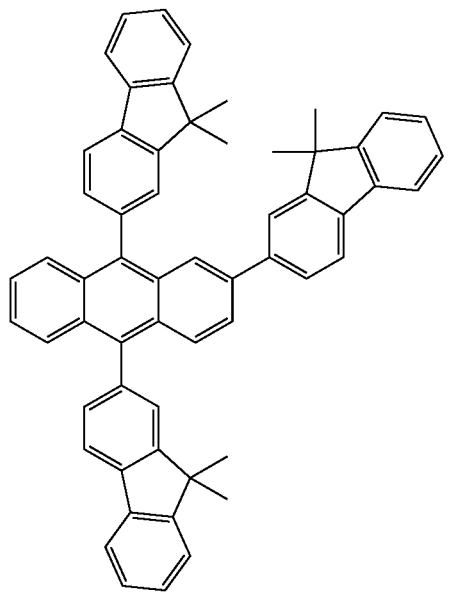
H37
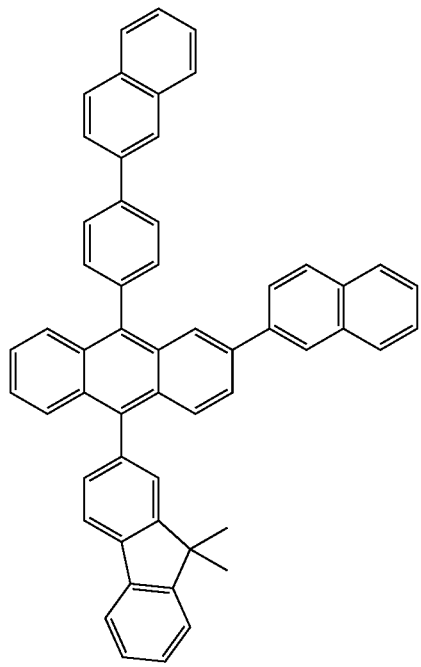
H38
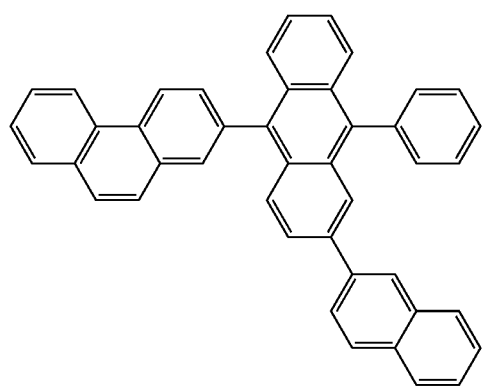
-continued
H39
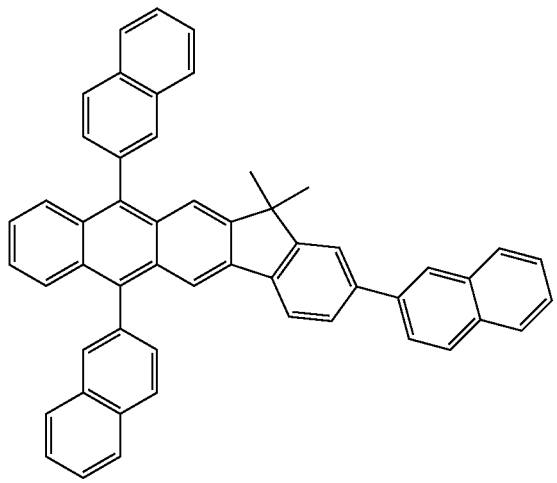
H40
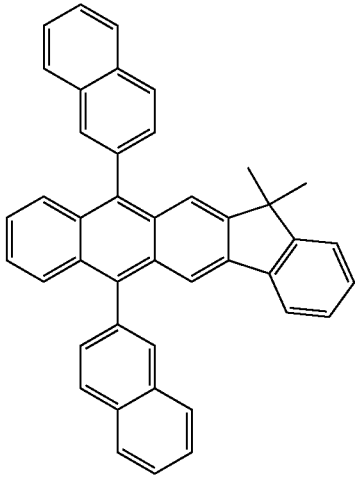
H41
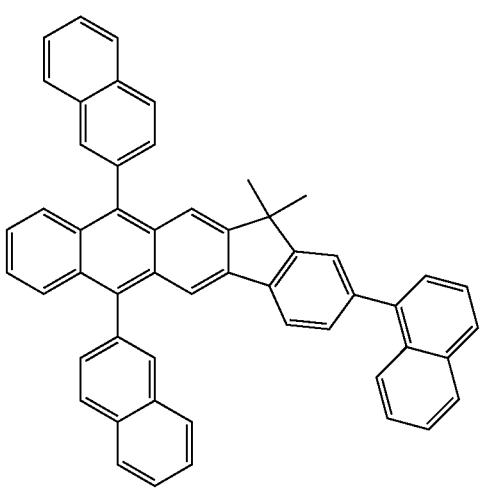

H42
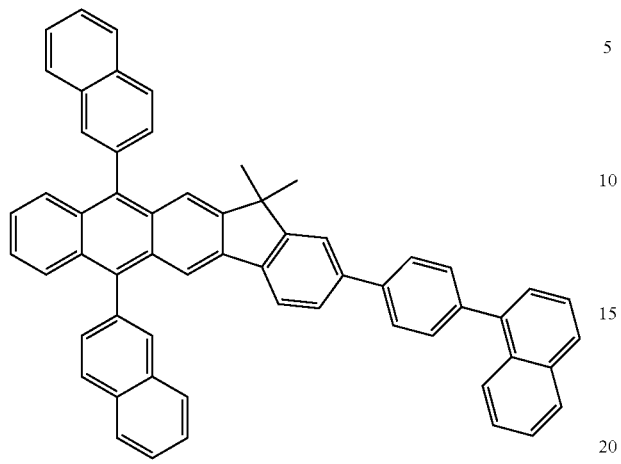
In some embodiments, the host may include at least one of Compounds H43 to H49 below:
H43
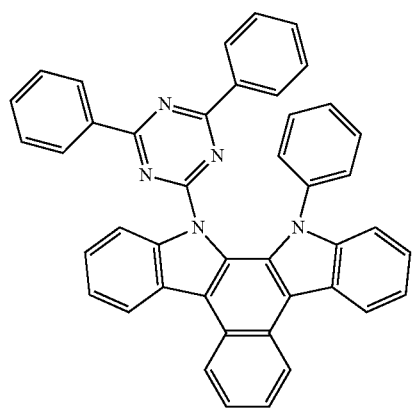
H44
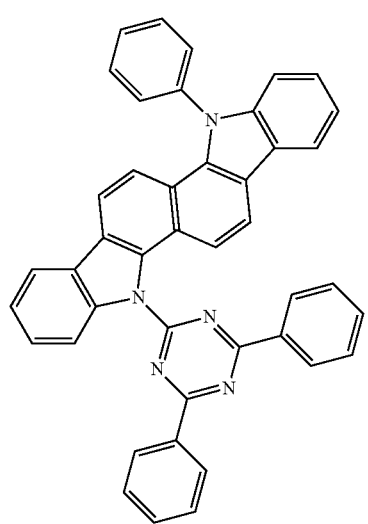
H45
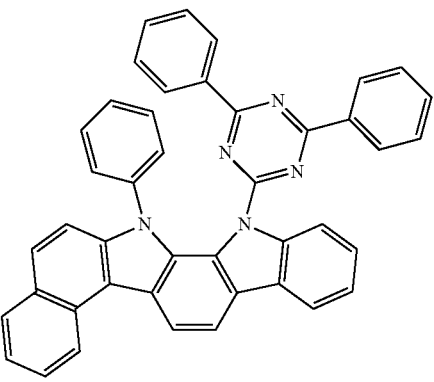
H46
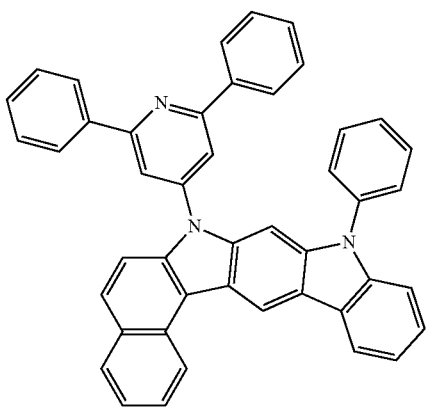
H47
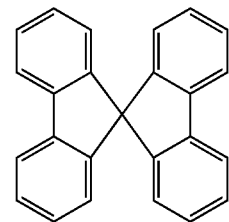
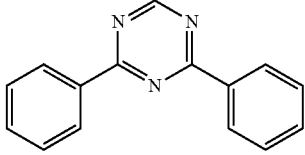
H48
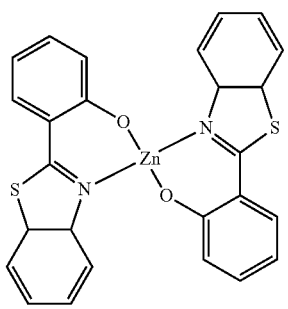

H49

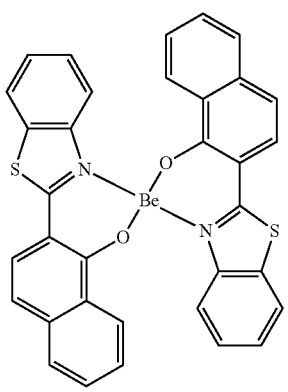

The dopant may include at least one selected from a fluorescent dopant and a phosphorescent dopant.

For example, the phosphorescent dopant may include an organometallic compound including one selected from iridium (Ir), platinum (Pt), osmium (Os), titanium (Ti), zirconium (Zr), hafnium (Hf), europium (Eu), terbium (Tb), thulium (Tm), rhodium (Rh), and copper (Cu);

In some embodiments, the phosphorescent dopant may include an organometallic complex represented by Formula 401 below:

<Formula 401>

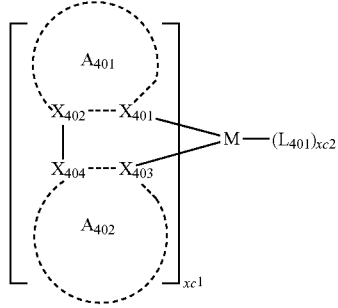

In Formula 401,

M may be selected from iridium (Ir), platinum (Pt), osmium (Os), titanium (Ti), zirconium (Zr), hafnium (Hf), europium (Eu), terbium (Tb), and thulium (TM);

$X_{401}$ to $X_{404}$ may each independently be nitrogen or carbon;

rings $A_{401}$ and $A_{402}$ may each independently be selected from a substituted or unsubstituted benzene, a substituted or unsubstituted naphthalene, a substituted or unsubstituted fluorenene, a substituted or unsubstituted spiro-fluorenene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazol, a substituted or unsubstituted benzoimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene; and at least one substituent of the substituted benzene, substituted naphthalene, substituted fluorenene, substituted spiro-fluorenene, substituted indene, substituted pyrrole, substituted thiophene, substituted furan, substituted imidazole, substituted pyrazole, substituted thiazole, substituted isothiazole, substituted oxazole, substituted isoxazole, substituted pyridine, substituted pyrazine, substituted pyrimidine, substituted pyridazine, substituted quinoline, substituted isoquinoline, substituted benzoquinoline, substituted quinoxaline, substituted quinazoline, substituted carbazol, substituted benzoimidazole, substituted benzofuran, substituted benzothiophene, substituted isobenzothiophene, substituted benzoxazole, substituted isobenzoxazole, substituted triazole, substituted oxadiazole, substituted triazine, substituted dibenzofuran, and substituted dibenzothiophene may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{401}$)($Q_{402}$), —Si($Q_{403}$)($Q_{404}$)($Q_{405}$), or —B($Q_{406}$)($Q_{407}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic heterocondensed polycyclic group, —N($Q_{411}$)($Q_{412}$), —Si($Q_{413}$)($Q_{414}$)($Q_{415}$), and —B($Q_{416}$)($Q_{417}$); and —N($Q_{421}$)($Q_{422}$), Si($Q_{423}$)($Q_{424}$)($Q_{425}$), and —B($Q_{426}$)($Q_{427}$), $L_{401}$ is an organic ligand;

xc1 is 1, 2, or 3; and xc2 is 0, 1, 2, or 3.

Descriptions of $Q_{401}$ to $Q_{407}$, $Q_{411}$ to $Q_{417}$, and $Q_{421}$ to $Q_{427}$ may be understood by referring to the description provided in connection with $Q_1$.

$L_{401}$ may be a monovalent, divalent, or trivalent organic ligand. For example, $L_{401}$ may be selected from a halogen ligand (for example, Cl or F), a diketone ligand (for example, acetylacetonate, 1,3-diphenyl-1,3-propandionate, 2,2,6,6-tetramethyl-3,5-heptandionate, or hexafluoroacetonate), a carboxylic acid ligand (for example, picolinate, dimethyl-3-pyrazolecarboxylate, or benzoate), a carbon monooxide ligand, an isonitrile ligand, a cyano ligand, and a phosphorous ligand (for example, phosphine, and phosphaite).

When $A_{401}$ in Formula 401 has two or more substituents, the substituents of $A_{401}$ may bind to each other to form a saturated or unsaturated ring.

When $A_{402}$ in Formula 402 has two or more substituents, the substituents of $A_{402}$ may bind to each other to form a saturated or unsaturated ring.

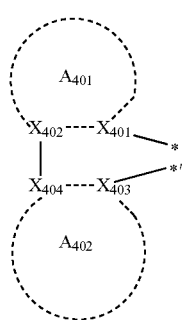

When xc1 in Formula 401 is two or more, a plurality of ligands in Formula 401 may be identical or different. When xc1 in Formula 401 is two or more, $A_{401}$ and $A_{402}$ may be respectively directly connected to $A_{401}$ and $A_{402}$ of other neighboring ligands with or without a linker (for example, a $C_1$-$C_5$ alkylene, or —N(R')— (wherein R' may be a $C_1$-$C_{10}$ alkyl group or a $C_6$-$C_{20}$ aryl group) or —C(=O)—) therebetween.

The phosphorescent dopant may include at least one of Compounds PD1 to PD74 below:

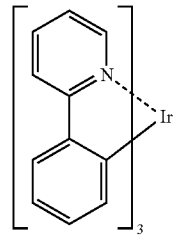

PD1

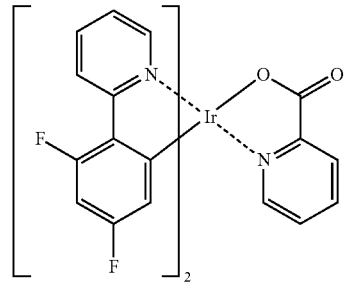

PD2

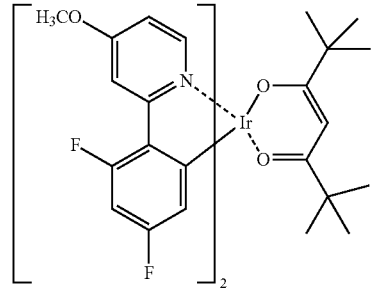

PD3

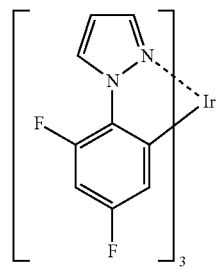

PD4

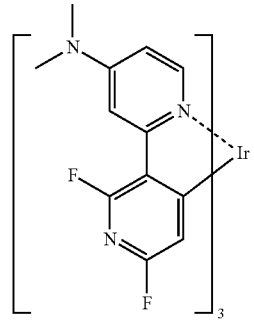

PD5

-continued
PD6
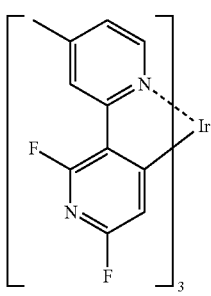
PD7
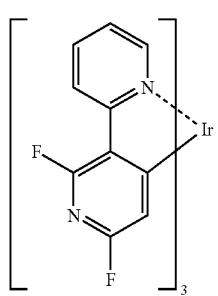
PD8
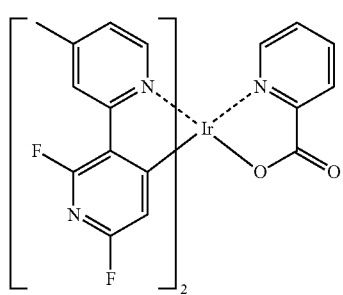
PD9
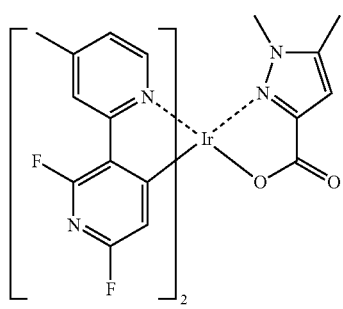
PD10
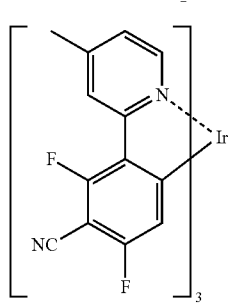
-continued
PD11
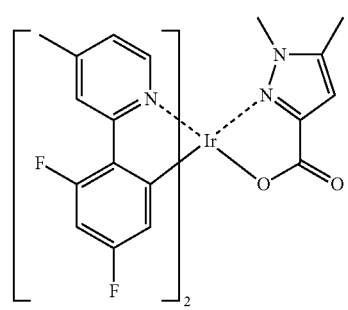
PD12
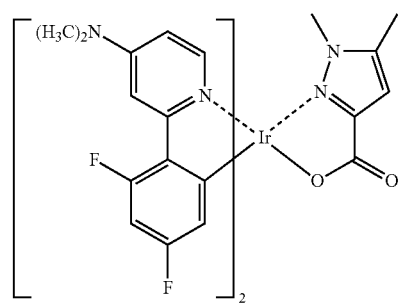
PD13
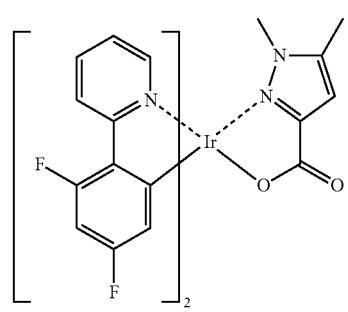
PD14
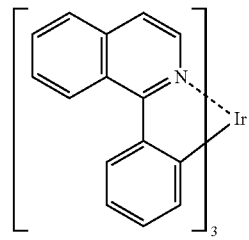
PD15
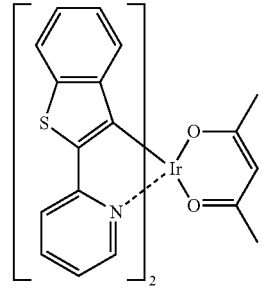

PD16 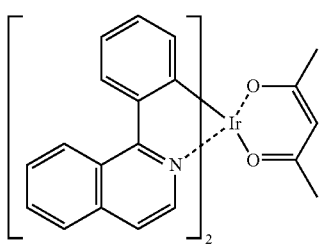
PD17 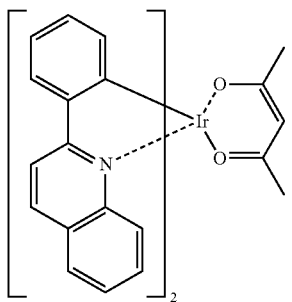
PD18 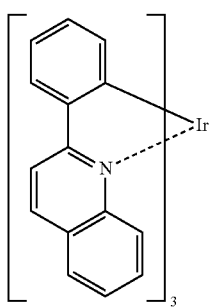
PD19 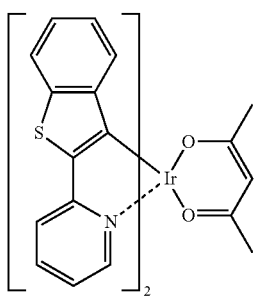
PD20 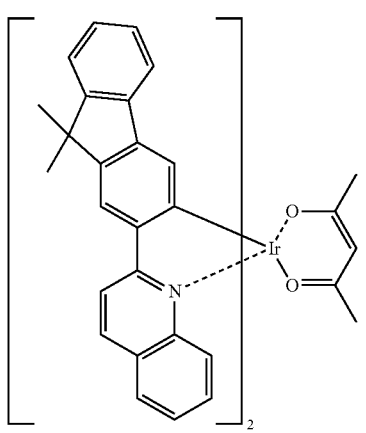
PD21 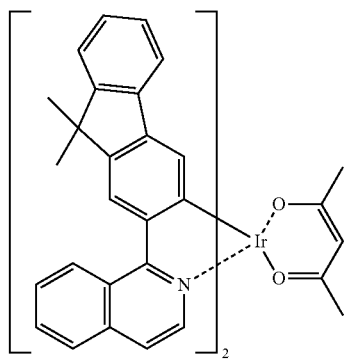
PD22 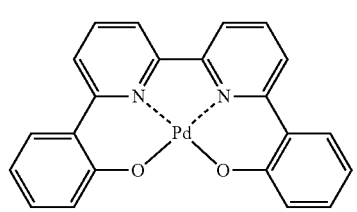
PD23 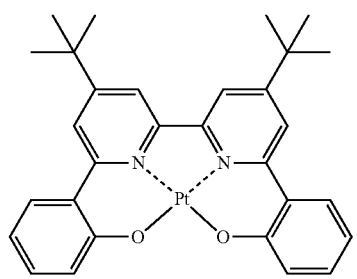
PD24 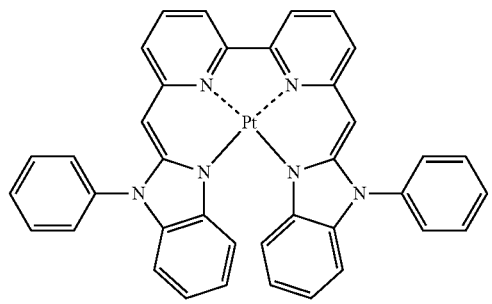
PD25 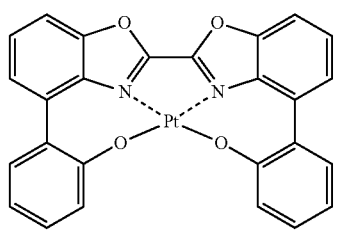
PD26 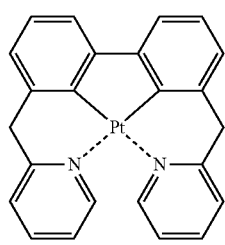

-continued
PD27 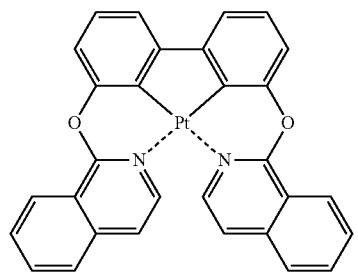
PD28 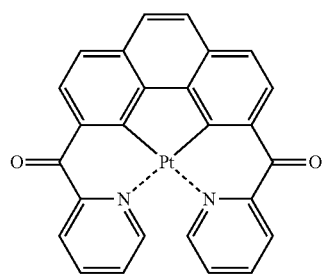
PD29 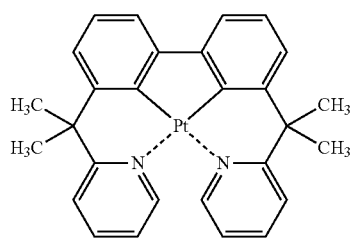
PD30 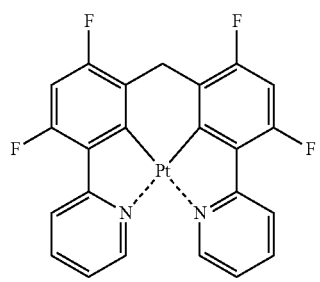
PD31 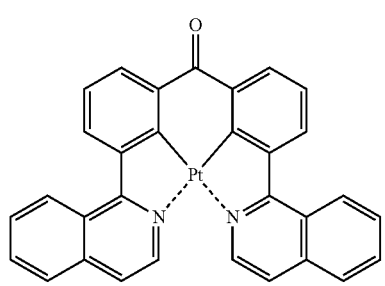
PD32 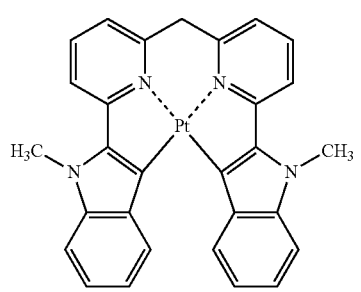
-continued
PD33 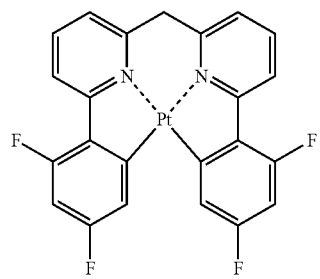
PD34 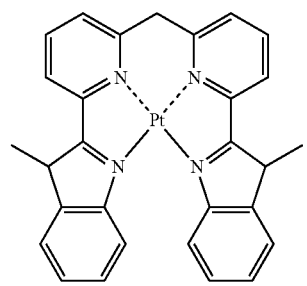
PD35 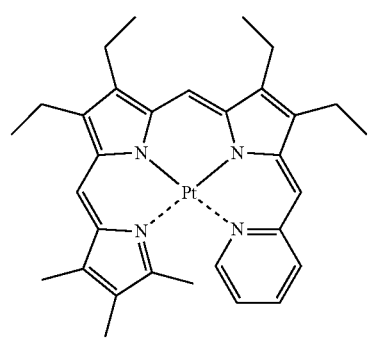
PD36 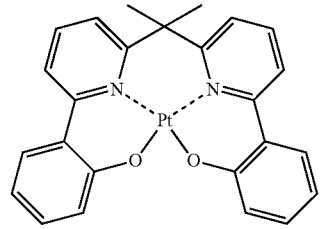
PD37 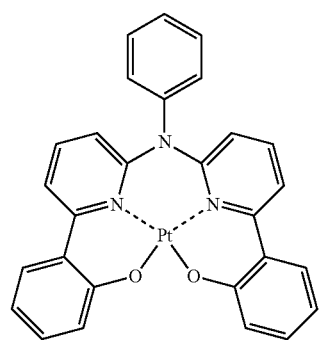

PD38 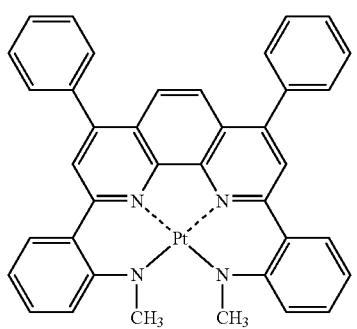
PD39 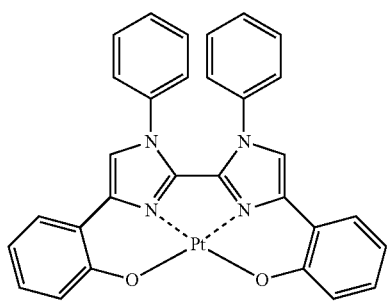
PD40 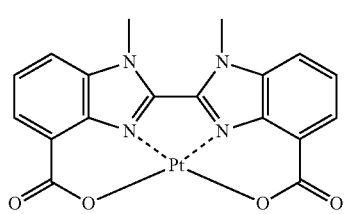
PD41 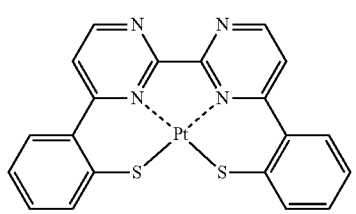
PD42 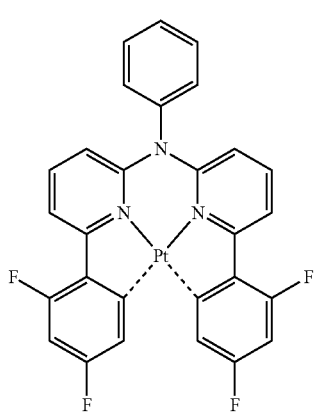
PD43 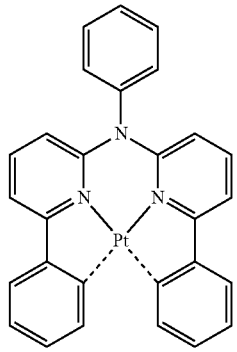
PD44 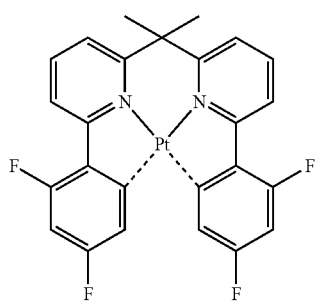
PD45 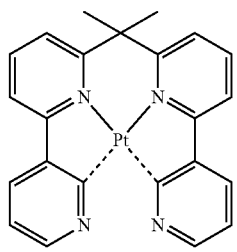
PD46 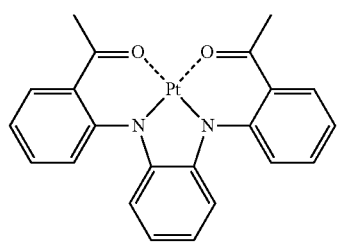
PD47 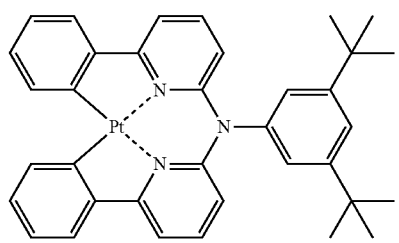
PD48 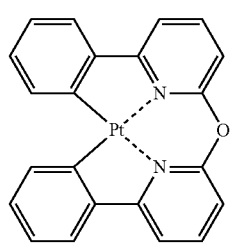

PD49 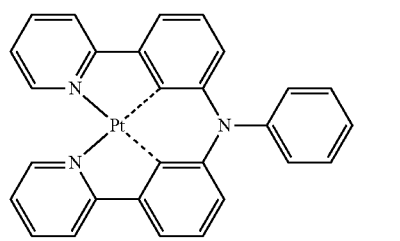
PD50 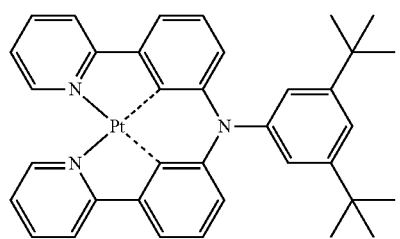
PD51 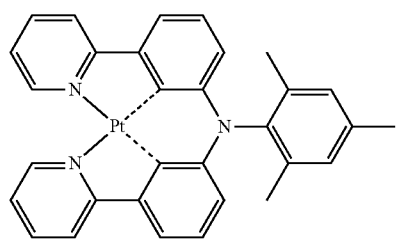
PD52 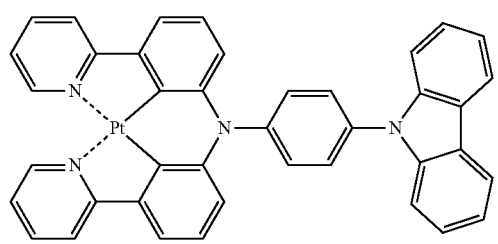
PD53 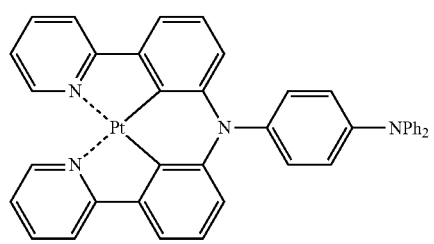
PD54 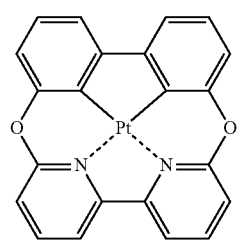
PD55 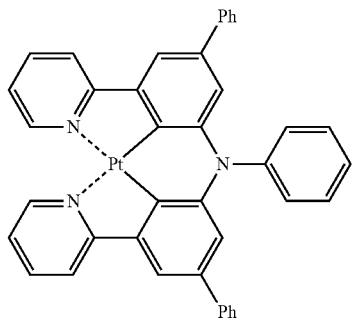
PD56 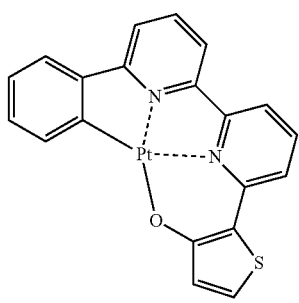
PD57 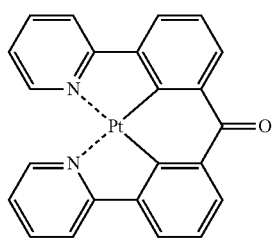
PD58 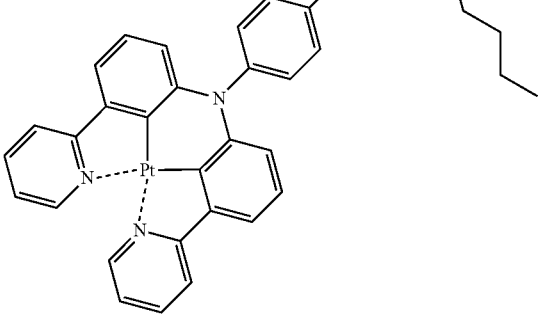
PD59 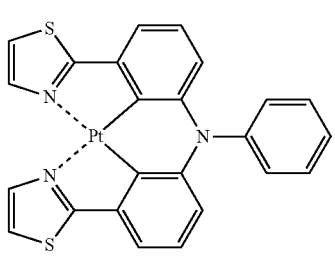

PD60
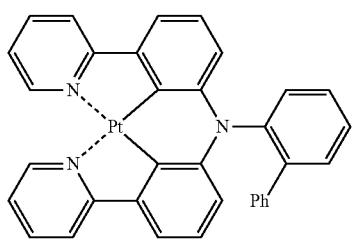
PD61
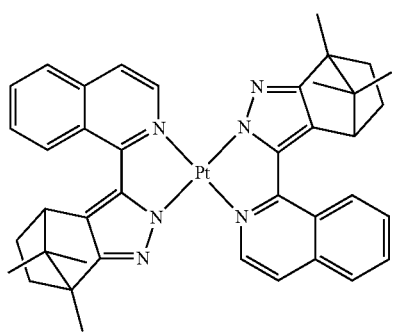
PD62
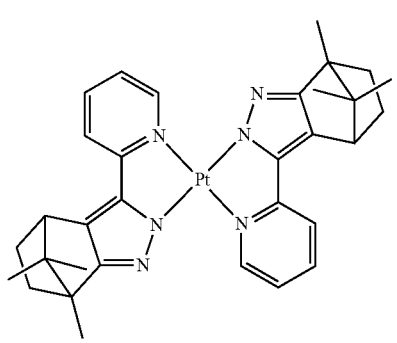
PD63
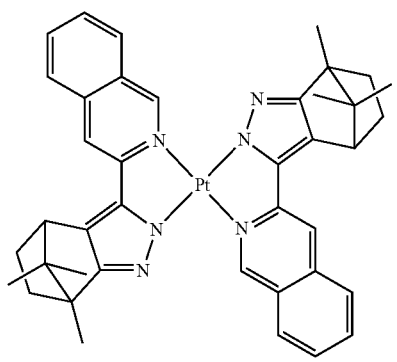
PD64
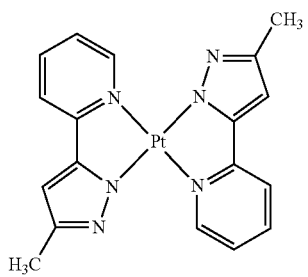
PD65
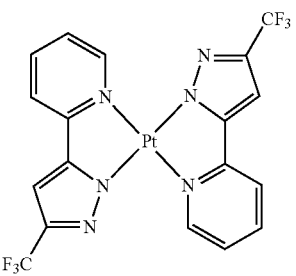
PD66
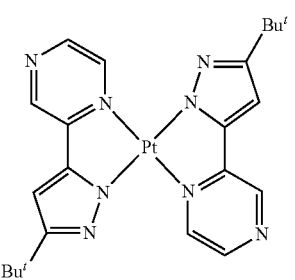
PD67
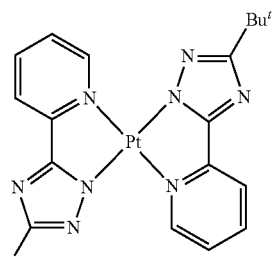
PD68
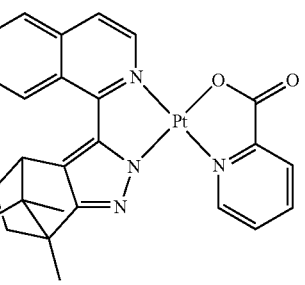
PD69
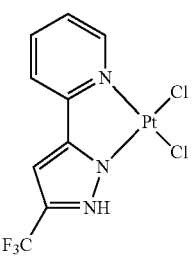

-continued
PD70 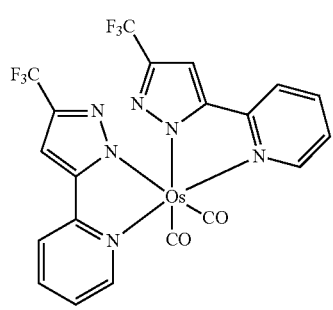
PD71 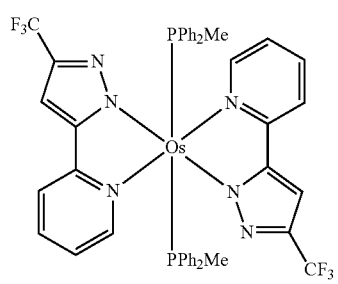
PD72 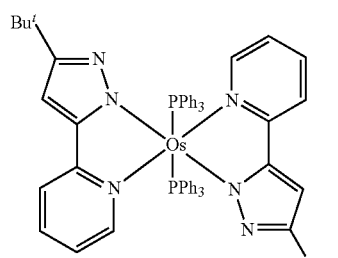
PD73 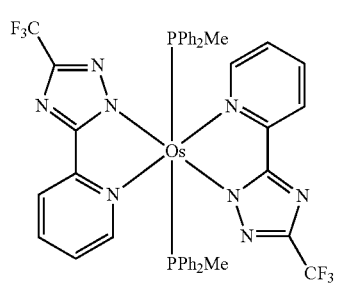
-continued
PD74 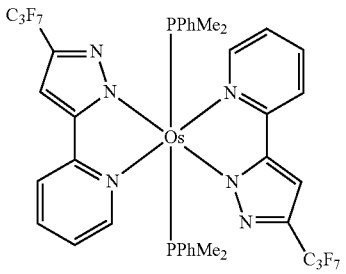
In some embodiments, the phosphorescent dopant may include PtOEP:
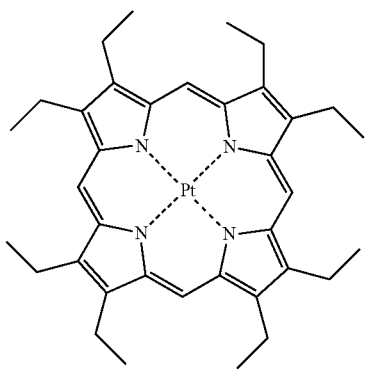
PtOEP
The fluorescent dopant may include at least one selected from DPAVBi, BDAVBi, TBPe, DCM, DCJTB, Coumarin 6, and C545T.
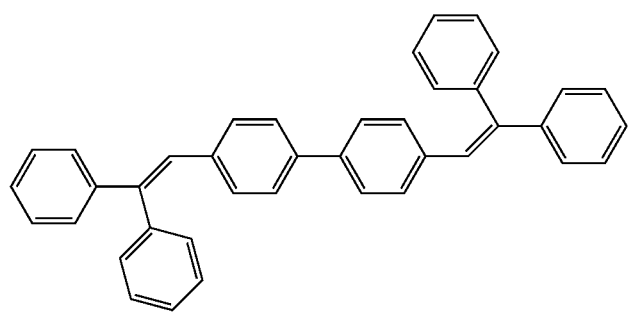
DPVBi -continued

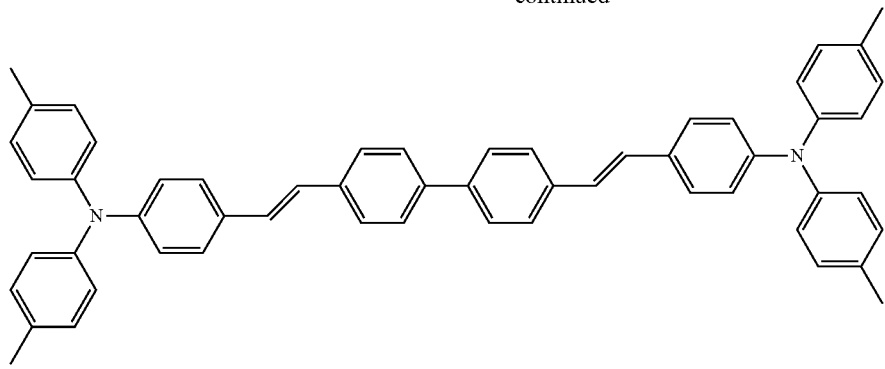
DPAVBi

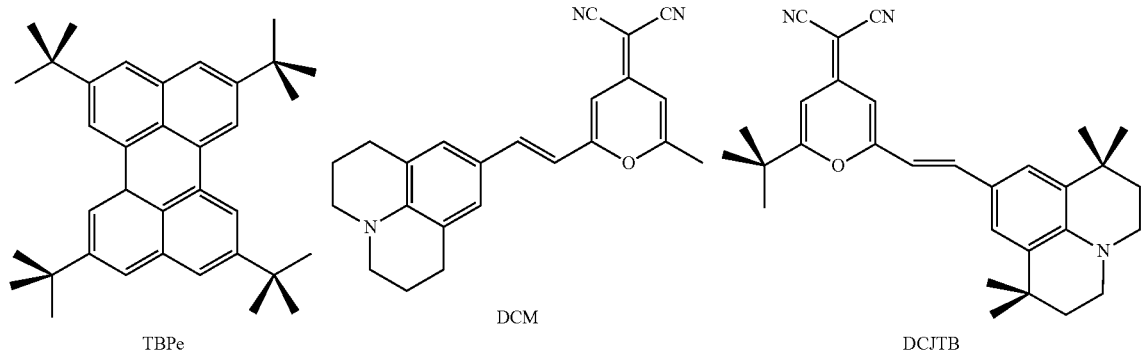
TBPe  DCM  DCJTB

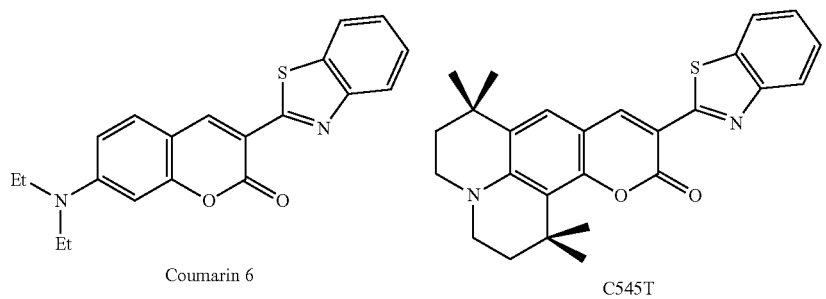
Coumarin 6  C545T

In some embodiments, the fluorescent dopant may include a compound represented by Formula 501 below.

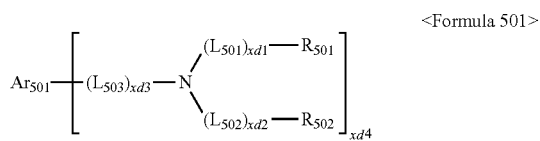
<Formula 501>

In Formula 501, $Ar_{501}$ may be selected from a naphthalene, a heptalene, a fluorene, a spiro-fluorenene, a benzofluorenene, a dibenzofluorenene, a phenalene, a phenanthrene, an anthracene, a fluoranthene, a triphenylene, a pyrene, a chrysene, a naphthacene, a picene, a perylene, a pentaphene, and an indenoanthracene; and a naphthalene group, a heptalene group, a fluorenene group, a spiro-fluorenene group, a benzofluorenene group, a dibenzofluorenene group, a phenalene group, a phenanthrene group, a anthracene group, a fluoranthene group, a triphenylene group, a pyrene group, a chrysene group, a naphthacene group, a picene group, a perylene group, a pentaphene group, and an indenoanthracene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{501}$)($Q_{502}$)($Q_{503}$) (wherein $Q_{501}$ to $Q_{503}$ are each independently selected from a hydrogen, a $C_1$-$C_{60}$ alkyl group, a $C_2$-$C_{60}$ alkenyl group, a $C_2$-$C_{60}$ aryl group, and a $C_1$-$C_{60}$ heteroaryl group);

descriptions of $L_{501}$ to $L_{503}$ are the same as defined in connection with $L_{201}$;

$R_{501}$ and $R_{502}$ may each independently be selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group;

xd1 to xd3 may each independently be selected from 0, 1, 2, and 3; and xd4 may be selected from 1, 2, 3, and 4.

The fluorescent dopant may include at least one of (Compounds FD1 to FD9:

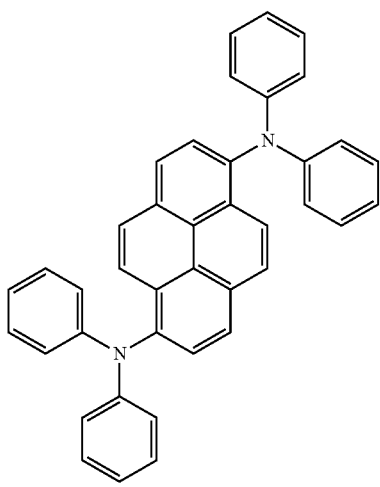

FD1

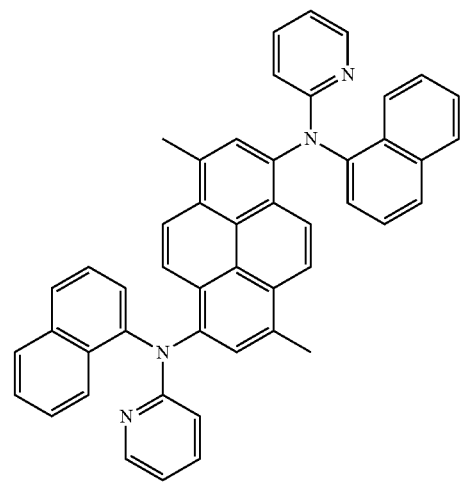

FD2

-continued

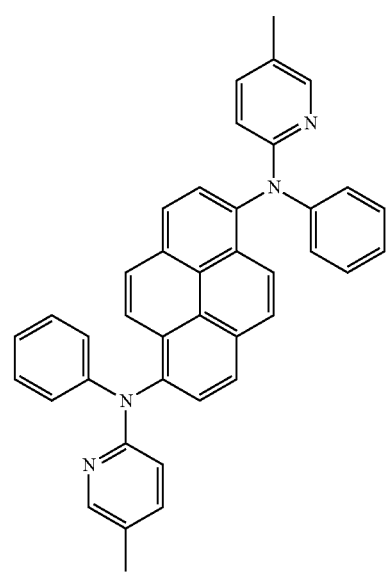

FD3

FD4
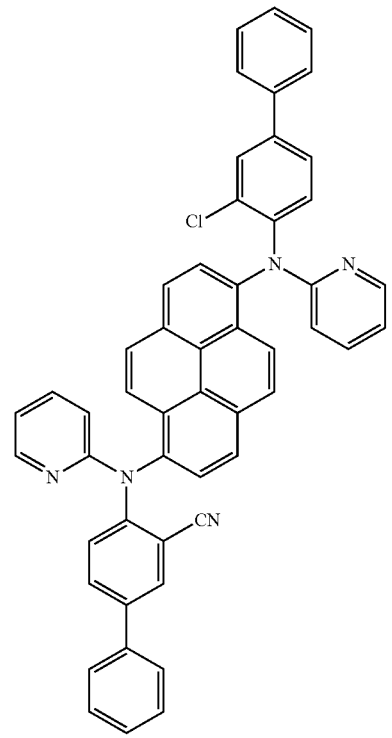
FD6
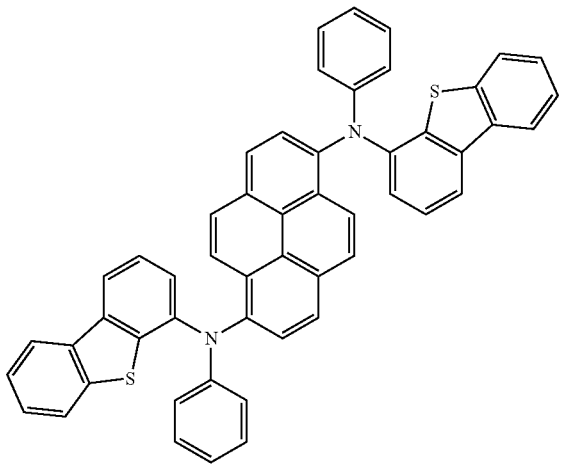
FD7
FD8
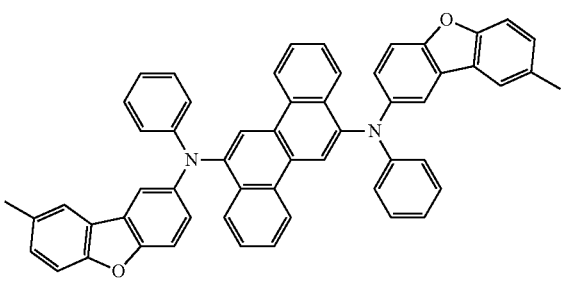
FD5
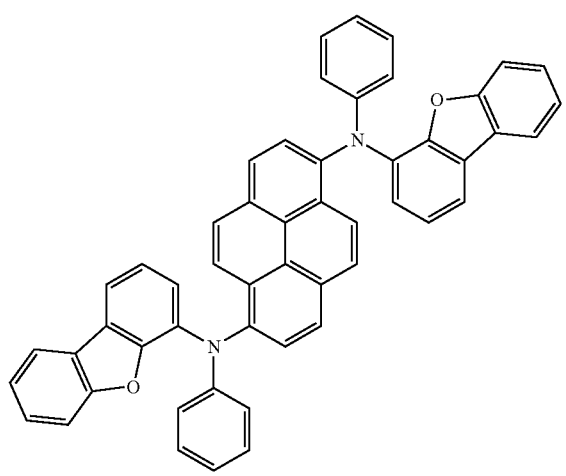
FD9
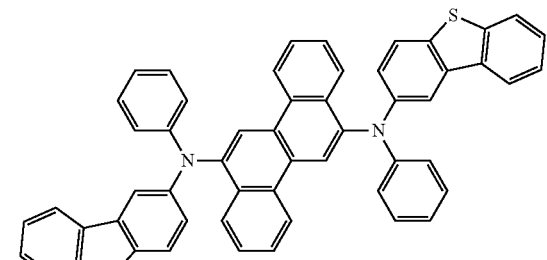
An amount of the dopant in the emission layer may be, e.g., in a range of about 0.01 to about 15 parts by weight based on 100 parts by weight of the host.

A thickness of the emission layer may be in a range of about 100 Å to about 1000 Å, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer (ETL), and an electron injection layer.

For example, the electron transport region may have a structure of electron transport layer/electron injection layer or a structure of hole blocking layer/electron transport layer/electron injection layer, wherein layers of each structure are sequentially stacked from the emission layer in the stated order.

According to an embodiment, the organic layer 150 of the organic light-emitting device may include an electron transport region disposed between the emission layer and the second electrode 190.

When the electron transport region includes a hole blocking layer, the hole blocking layer may be formed on the emission layer by using various methods, such as vacuum deposition, spin coating casting, a LB method, ink-jet printing, laser-printing, or laser-induced thermal imaging. When the hole blocking layer is formed by vacuum deposition or spin coating, deposition and coating conditions for the hole blocking layer may be determined by referring to the deposition and coating conditions for the hole injection layer.

The hole blocking layer may include, for example, at least one of BCP and Bphen.

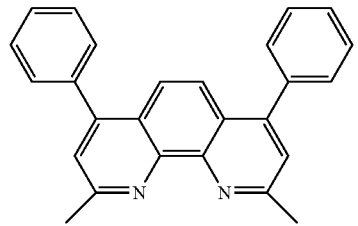

BCP

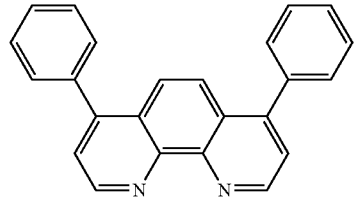

Bphen

A thickness of the hole blocking layer may be in a range of about 20 Å to about 1,000 Å, for example, about 30 Å to about 300 Å. When the thickness of the hole blocking layer is within these ranges, the hole blocking layer may have improved hole blocking ability without a substantial increase in driving voltage.

The electron transport region may include an electron transport layer. The electron transport layer may be formed on the emission layer or the hole blocking layer by using various methods, such as vacuum deposition, spin coating casting, a LB method, ink-jet printing, laser-printing, or laser-induced thermal imaging. When an electron transport layer is formed by vacuum deposition or spin coating, deposition and coating conditions for the electron transport layer may be determined by referring to the deposition and coating conditions for the hole injection layer.

In some embodiments, the electron transport layer may include at least one compound selected from a compound represented by Formula 601 and a compound represented by Formula 602 illustrated below:

$$Ar_{601}\text{-}[(L_{601})_{xe1}\text{-}E_{601}]_{xe2} \qquad \text{<Formula 601>}$$

In Formula 601, $Ar_{601}$ may be selected from a naphthalene, a heptalene, a fluorenene, a spiro-fluorenene, a benzofluorenene, a dibenzofluorenene, a phenalene, a phenanthrene, an anthracene, a fluoranthene, a triphenylene, a pyrene, a chrysene, a naphthacene, a picene, a perylene, a pentaphene, and an indenoanthracene;

a naphthalene group, a heptalene group, a fluorenene group, a spiro-fluorenene group, a benzofluorenene group, a dibenzofluorenene group, a phenalene group, a phenanthrene group, a anthracene group, a fluoranthene group, a triphenylene group, a pyrene group, a chrysene group, a naphthacene group, a picene group, a perylene group, a pentaphene group, and an indenoanthracene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$) (wherein $Q_{301}$ to $Q_{303}$ are each independently selected from a hydrogen, a $C_1$-$C_{60}$ alkyl group, a $C_2$-$C_{60}$ alkenyl group, a $C_2$-$C_{60}$ aryl group, and a $C_1$-$C_{60}$ heteroaryl group);

$L_{601}$ may be the same as explained in connection with $L_{201}$;

$E_{601}$ may be selected from a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

xe1 may be selected from 0, 1, 2, and 3; and
xe2 may be selected from 1, 2, 3, and 4.

<Formula 602>

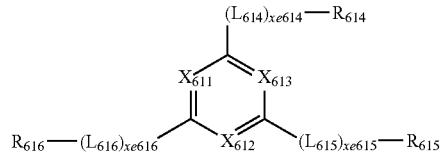

In Formula 602,
$X_{611}$ may be N or C-$(L_{611})_{xe611}$-$R_{611}$, $X_{612}$ may be N or C-$(L_{612})_{xe612}$-$R_{612}$, $X_{613}$ may be N or C-$(L_{613})_{xe613}$-$R_{613}$, and at least one of $X_{611}$ to $X_{613}$ may be N;

$L_{611}$ to $L_{616}$ may be the same as explained in connection with $L_1$;

$R_{611}$ to $R_{616}$ may each independently be selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xe611 to xe616 may each independently be selected from 0, 1, 2, and 3.

The compound represented by Formula 601 and the compound represented by Formula 602 may include Compounds ET1 to ET15 illustrated below:

ET1

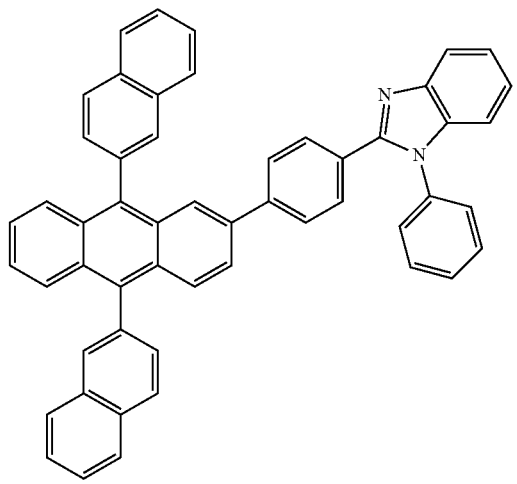

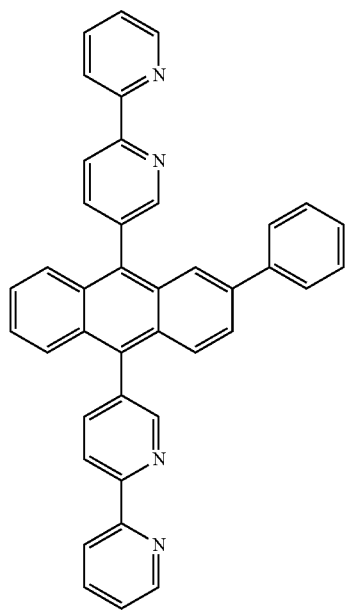
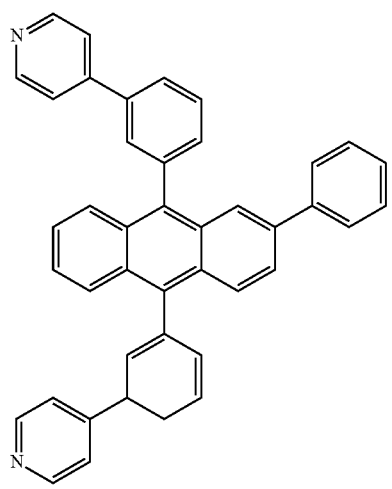
ET3
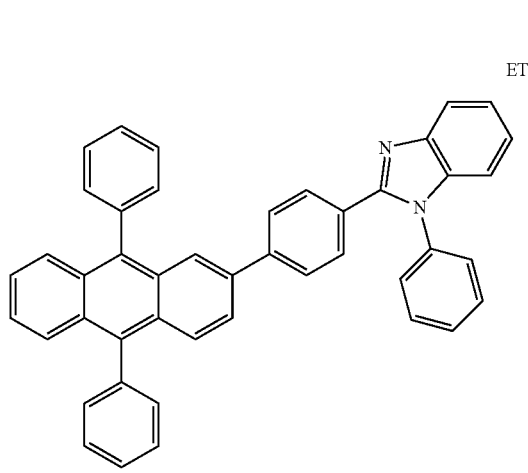
ET4
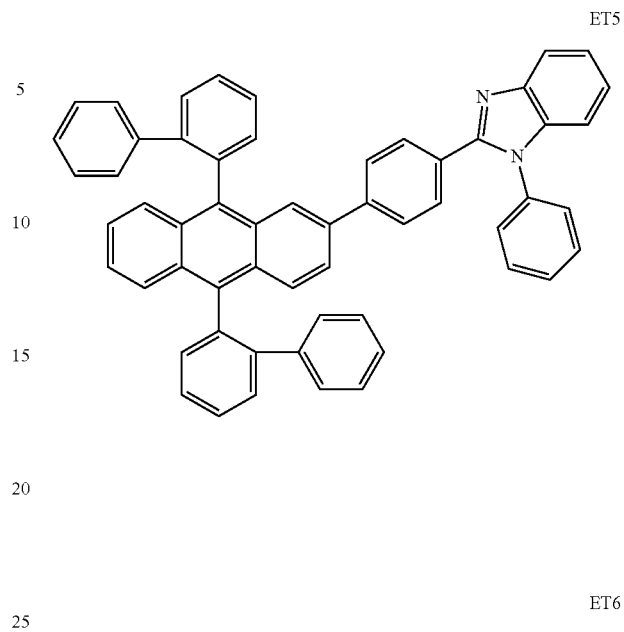
ET2
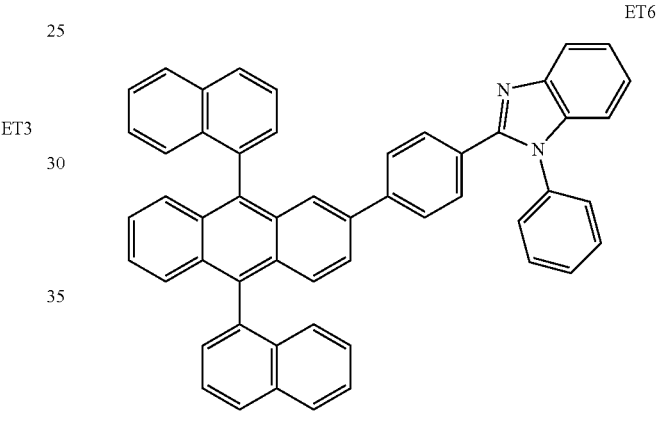
ET5
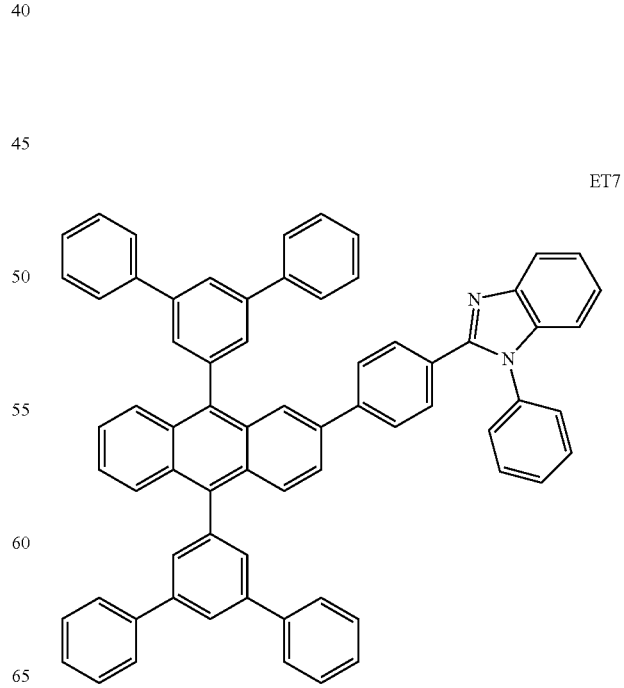
ET6
ET7

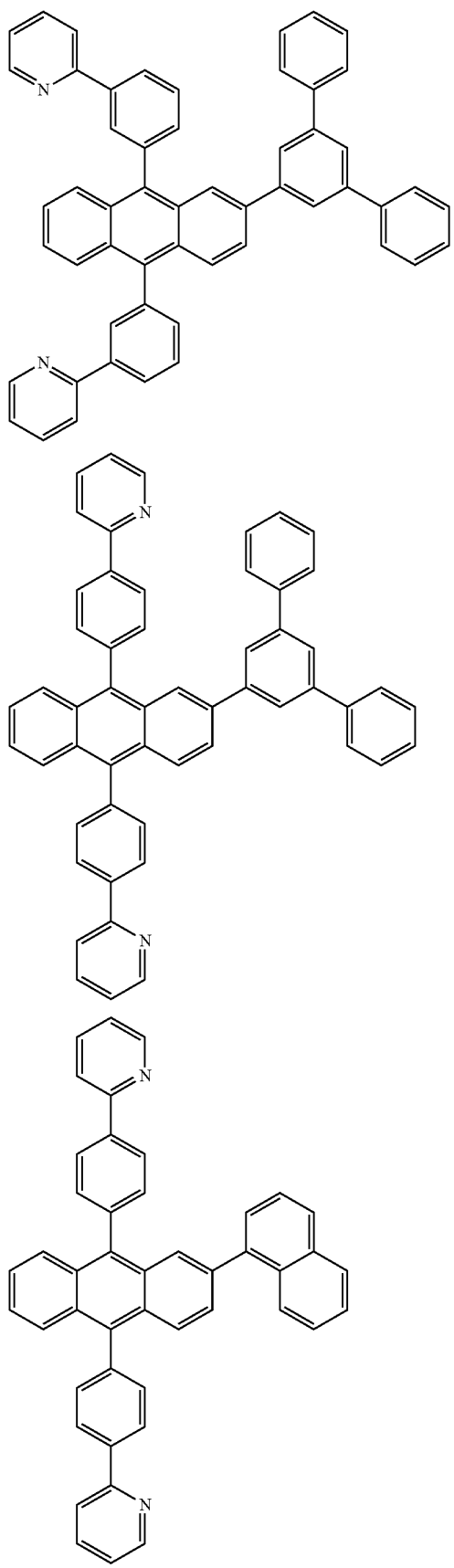
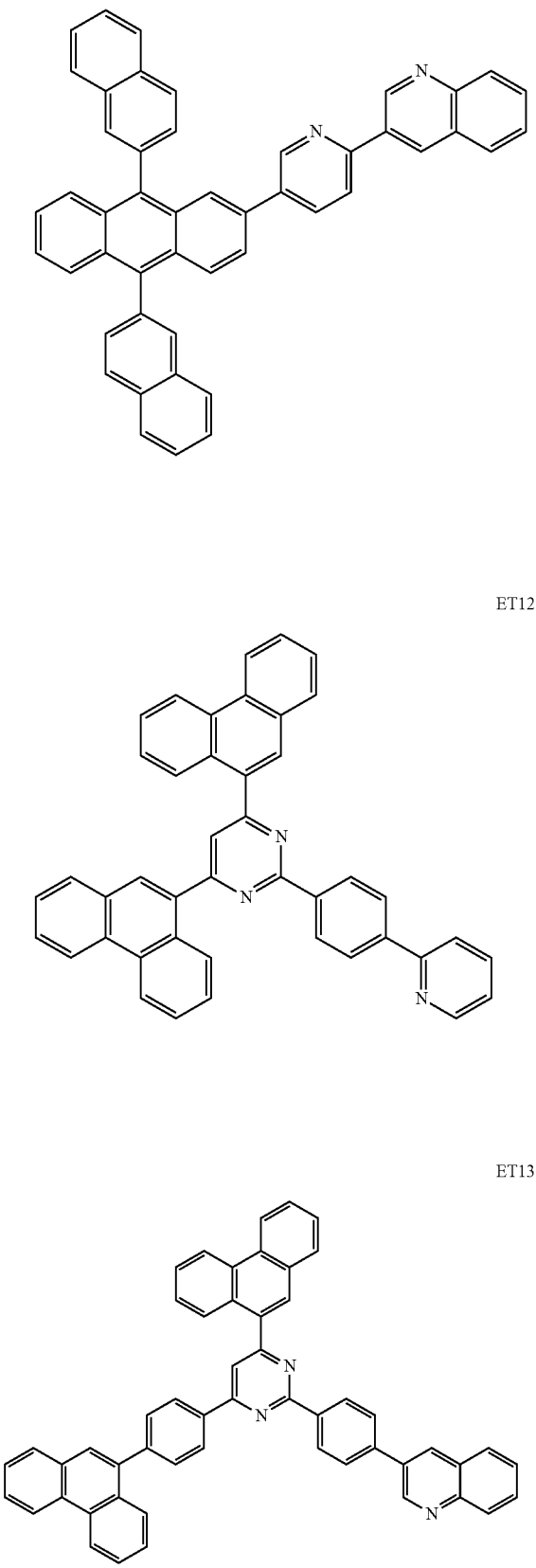

-continued

ET14

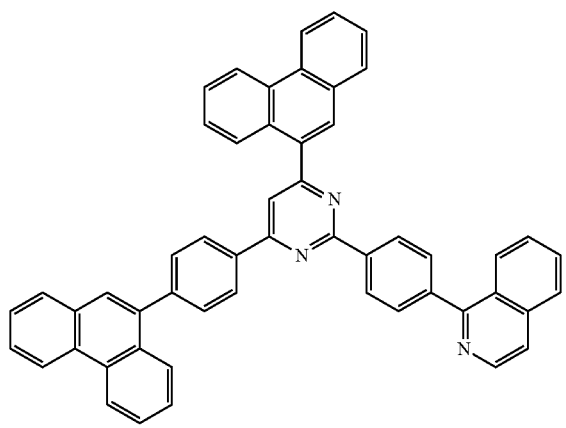

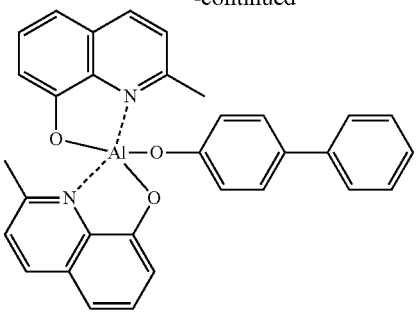

BAlq

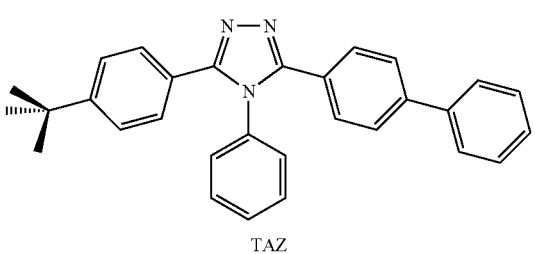

TAZ

ET15

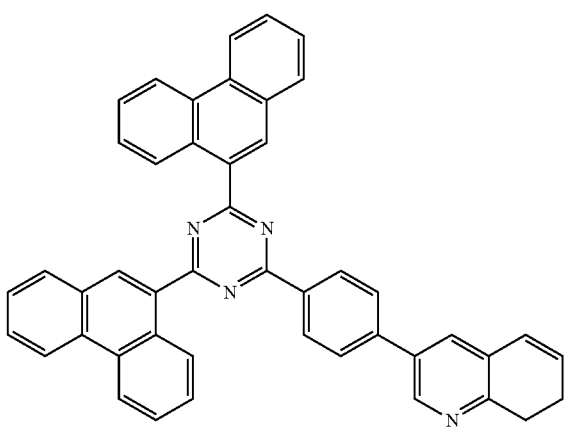

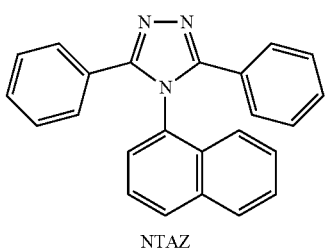

NTAZ

In some embodiments, the electron transport layer may further include at least one selected from BCP, Bphen, Alq$_3$, Balq, TAZ, and NTAZ.

A thickness of the electron transport layer may be in a range of about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, e.g., Compound ET-D1 (lithium quinolate, LiQ) or ET-D2.

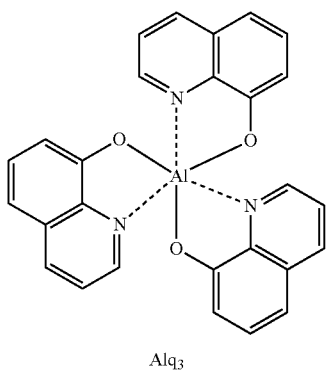

Alq$_3$

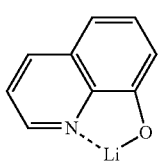

ET-D1

ET-D2

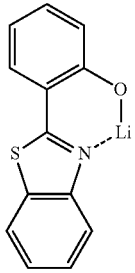

The electron transport region may include an electron injection layer that facilitates the injection of electrons from the second electrode 190.

The electron injection layer may be formed on the electron transport layer by using various methods, such as vacuum deposition, spin coating casting, a LB method, ink-jet printing, laser-printing, or laser-induced thermal imaging. When an electron injection layer is formed by vacuum deposition or spin coating, deposition and coating conditions for the electron injection layer may be determined by referring to the deposition and coating conditions for the hole injection layer.

The electron injection layer may include at least one selected from, LiF, NaCl, CsF, $Li_2O$, BaO, and LiQ.

A thickness of the electron injection layer may be in a range of about 1 Å to about 100 Å, about 3 Å to about 90 Å. When the thickness of the electron injection layer is within the range described above, the electron injection layer may have satisfactory electron injection characteristics without a substantial increase in driving voltage.

The second electrode 190 may be disposed on the organic layer 150 having such a structure. The second electrode 190 may be a cathode that is an electron injection electrode, and in this regard, a material for forming the second electrode 190 may include a material having a low work function, and such a material may include a metal, alloy, an electrically conductive compound, or a mixture thereof. Examples of the material for the second electrode 190 may include lithium (Li), magnesium (Mg), aluminum (Al), aluminum-lithium (Al— Li), calcium (Ca), magnesium-indium (Mg—In), or magnesium-silver (Mg—Ag). In some embodiments, the material for forming the second electrode 190 may include ITO or IZO. The second electrode 190 may be a semi-transmissive electrode or a transmissive electrode.

Hereinbefore, the organic light-emitting device has been described with reference to FIG. 1.

A $C_1$-$C_{60}$ alkyl group used herein refers to a linear or branched aliphatic hydrocarbon monovalent group having 1 to 60 carbon atoms, and detailed examples thereof are a methyl group, an ethyl group, a propyl group, an isobutyl group, a sec-butyl group, a ter-butyl group, a pentyl group, an iso-amyl group, and a hexyl group. A $C_1$-$C_{60}$ alkylene group used herein refers to a divalent group having the same structure as the $C_1$-$C_{60}$ alkyl group.

A $C_1$-$C_{60}$ alkoxy group used herein refers to a monovalent group represented by —$OA_{101}$ (wherein $A_{101}$ is the $C_1$-$C_{60}$ alkyl group), and detailed examples thereof are a methoxy group, an ethoxy group, and an isopropyloxy group.

A $C_2$-$C_{60}$ alkenyl group used herein refers to a hydrocarbon group formed by substituting at least one carbon double bond in the middle or at the terminal of the $C_2$-$C_{60}$ alkyl group, and detailed examples thereof are an ethenyl group, a prophenyl group, and a butenyl group. A $C_2$-$C_{60}$ alkylene group used herein refers to a divalent group having the same structure as the $C_2$-$C_{60}$ alkyl group.

A $C_2$-$C_{60}$ alkynyl group used herein refers to a hydrocarbon group formed by substituting at least one carbon trip bond in the middle or at the terminal of the $C_2$-$C_{60}$ alkyl group, and detailed examples thereof are an ethynyl group, and a propynyl group. A $C_2$-$C_{60}$ alkylene group used herein refers to a divalent group having the same structure as the $C_2$-$C_{60}$ alkyl group.

A $C_3$-$C_{10}$ cycloalkyl group used herein refers to a monovalent hydrocarbon monocyclic group having 3 to 10 carbon atoms, and detailed examples thereof are a cyclopropyl group, a cyclobutyl group, a cyclopentyl group, a cyclohexyl group, and a cycloheptyl group. A $C_3$-$C_{10}$ cycloalkylene group used herein refers to a divalent group having the same structure as the $C_3$-$C_{10}$ cycloalkyl group.

A $C_1$-$C_{10}$ heterocycloalkyl group used herein refers to a monovalent monocyclic group having at least one hetero atom selected from N, O, Si, P, and S as a ring-forming atom and 1 to 10 carbon atoms, and detailed examples thereof are a tetrahydrofuranyl group, and a tetrahydrothiophenyl group. A $C_1$-$C_{10}$ heterocycloalkylene group used herein refers to a divalent group having the same structure as the $C_1$-$C_{10}$ heterocycloalkyl group.

A $C_3$-$C_{10}$ cycloalkenyl group used herein refers to a monovalent monocyclic group that has 3 to 10 carbon atoms and at least one double bond in the ring thereof and does not have aromaticity, and detailed examples thereof are a cyclopentenyl group, a cyclohexenyl group, and a cycloheptenyl group. A $C_3$-$C_{10}$ cycloalkenylene group used herein refers to a divalent group having the same structure as the $C_3$-$C_{10}$ cycloalkenyl group.

A $C_1$-$C_{10}$ heterocycloalkenyl group used herein refers to a monovalent monocyclic group that has at least one hetero atom selected from N, O, Si, P, and S as a ring-forming atom, 1 to 10 carbon atoms, and at least one double bond in its ring. Detailed examples of the $C_1$-$C_{10}$ heterocycloalkenyl group are a 2,3-hydrofuranyl group and a 2,3-hydrothiophenyl group. A $C_1$-$C_{10}$ heterocycloalkenylene group used herein refers to a divalent group having the same structure as the $C_1$-$C_{10}$ heterocycloalkenyl group.

A $C_6$-$C_{60}$ aryl group used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_1$-$C_{60}$ heteroaryl group used herein refers to a monovalent group having a carbocyclic aromatic system that has at least one hetero atom selected from N, O, Si, P, and S as a ring-forming atom, and 1 to 60 carbon atoms. A $C_1$-$C_{60}$ heteroarylene group used herein refers to a divalent group having a carbocyclic aromatic system that has at least one hetero atom selected from N, O, P, and S as a ring-forming atom, and 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

A $C_6$-$C_{60}$ aryloxy group used herein indicates —$OA_{102}$ (wherein $A_{102}$ is the $C_6$-$C_{60}$ aryl group), and a $C_6$-$C_{60}$ arylthio group used herein indicates —$SA_{103}$ (wherein $A_{103}$ is the $C_6$-$C_{60}$ aryl group).

A monovalent non-aromatic condensed polycyclic group used herein refers to a monovalent group (for example, having 8 to 60 carbon atoms) that has two or more rings condensed to each other, only carbon atoms as a ring forming atom, and non-aromacity in the entire molecular structure. A detailed example of the monovalent non-aromatic condensed polycyclic group is a fluorenyl group. A divalent non-aromatic condensed polycyclic group used herein refers to a divalent group having the same structure as the monovalent non-aromatic condensed polycyclic group.

A monovalent non-aromatic condensed heteropolycyclic group used herein refers to a monovalent group (for example, having 2 to 60 carbon atoms) that has two or more rings condensed to each other, has a heteroatom selected from N, O, Si, P, and S, other than carbon atoms, as a ring forming atom, and has non-aromacity in the entire molecular structure. An example of the monovalent non-aromatic condensed heteropolycyclic group is a carbazolyl group. A divalent non-aromatic condensed heteropolycyclic group used herein refers to a divalent group having the same structure as the monovalent non-aromatic condensed heteropolycyclic group.

at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —$Si(Q_{11})(Q_{12})(Q_{13})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic heterocondensed polycyclic group, and —$Si(Q_{21})(Q_{22})(Q_{23})$; and —$Si(Q_{31})(Q_{32})(Q_{33})$, wherein $Q_1$ to $Q_3$, $Q_{11}$ to $Q_{13}$, $Q_{21}$ to $Q_{23}$, and $Q_{31}$ to $Q_{33}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

The term "Ph" used herein refers to a phenyl group, the term "Me" used herein refers to a methyl group, the term "Et" used herein refers to an ethyl group, and the term "ter-Bu" or "Bu$^t$" used herein refers to a tert-butyl group.

Hereinafter, an organic light-emitting device according to an embodiment will be described in detail with reference to Synthesis Examples and Examples. The wording "B was used instead of A" used in describing Synthesis Examples means that a molar equivalent of A is identical to a molar equivalent of B.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Example 1

Synthesis Example 1: Synthesis of Compound 3

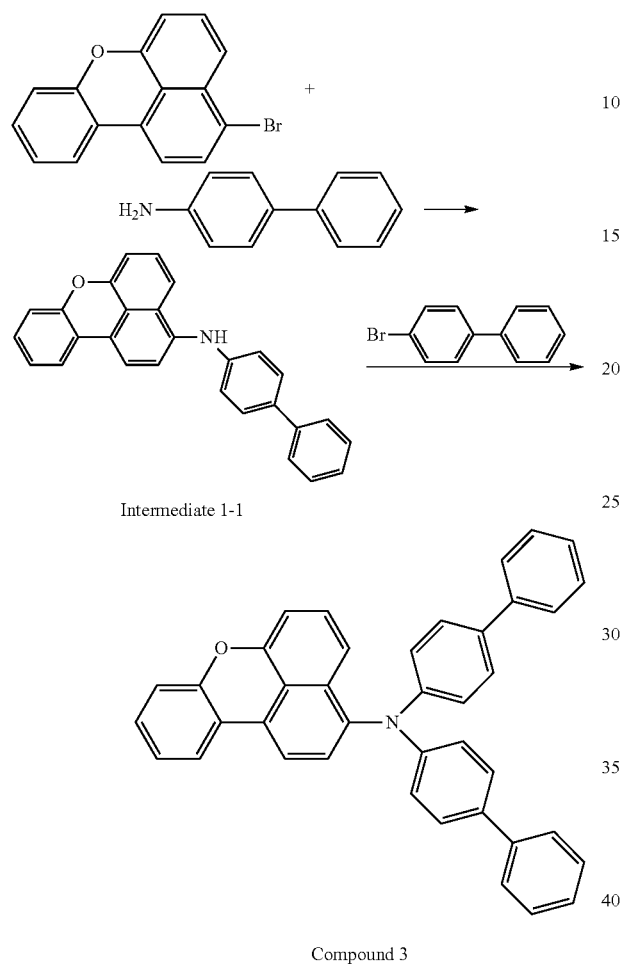

Intermediate 1-1

Compound 3

Synthesis of Intermediate 1-1

10.0 mmol (3.0 g) of 3-bromotriphenylzanthene and 12 mmol (2.0 g) of 4-aminobiphenyl were diluted in 150 ml of toluene, and then, under a nitrogen atmosphere, 0.5 mmol (0.5 g) of tris(dibenzylidineacetone)dipalladium (0) (Pd$_2$(dba)$_3$), 0.5 mmol (0.1 ml) of tributylphosphine (PtBu$_3$), and 30 mmol (2.9 g) of sodium t-butoxide (NaOtBu) were added thereto, and the mixture was reacted at a temperature of 80° C. for 1 hour. The reaction product was cooled at ambient temperature; an organic layer was separated therefrom and then dried by using anhydrous magnesium sulfate, and then, concentrated under reduced pressure. The obtained residual was separation-purified by silica gel column chromatography to obtain Intermediate 1-1 (3.1 g, yield of 81%). The obtained compound was identified by MS/FAB. LC/MS cal: 385.47. found: 385.55.

Synthesis of Compound 3

8.0 mmol (3.1 g) of Intermediate 1-1 and 10 mmol (2.3 g) of 4-bromobiphenyl were diluted in 150 ml of toluene, and then, under a nitrogen atmosphere, 0.4 mmol (0.4 g) of tris(dibenzylidineacetone)dipalladium (0) (Pd$_2$(dba)$_3$), 0.4 mmol (0.1 ml) of tributylphosphine (PtBu$_3$), and 24 mmol (2.3 g) of sodium t-butoxide (NaOtBu) were added thereto, and the mixture was reacted at a temperature of 80° C. for 1 hour. The reaction product was cooled at ambient temperature; an organic layer was separated therefrom and then dried by using anhydrous magnesium sulfate, and then, concentrated under reduced pressure. The obtained residual was separation-purified by silica gel column chromatography to obtain Compound 3 (3.4 g, yield of 80%). The obtained compound was identified by MS/FAB and $^1$H NMR. LC/MS cal: 537.21. found: 537.22.

Synthesis Example 2: Synthesis of Compound 9

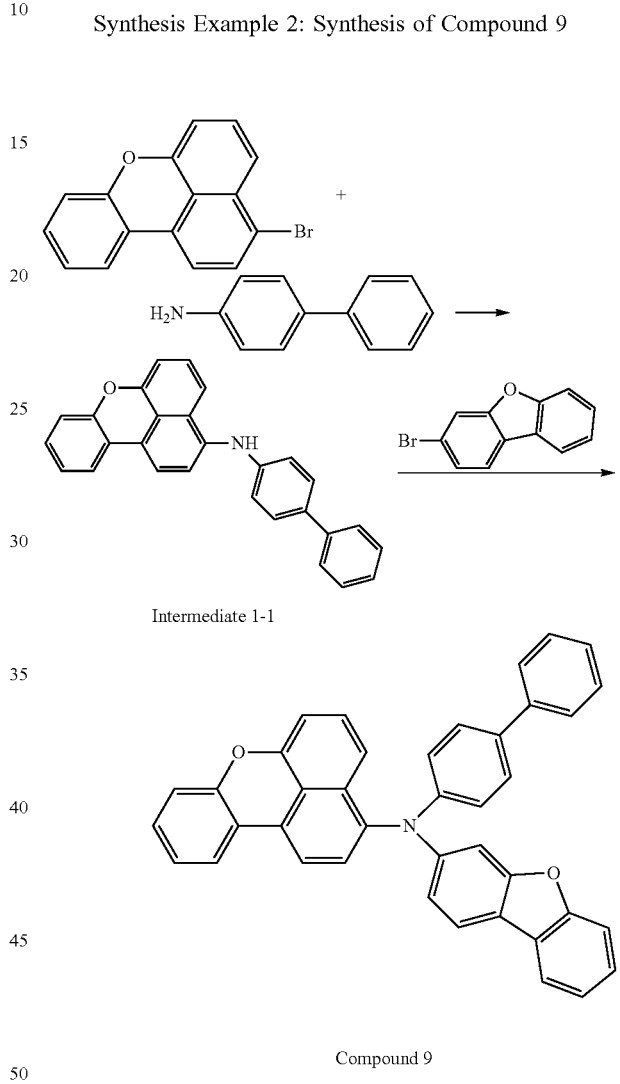

Intermediate 1-1

Compound 9

Synthesis of Compound 9

8.0 mmol (3.1 g) of Intermediate 1-1 and 10 mmol (2.5 g) of 3-bromodibenzofuran were diluted in 150 ml of toluene, and then, under a nitrogen atmosphere, 0.4 mmol (0.4 g) of tris(dibenzylidineacetone)dipalladium (0) (Pd$_2$(dba)$_3$), 0.4 mmol (0.1 ml) of tributylphosphine (PtBu$_3$), and 24 mmol (2.3 g) of sodium t-butoxide (NaOtBu) were added thereto, and the mixture was reacted at a temperature of 80° C. for 1 hour. The reaction product was cooled at ambient temperature; an organic layer was separated therefrom and then dried by using anhydrous magnesium sulfate, and then, concentrated under reduced pressure. The obtained residual was separation-purified by silica gel column chromatography to obtain Compound 9 (3.6 g, yield of 82%). The obtained compound was identified by MS/FAB and $^1$H NMR. LC/MS cal: 551.64. found: 537.19.

Synthesis Example 3: Synthesis of Compound 18

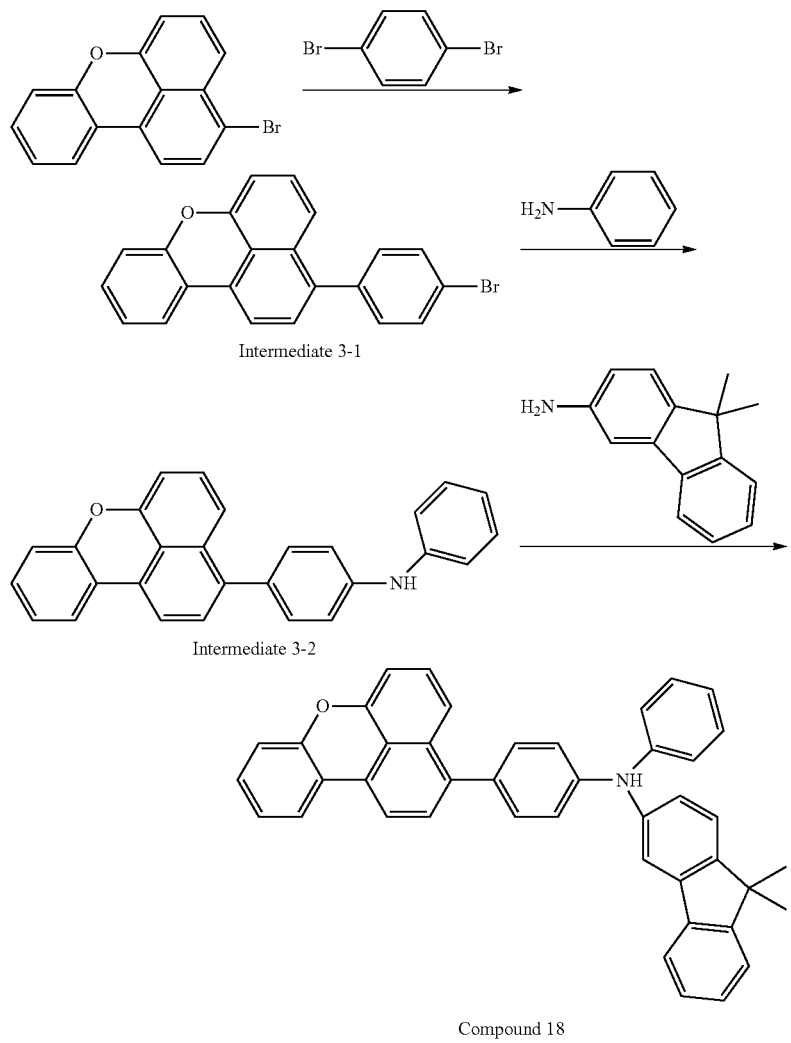

Compound 18

Synthesis of Intermediate 3-1

10.0 mmol (3.0 g) of 3-bromotriphenylzanthene and 12 mmol (2.8 g) of 1,4-dibromobenzene were diluted in 150 ml of toluene, and then, under a nitrogen atmosphere, 0.5 mmol (0.5 g) of tris(dibenzylidineacetone)dipalladium (0) (Pd$_2$(dba)$_3$), 0.5 mmol (0.1 ml) of tributylphosphine (PtBu$_3$), and 30 mmol (2.9 g) of sodium t-butoxide (NaOtBu) were added thereto, and the mixture was reacted at a temperature of 80° C. for 1 hour. The reaction product was cooled at ambient temperature, an organic layer was separated therefrom and then dried by using anhydrous magnesium sulfate, and then, concentrated under reduced pressure. The obtained residual was separation-purified by silica gel column chromatography to obtain Intermediate 3-1 (3.1 g, yield of 83%). The obtained compound was identified by MS/FAB. LC/MS cal: 373.25. found: 372.01.

Synthesis of Intermediate 3-2

8.0 mmol (3.0 g) of Intermediate 3-1 and 10 mmol (0.9 g) of aniline were diluted in 150 ml of toluene, and then, under a nitrogen atmosphere, 0.5 mmol (0.5 g) of tris(dibenzylidineacetone)dipalladium (0) (Pd$_2$(dba)$_3$), 0.5 mmol (0.1 ml) of tributylphosphine (PtBu$_3$), and 30 mmol (2.9 g) of sodium t-butoxide (NaOtBu) were added thereto, and the mixture was reacted at a temperature of 80° C. for 1 hour. The reaction product was cooled at ambient temperature; an organic layer was separated therefrom and then dried by using anhydrous magnesium sulfate, and then, concentrated under reduced pressure. The obtained residual was separation-purified by silica gel column chromatography to obtain Intermediate 3-2 (2.7 g, yield of 88%). The obtained compound was identified by MS/FAB. LC/MS cal: 385.47. found: 385.15.

Synthesis of Compound 18

8.0 mmol (2.6 g) of Intermediate 3-2 and 10 mmol (2.5 g) of 9,9-dimethyl-9H-florene-3-amine were diluted in 150 ml of toluene, and then, under a nitrogen atmosphere, 0.4 mmol (0.4 g) of tris(dibenzylidineacetone)dipalladium (0) (Pd$_2$(dba)$_3$), 0.4 mmol (0.1 ml) of tributylphosphine (PtBu$_3$), and 24 mmol (2.3 g) of sodium t-butoxide (NaOtBu) were added thereto, and the mixture was reacted at a temperature of 80° C. for 1 hour. The reaction product was cooled at ambient temperature; an organic layer was separated therefrom and then dried by using anhydrous magnesium sulfate, and then, concentrated under reduced pressure. The obtained residual was separation-purified by silica gel column chromatography to obtain Compound 18 (3.2 g, yield of 73%). The obtained compound was identified by MS/FAB and $^1$H NMR. LC/MS cal: 577.73. found: 577.15.

Synthesis Example 4: Synthesis of Compound 27

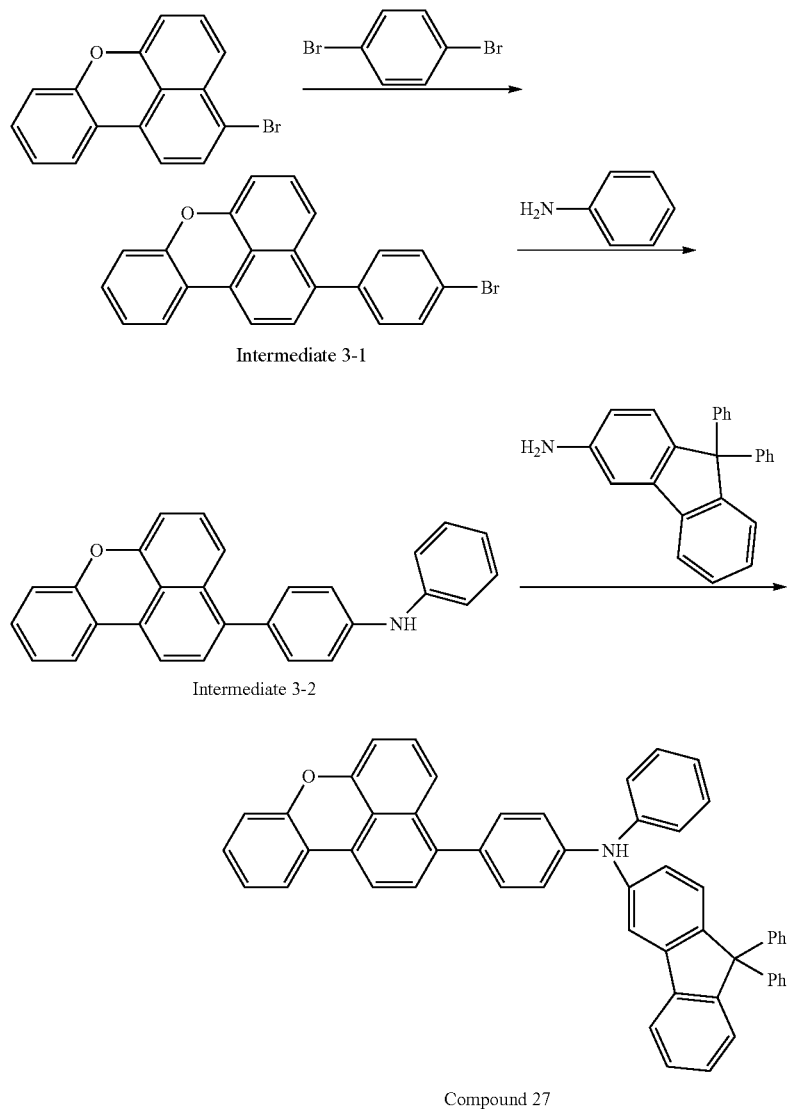

Synthesis of Compound 27

8.0 mmol (2.6 g) of Intermediate 3-2 and 10 mmol (4.0 g) of 9,9-diphenyl-9H-florene-2-amine were diluted in 150 ml of toluene, and then, under a nitrogen atmosphere, 0.4 mmol (0.4 g) of tris(dibenzylidineacetone)dipalladium (0) (Pd$_2$(dba)$_3$), 0.4 mmol (0.1 ml) of tributylphosphine (PtBu$_3$), and 24 mmol (2.3 g) of sodium t-butoxide (NaOtBu) were added thereto, and the mixture was reacted at a temperature of 80° C. for 1 hour. The reaction product was cooled at ambient temperature; an organic layer was separated therefrom and then dried by using anhydrous magnesium sulfate, and then, concentrated under reduced pressure. The obtained residual was separation-purified by silica gel column chromatography to obtain Compound 27 (4.7 g, yield of 84%). The obtained compound was identified by MS/FAB and $^1$H NMR. LC/MS cal: 701.87. found: 701.27.

Synthesis Example 5: Compound 36

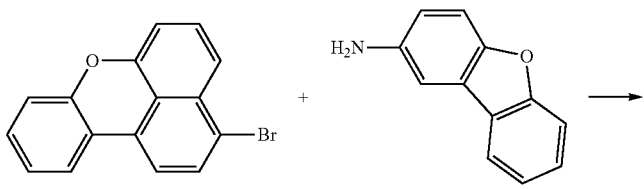

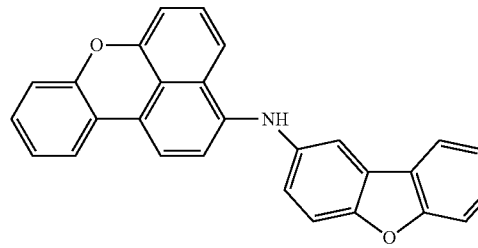
Intermediate 5-1

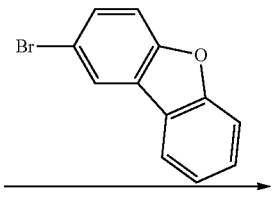

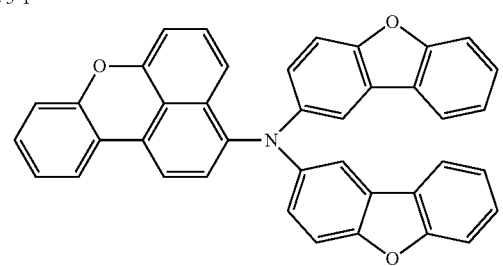
Compound 36

Synthesis of Intermediate 5-1

10.0 mmol (3.0 g) of 3-bromotriphenylzanthene and 40 mmol (9.9 g) of 2-bromodibenzofuran were diluted in 150 ml of toluene, and then, under a nitrogen atmosphere, 0.5 mmol (0.5 g) of trisdibenzylidineacetonedipalladium (0) (Pd$_2$(dba)$_3$), 0.5 mmol (0.1 ml) of tributylphosphine (PtBu$_3$), and 30 mmol (2.9 g) of sodium t-butoxide (NaOtBu) were added thereto, and the mixture was reacted at a temperature of 80° C. for 1 hour. The reaction product was cooled at ambient temperature; an organic layer was separated therefrom and then dried by using anhydrous magnesium sulfate, and then, concentrated under reduced pressure. The obtained residual was separation-purified by silica gel column chromatography to obtain Intermediate 5-1 (4.8 g, yield of 85%).

Synthesis of Compound 36

8.0 mmol (3.1 g) of Intermediate 5-1 and 10 mmol (2.3 g) of 2-bromodibenzofuran were diluted in 150 ml of toluene, and then, under a nitrogen atmosphere, 0.4 mmol (0.4 g) of tris(dibenzylidineacetone)dipalladium (0) (Pd$_2$(dba)$_3$), 0.4 mmol (0.1 ml) of tributylphosphine (PtBu$_3$), and 24 mmol (2.3 g) of sodium t-butoxide (NaOtBu) were added thereto, and the mixture was reacted at a temperature of 80° C. for 1 hour. The reaction product was cooled at ambient temperature; an organic layer was separated therefrom and then dried by using anhydrous magnesium sulfate, and then, concentrated under reduced pressure. The obtained residual was separation-purified by silica gel column chromatography to obtain Compound 36 (3.4 g, yield of 80%). The obtained compound was identified by MS/FAB and $^1$H NMR. LC/MS cal: 565.63. found: 565.47.

Synthesis Example 6: Synthesis of Compound 44

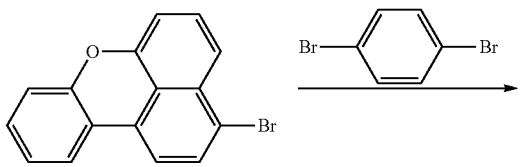

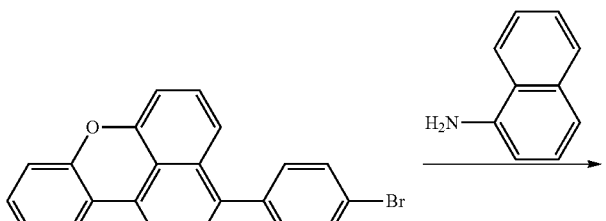
Intermediate 3-1

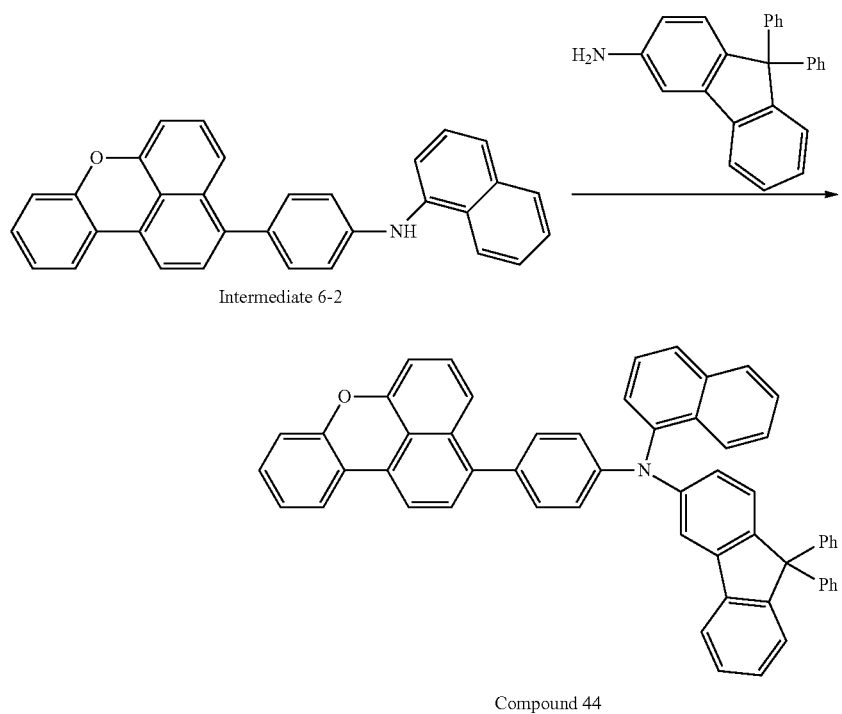

Intermediate 6-2

Compound 44

Synthesis of Intermediate 6-2

8.0 mmol (3.0 g) of Intermediate 3-1 and 10 mmol (1.4 g) of naphthalene-1-amine were diluted in 150 ml of toluene, and then, at nitrogen atmosphere, 0.5 mmol (0.5 g) of tris(dibenzylidineacetone)dipalladium (0) (Pd$_2$(dba)$_3$), 0.5 mmol (0.1 ml) of tributylphosphine (PtBu$_3$), and 30 mmol (2.9 g) of sodium t-butoxide (NaOtBu) were added thereto, and the mixture was reacted at a temperature of 80° C. for 1 hour. The reaction product was cooled at ambient temperature; an organic layer was separated therefrom and then dried by using anhydrous magnesium sulfate, and then, concentrated under reduced pressure. The obtained residual was separation-purified by silica gel column chromatography to obtain Intermediate 6-2 (2.7 g, yield of 77%). The obtained compound was identified by MS/FAB. LC/MS cal: 435.53. found: 435.16.

Synthesis of Compound 44

8.0 mmol (2.7 g) of Intermediate 6-2 and 10 mmol (4.0 g) of 9,9-diphenyl-9H-florene-3-amine were diluted in 150 ml of toluene, and then, under a nitrogen atmosphere, 0.4 mmol (0.4 g) of tris(dibenzylidineacetone)dipalladium (0) (Pd$_2$(dba)$_3$), 0.4 mmol (0.1 ml) of tributylphosphine (PtBu$_3$), and 24 mmol (2.3 g) of sodium t-butoxide (NaOtBu) were added thereto, and the mixture was reacted at a temperature of 80° C. for 1 hour. The reaction product was cooled at ambient temperature; an organic layer was separated therefrom and then dried by using anhydrous magnesium sulfate, and then, concentrated under reduced pressure. The obtained residual was separation-purified by silica gel column chromatography to obtain Compound 44 (5.2 g, yield of 87%). The obtained compound was identified by MS/FAB and $^1$H NMR. LC/MS cal: 577.73. found: 577.15.

Synthesis Example 7: Synthesis of Compound 54

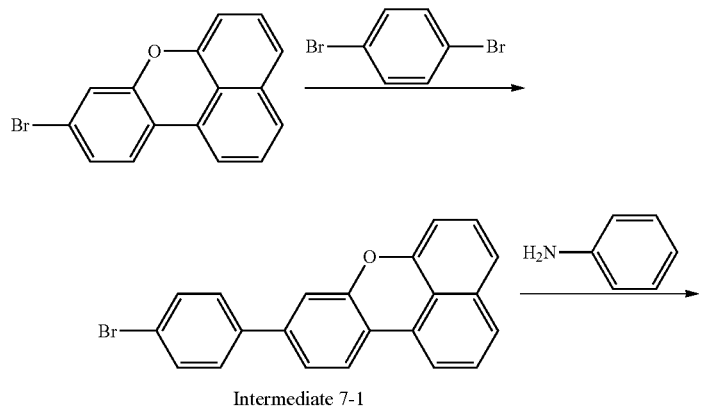

Intermediate 7-1

-continued

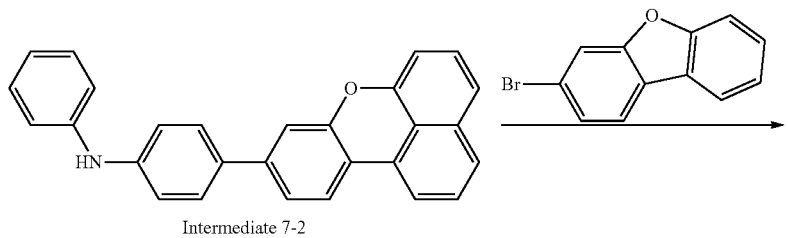

Intermediate 7-2

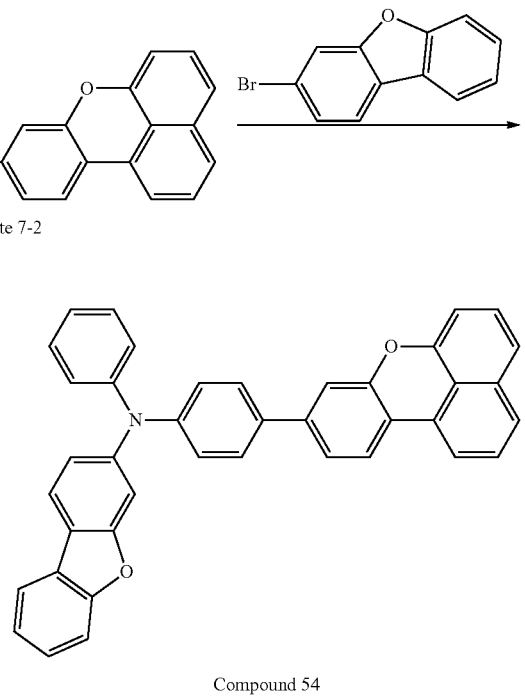

Compound 54

Synthesis of Intermediate 7-1

10.0 mmol (3.0 g) of 5-bromotriphenylzanthene and 12 mmol (2.8 g) of 1,4-dibromobenzene were diluted in 150 ml of toluene, and then, under a nitrogen atmosphere, 0.5 mmol (0.5 g) of tris(dibenzylidineacetone)dipalladium (0) (Pd$_2$(dba)$_3$), 0.5 mmol (0.1 ml) of tributylphosphine (PtBu$_3$), and 30 mmol (2.9 g) of sodium t-butoxide (NaOtBu) were added thereto, and the mixture was reacted at a temperature of 80° C. for 1 hour. The reaction product was cooled at ambient temperature; an organic layer was separated therefrom and then dried by using anhydrous magnesium sulfate, and then, concentrated under reduced pressure. The obtained residual was separation-purified by silica gel column chromatography to obtain Intermediate 7-1 (2.7 g, yield of 76%). The obtained compound was identified by MS/FAB. LC/MS cal: 373.25. found: 372.01.

Synthesis of Intermediate 7-2

10.0 mmol (3.0 g) of Intermediate 7-1 and 12 mmol (2.0 g) of aniline were diluted in 150 ml of toluene, and then, under a nitrogen atmosphere, 0.5 mmol (0.5 g) of tris (dibenzylidineacetone)dipalladium (0) (Pd$_2$(dba)$_3$), 0.5 mmol (0.1 ml) of tributylphosphine (PtBu$_3$), and 30 mmol (2.9 g) of sodium t-butoxide (NaOtBu) were added thereto, and the mixture was reacted at a temperature of 80° C. for 1 hour. The reaction product was cooled at ambient temperature, an organic layer was separated therefrom and then dried by using anhydrous magnesium sulfate, and then, concentrated under reduced pressure. The obtained residual was separation-purified by silica gel column chromatography to obtain Intermediate 7-2 (3.1 g, yield of 81%).

Synthesis of Compound 54

8.0 mmol (2.6 g) of Intermediate 7-2 and 10 mmol (2.5 g) of 3-bromodibenzofuran were diluted in 150 ml of toluene, and then, under a nitrogen atmosphere, 0.4 mmol (0.4 g) of tris(dibenzylidineacetone)dipalladium (0) (Pd$_2$(dba)$_3$), 0.4 mmol (0.1 ml) of tributylphosphine (PtBu$_3$), and 24 mmol (2.3 g) of sodium t-butoxide (NaOtBu) were added thereto, and the mixture was reacted at a temperature of 80° C. for 1 hour. The reaction product was cooled at ambient temperature, an organic layer was separated therefrom and then dried by using anhydrous magnesium sulfate, and then, concentrated under reduced pressure. The obtained residual was separation-purified by silica gel column chromatography to obtain Compound 54 (3.4 g, yield of 79%). The obtained compound was identified by MS/FAB and $^1$H NMR. LC/MS cal: 551.64. found: 551.45.

Synthesis Example 8: Synthesis of Compound 63

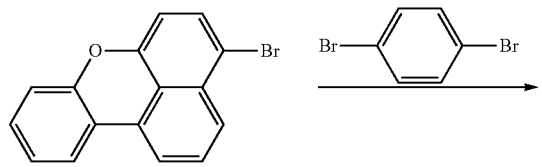

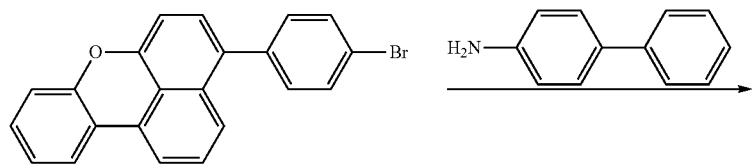

Intermediate 8-1

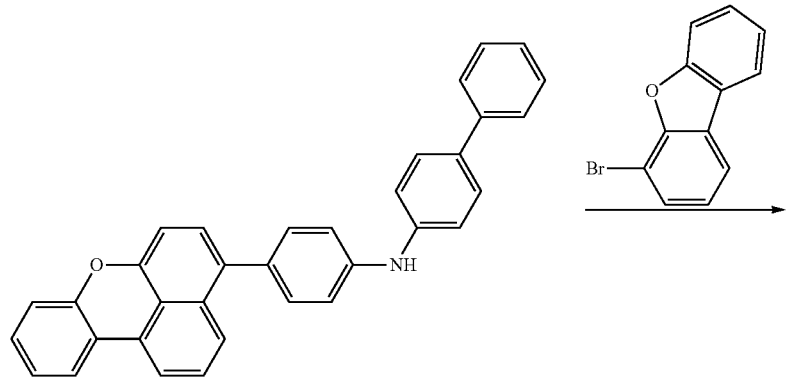

Intermediate 8-2

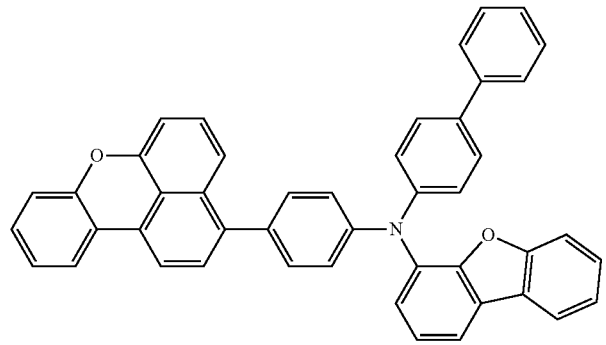

Compound 63

Synthesis of Intermediate 8-1

10.0 mmol (3.0 g) of 4-bromotriphenylzanthene and 12 mmol (2.8 g) of 1,4-dibromobenzene were diluted in 150 ml of toluene, and then, under a nitrogen atmosphere, 0.5 mmol (0.5 g) of tris(dibenzylidineacetone)dipalladium (0) (Pd$_2$(dba)$_3$), 0.5 mmol (0.1 ml) of tributylphosphine (PtBu$_3$), and 30 mmol (2.9 g) of sodium t-butoxide (NaOtBu) were added thereto, and the mixture was reacted at a temperature of 80° C. for 1 hour. The reaction product was cooled at ambient temperature, an organic layer was separated therefrom and then dried by using anhydrous magnesium sulfate, and then, concentrated under reduced pressure. The obtained residual was separation-purified by silica gel column chromatography to obtain Intermediate 8-1 (3.1 g, yield of 83%). The obtained compound was identified by MS/FAB. LC/MS cal: 373.25. found: 372.01.

Synthesis of Intermediate 8-2

8.0 mmol (3.0 g) of 4-bromotriphenylzanthene and 10 mmol (1.7 g) of 4-aminobiphenyl were diluted in 150 ml of toluene, and then, under a nitrogen atmosphere, 0.5 mmol (0.5 g) of tris(dibenzylidineacetone)dipalladium (0) (Pd$_2$(dba)$_3$), 0.5 mmol (0.1 ml) of tributylphosphine (PtBu$_3$), and 30 mmol (2.9 g) of sodium t-butoxide (NaOtBu) were added thereto, and the mixture was reacted at a temperature of 80° C. for 1 hour. The reaction product was cooled at ambient temperature, an organic layer was separated therefrom and then dried by using anhydrous magnesium sulfate, and then, concentrated under reduced pressure. The obtained residual was separation-purified by silica gel column chromatography to obtain Intermediate 8-2 (3.0 g, yield of 81%). The obtained compound was identified by MS/FAB. LC/MS cal: 461.56. found: 461.18.

Synthesis of Compound 63

5.3 mmol (3.0 g) of Intermediate 8-2 and 10 mmol (2.5 g) of 3-bromodibenzofuran were diluted in 150 ml of toluene, and then, under a nitrogen atmosphere, 0.4 mmol (0.4 g) of tris(dibenzylidineacetone)dipalladium (0) (Pd$_2$(dba)$_3$), 0.4 mmol (0.1 ml) of tributylphosphine (PtBu$_3$), and 24 mmol (2.3 g) of sodium t-butoxide (NaOtBu) were added thereto, and the mixture was reacted at a temperature of 80° C. for 1 hour. The reaction product was cooled at ambient temperature, an organic layer was separated therefrom and then dried by using anhydrous magnesium sulfate, and then, concentrated under reduced pressure. The obtained residual was separation-purified by silica gel column chromatography to obtain Compound 63 (3.0 g, yield of 91%). The obtained compound was identified by MS/FAB and $^1$H NMR. LC/MS cal: 627.74. found: 627.60.

Synthesis Example 9: Synthesis of Compound 72

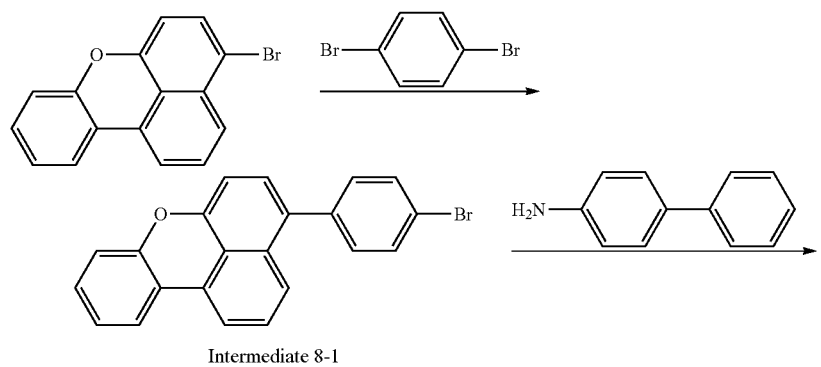

Intermediate 8-1

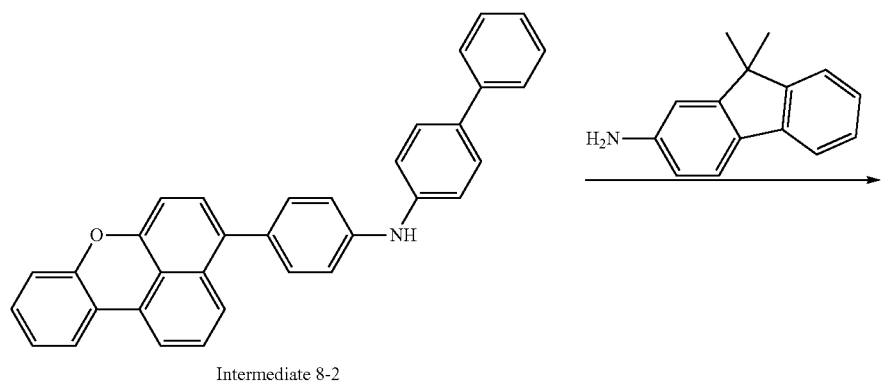

Intermediate 8-2

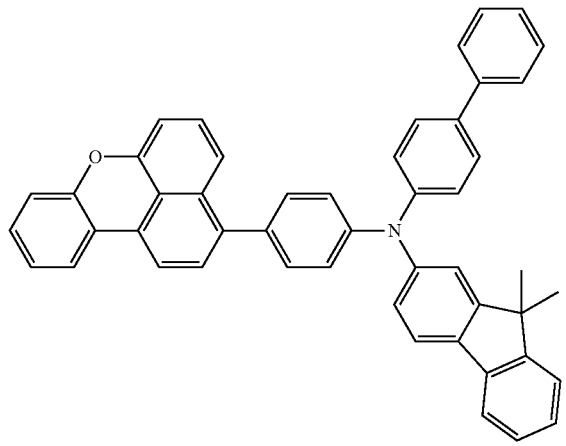

Compound 72

Synthesis of Compound 72

5.3 mmol (3.0 g) of Intermediate 8-2 and 10 mmol (2.1 g) of 9,9-dimethyl-9H-florene-2-amine were diluted in 150 ml of toluene, and then, under a nitrogen atmosphere, 0.4 mmol (0.4 g) of tris(dibenzylidineacetone)dipalladium (0) (Pd$_2$(dba)$_3$), 0.4 mmol (0.1 ml) of tributylphosphine (PtBu$_3$), and 24 mmol (2.3 g) of sodium t-butoxide (NaOtBu) were added thereto, and the mixture was reacted at a temperature of 80° C. for 1 hour. The reaction product was cooled at ambient temperature, an organic layer was separated therefrom and then dried by using anhydrous magnesium sulfate, and then, concentrated under reduced pressure. The obtained residual was separation-purified by silica gel column chromatography to obtain Compound 72 (2.4 g, yield of 67%). The obtained compound was identified by MS/FAB and $^1$H NMR. LC/MS cal: 653.82. found: 653.72.

Synthesis Example 10: Synthesis of Compound 81

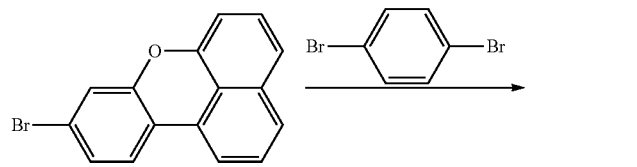

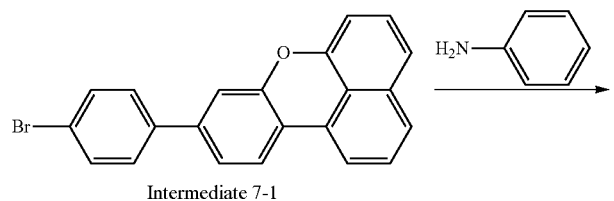

Intermediate 7-1

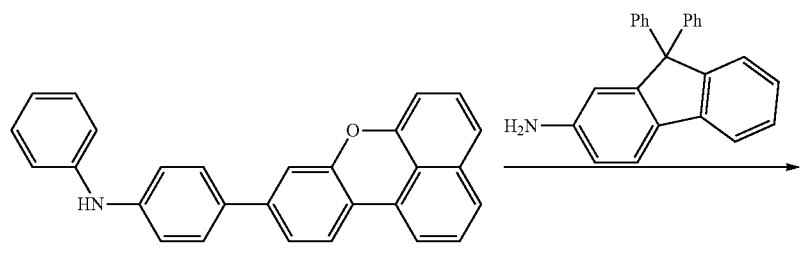

Intermediate 10-2

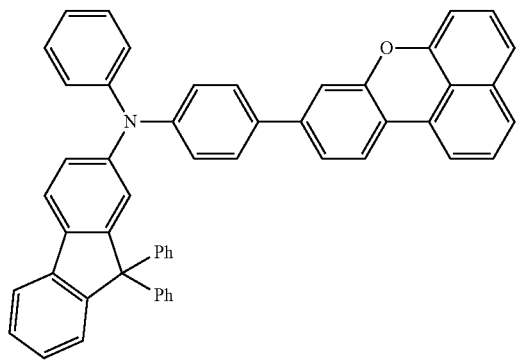

Compound 81

Synthesis of Intermediate 10-2

10.0 mmol (3.0 g) of Intermediate 7-1 and 12 mmol (1.1 g) of aniline were diluted in 150 ml of toluene, and then, under a nitrogen atmosphere, 0.5 mmol (0.5 g) of tris(dibenzylidineacetone)dipalladium (0) ($Pd_2(dba)_3$), 0.5 mmol (0.1 ml) of tributylphosphine ($PtBu_3$), and 30 mmol (2.9 g) of sodium t-butoxide (NaOtBu) were added thereto, and the mixture was reacted at a temperature of 80° C. for 1 hour. The reaction product was cooled at ambient temperature, an organic layer was separated therefrom and then dried by using anhydrous magnesium sulfate, and then, concentrated under reduced pressure. The obtained residual was separation-purified by silica gel column chromatography to obtain Intermediate 10-2 (3.3 g, yield of 82%). The obtained compound was identified by MS/FAB. LC/MS cal: 385.47. found: 385.15.

Synthesis of Compound 81

8.0 mmol (3.3 g) of Intermediate 10-2 and 10 mmol (2.6 g) of 9,9-diphenyl-9H-florene-2-amine were diluted in 150 ml of toluene, and then, under a nitrogen atmosphere, 0.4 mmol (0.4 g) of tris(dibenzylidineacetone)dipalladium (0) ($Pd_2(dba)_3$), 0.4 mmol (0.1 ml) of tributylphosphine ($PtBu_3$), and 24 mmol (2.3 g) of sodium t-butoxide (NaOtBu) were added thereto, and the mixture was reacted at a temperature of 80° C. for 1 hour. The reaction product was cooled at ambient temperature; an organic layer was separated therefrom and then dried by using anhydrous magnesium sulfate, and then, concentrated under reduced pressure. The obtained residual was separation-purified by silica gel column chromatography to obtain Compound 81 (4.3 g, yield of 77%). The obtained compound was identified by MS/FAB and $^1$H NMR. LC/MS cal: 701.87. found: 701.68.

Synthesis Example 11: Synthesis of Compound 90

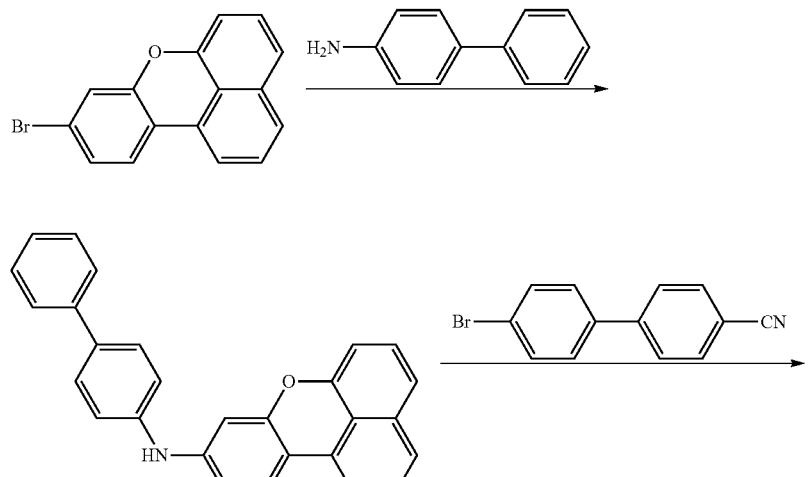

Intermediate 11-1

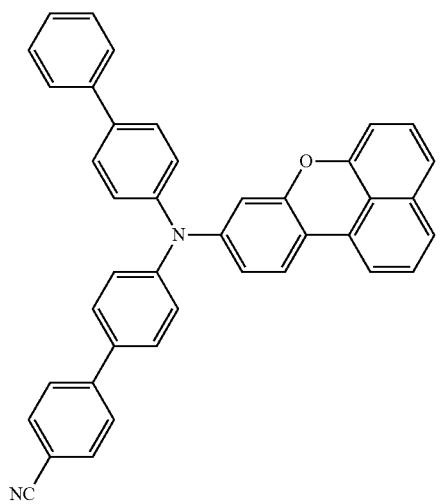

Compound 90

Synthesis of Intermediate 11-1

10.0 mmol (3.0 g) of 5-bromotriphenylzanthene and 12 mmol (2.0 g) of 4-aminobiphenyl were diluted in 150 ml of toluene, and then, under a nitrogen atmosphere, 0.5 mmol (0.5 g) of tris(dibenzylidineacetone)dipalladium (0) (Pd$_2$(dba)$_3$), 0.5 mmol (0.1 ml) of tributylphosphine (PtBu$_3$), and 30 mmol (2.9 g) of sodium t-butoxide (NaOtBu) were added thereto, and the mixture was reacted at a temperature of 80° C. for 1 hour. The reaction product was cooled at ambient temperature; an organic layer was separated therefrom and then dried by using anhydrous magnesium sulfate, and then, concentrated under reduced pressure. The obtained residual was separation-purified by silica gel column chromatography to obtain Intermediate 11-1 (3.1 g, yield of 81%). The obtained compound was identified by MS/FAB. LC/MS cal: 385.47. found: 385.55.

Synthesis of Compound 90

8.0 mmol (3.1 g) of Intermediate 11-1 and 10 mmol (2.6 g) of 4'-bromo-[1,1'-biphenyl]-4-carbonitrile were diluted in 150 ml of toluene, and then, under a nitrogen atmosphere, 0.4 mmol (0.4 g) of tris(dibenzylidineacetone)dipalladium (0) (Pd$_2$(dba)$_{-4}$), 0.4 mmol (0.1 ml) of tributylphosphine (PtBu$_3$), and 24 mmol (2.3 g) of sodium t-butoxide (NaOtBu) were added thereto, and the mixture was reacted at a temperature of 80° C. for 1 hour. The reaction product was cooled at ambient temperature; an organic layer was separated therefrom and then dried by using anhydrous magnesium sulfate, and then, concentrated under reduced pressure. The obtained residual was separation-purified by silica gel column chromatography to obtain Compound 90 (4.1 g, yield of 91%). The obtained compound was identified by MS/FAB and $^1$H NMR. LC/MS cal: 562.67. found: 562.19.

The compounds synthesized according to Synthesis Examples 1-11 were confirmed by $^1$H NMR and MS/FAB. Results thereof are shown in Table 1 below.

TABLE 1

| Compound | $^1$H NMR (CDCl$_3$, 400 MHz) | MS/FAB found | MS/FAB calc. |
|---|---|---|---|
| 3 | 7.09-7.04 (m, 4H), 6.98-6.91 (m, 4H), 6.77 (d, 2H), 6.66-6.62 (m, 6H) 6.48-6.45 (m, 4H), 6.24-6.20 (m, 4H) | 537.66 | 537.23 |
| 9 | 7.58-7.55 (m, 4H), 7.48-7.73 (m, 7H), 7.38-7.36 (m, 4H) 7.25-7.16 (m, 6H). 7.08-7.02 (m, 4H), 6.65-6.54 (m, 4H) | 551.64 | 551.19 |
| 18 | 7.58-7.56 (m, 4H), 7.48-7.43 (m, 6H), 7.09-7.04 (m, 4H), 6.66-6.62 (m, 4H) | 577.73 | 577.15 |
| 27 | 8.14 (d, 2H), 7.6-7.5 (m, 6H), 7.48-7.41 (m, 6H), 7.38-7.35 (d, 2H), 7.08-7.03 (m, 6H), 6.54-6.50 (m, 8H) | 701.87 | 701.27 |
| 36 | 7.43-7.39 (m, 4H), 7.35-7.31 (m, 7H), 7.28-7.21 (m, 4H) 7.15-7.11 (m, 6H). 7.03-7.00 (m, 4H), 6.54-6.50 (m, 4H) | 565.63 | 565.47 |
| 44 | 8.13 (d, 2H), 7.51-7.49 (m, 6H), 7.44-7.38 (m, 6H), 7.35-7.31 (d, 2H), 7.14-7.08 (m, 6H), 6.65-6.60 (m, 4H) | 751.93 | 751.24 |
| 54 | 7.54-7.51 (m, 4H), 7.47-7.45 (m, 7H), 7.41-7.39 (m, 4H) 7.36-7.31 (m, 6H). 7.24-7.22 (m, 4H), 6.87-6.85 (m, 4H) | 551.64 | 551.45 |
| 63 | 8.14 (d, 2H), 7.58-7.53 (m, 6H), 7.47-7.44 (m, 6H), 7.36-7.35 (d, 2H), 7.32-7.228 (m, 6H), 6.41-6.39 (m, 4H) | 627.74 | 627.60 |
| 72 | 8.14 (d, 2H), 7.54-7.51 (m, 6H), 7.43-7.40 (m, 6H), 7.37-7.35 (d, 2H), 7.23-7.20 (m, 6H), 6.53-6.51 (m, 4H) | 653.82 | 653.72 |
| 81 | 8.13 (d, 2H), 7.61-7.59 (m, 6H), 7.51-7.49 (m, 6H), 7.41-7.40 (d, 2H), 7.25-7.22 (m, 6H), 6.43-6.40 (m, 4H) | 701.81 | 701.68 |
| 90 | 7.57-7.55 (m, 4H), 7.44-7.41 (m, 7H), 7.39-7.37 (m, 4H) 7.28-7.25 (m, 6H). 7.20-7.18 (m, 4H), 6.75-6.74 (m, 4H) | 562.67 | 562.19 |

Example 1

A 15 Ωcm$^2$ (1,200 Å) ITO glass substrate (a product of Corning Inc.) was cut to a size of 50 mm×50 mm×0.7 mm, and was ultrasonically cleaned by using isopropyl alcohol and pure water for 5 minutes each, and then ultraviolet (UV) light was irradiated thereto for 30 minutes and exposed to ozone to clean. Then, the resultant structure was loaded into a vacuum deposition apparatus.

On the ITO glass substrate acting as an anode, 2-TNATA was vacuum-deposited to form a hole injection layer having a thickness of 600 Å, and Compound 3 was vacuum-deposited on the hole injection layer to form hole transport layer having a thickness of 300 Å, thereby completing the formation of a hole transport region.

9,10-di(naphthalen-2-yl)anthracene(ADN) (host) and N,N,N',N'-tetraphenyl-pyrene-1,6-diamine(TPD) (dopant) were co-deposited on the hole transport region at a weight ratio of 98:2 to form an emission layer having a thickness of 300 Å.

Alq$_3$ was vacuum-deposited on the emission layer to form an electron transport layer having a thickness of 300 Å, and LiF was deposited on the electron transport layer to form an electron injection layer having a thickness of 10 Å, thereby completing the formation of an electron transport region.

Al was vacuum-deposited on the electron transport region to form a cathode having a thickness of 3,000 Å, thereby completing the manufacture of an organic light-emitting device.

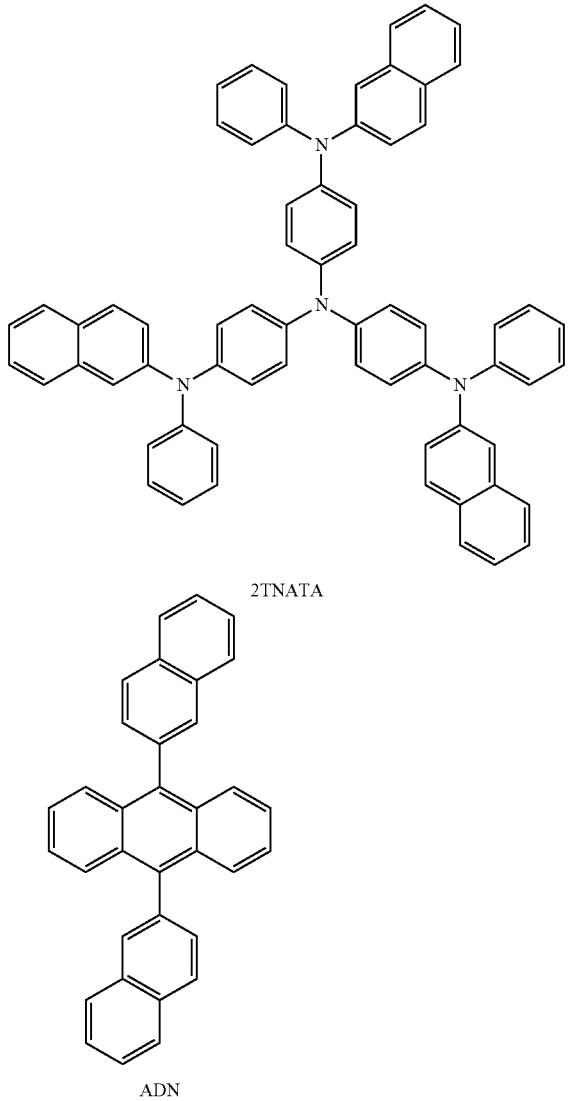

2TNATA

ADN

-continued

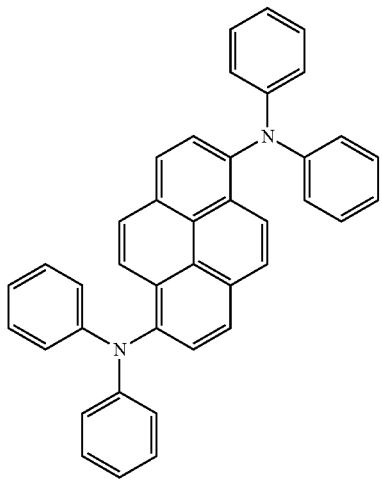

TPD

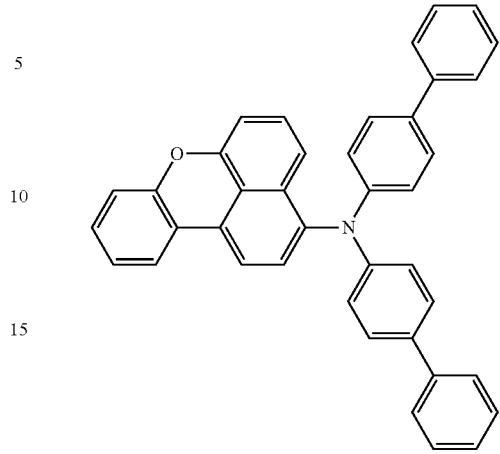

Examples 2 to 11 and Comparative Example 1

Organic light-emitting devices were manufactured in the same manner as in Example 1, except that in forming the hole transport layer, Compounds 9, 18, 27, 36, 44, 54, 63, 72, 81, and 90 were used instead of Compound 3, as indicated in Table 2, below.

Evaluation Example

The driving voltage, current density, brightness, efficiency, and half-lifespan of the organic light-emitting devices manufactured according to Examples 1 to 11, and Comparative Example 1 were measured by using Kethley SMU 236 and a brightness photometer PR650, and results thereof are shown in Table 2. The half-lifespan is a period of time that lapses until the brightness of the organic light-emitting device was 50% of initial brightness.

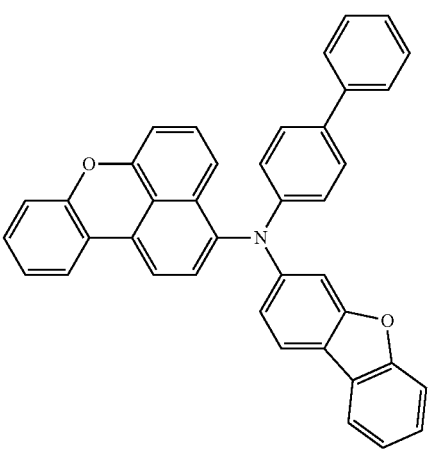

TABLE 2

| | Hole transport layer Material | Driving voltage (V) | Current density (mA/cm$^2$) | Brightness (cd/m$^2$) | Efficiency (cd/A) | Emission color | Half lifespan (hr @100 mA/cm$^2$) |
|---|---|---|---|---|---|---|---|
| Example 1 | Compound 3 | 4.4 | 50 | 3580 | 6.72 | Blue | 378 |
| Example 2 | Compound 9 | 4.5 | 50 | 3895 | 6.44 | Blue | 363 |
| Example 3 | Compound 18 | 4.5 | 50 | 3342 | 6.45 | Blue | 361 |
| Example 4 | Compound 27 | 4.5 | 50 | 3568 | 6.63 | Blue | 375 |
| Example 5 | Compound 36 | 4.3 | 50 | 3680 | 6.72 | Blue | 386 |
| Example 6 | Compound 44 | 4.4 | 50 | 3670 | 6.58 | Blue | 367 |
| Example 7 | Compound 54 | 4.5 | 50 | 3220 | 6.32 | Blue | 370 |
| Example 8 | Compound 63 | 4.4 | 50 | 3450 | 6.38 | Blue | 364 |
| Example 9 | Compound 72 | 4.5 | 50 | 3330 | 6.48 | Blue | 358 |
| Example 10 | Compound 81 | 4.5 | 50 | 3230 | 6.71 | Blue | 376 |
| Example 11 | Compound 90 | 4.5 | 50 | 3320 | 6.64 | Blue | 365 |
| Comparative Example 1 | NPB | 7.01 | 50 | 2645 | 5.29 | Blue | 358 |

18
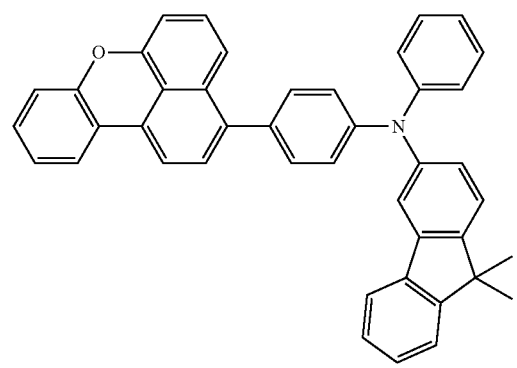
27
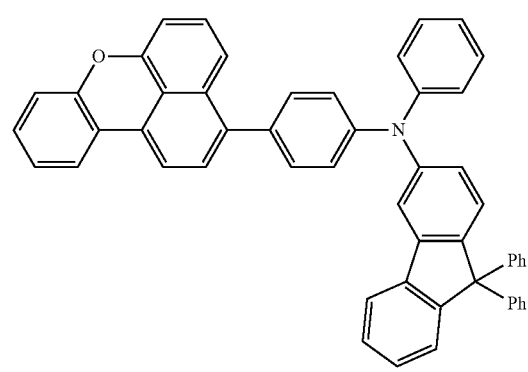
36
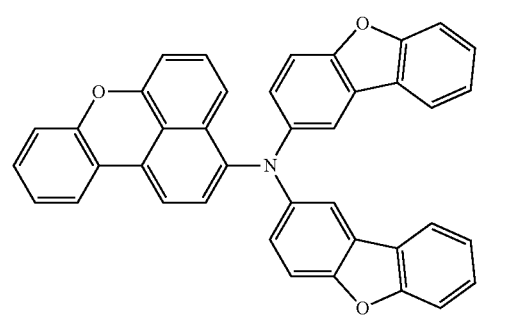
44
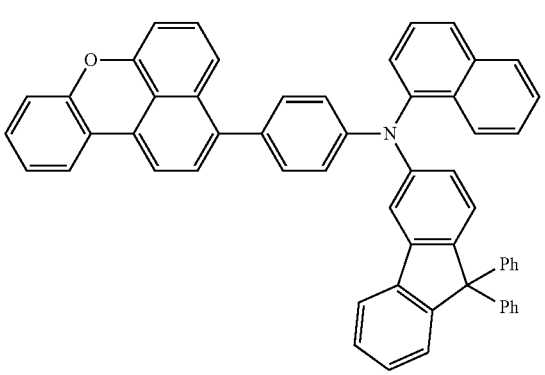
54
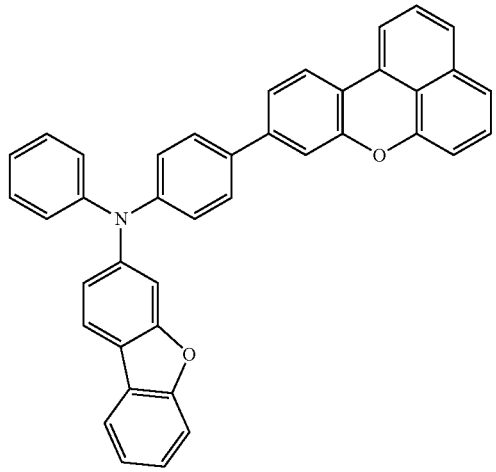
63
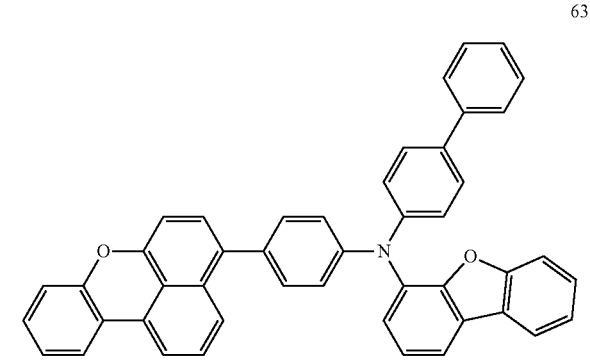
72
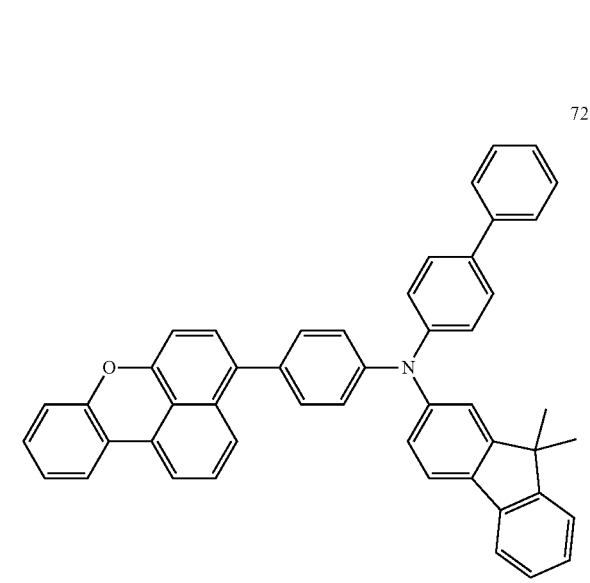

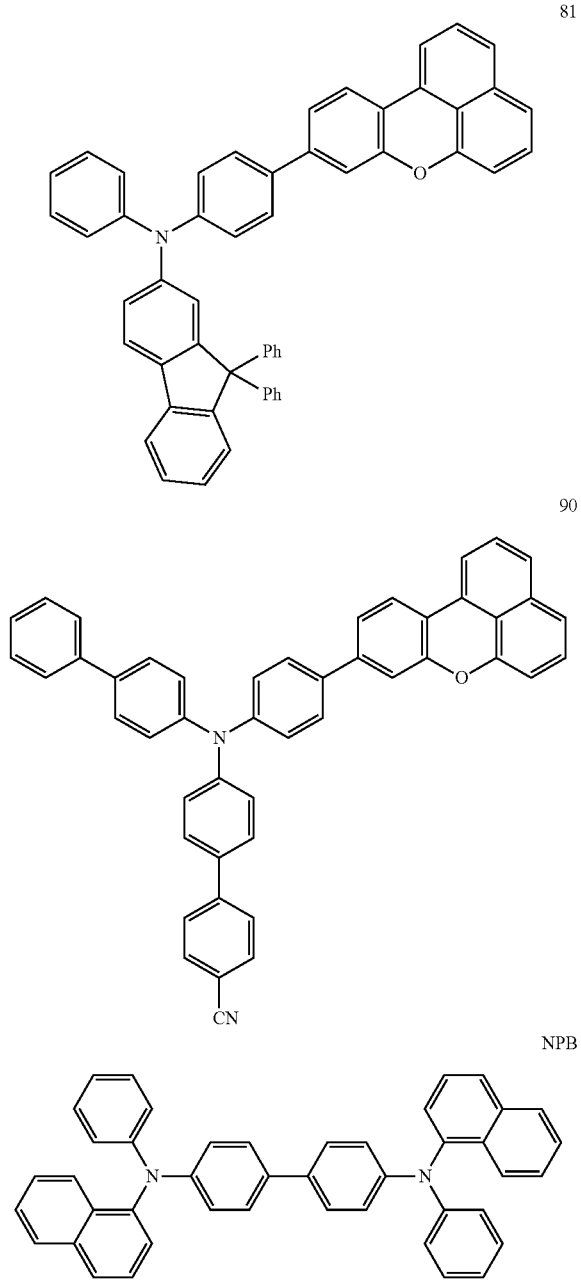

From Table 2, it may be seen that the organic light-emitting devices manufactured according to Examples 1 to 11 exhibited lower driving voltage, higher brightness, higher efficiency, and longer half-lifespan than the organic light-emitting device manufactured according to Comparative Example 1.

An organic light-emitting device including the condensed cyclic compound according to an exemplary embodiment may have low driving voltage, high efficiency, high luminance, and long lifespan.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A condensed cyclic compound having an asymmetric structure and being represented by one of the following Formulae 1-2, 1-3, 1-5, and 1-6:

<Formula 1-2>

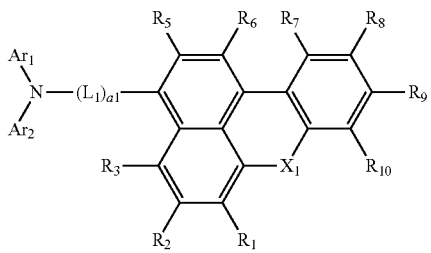

<Formula 1-3>

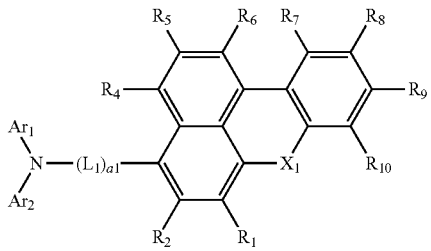

<Formula 1-5>

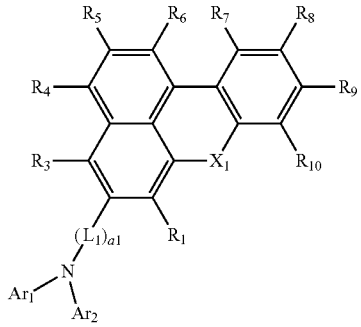

<Formula 1-6>

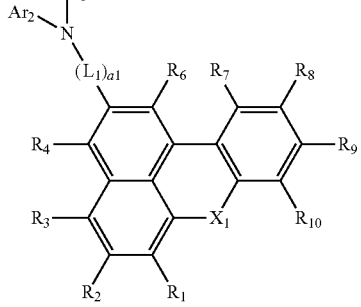

wherein, in Formulae 1-2, 1-3, 1-5, and 1-6, $X_1$ is selected from an oxygen atom (O) and a sulfur atom (S);

$R_1$ to $R_{10}$ are each independently selected from a hydrogen, a deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$), $L_1$ is selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a1 is an integer selected from 0 to 3, when a1 is two or more, a plurality of $L_1$ are identical or different;

$Ar_1$ and $Ar_2$ are each independently selected from a group represented by Formula 5-4, a group represented by Formula 5-5, a group represented by Formula 5-14, a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted spiro-fluorenyl group, a substituted or unsubstituted benzofluorenyl group, a substituted or unsubstituted dibenzofluorenyl group, a substituted or unsubstituted phenalenyl group, a substituted or unsubstituted phenanthrenyl group, a substituted or unsubstituted anthracenyl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pentacenyl group, a substituted or unsubstituted rubicenyl group, a substituted or unsubstituted coronenyl group, a substituted or unsubstituted ovalenyl group, a substituted or unsubstituted pyrrolyl group, a substituted or unsubstituted thiophenyl group, a substituted or unsubstituted furanyl group, a substituted or unsubstituted imidazolyl group, a substituted or unsubstituted pyrazolyl group, a substituted or unsubstituted thiazolyl group, a substituted or unsubstituted isothiazolyl group, a substituted or unsubstituted oxazolyl group, a substituted or unsubstituted isoxazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted isoquinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzoimidazolyl group, a substituted or unsubstituted benzofuranyl group, a substituted or unsubstituted benzothiophenyl group, a substituted or unsubstituted isobenzothiazolyl group, a substituted or unsubstituted benzoxazolyl group, a substituted or unsubstituted isobenzoxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted dibenzocarbazolyl group, a substituted or unsubstituted thiadiazolyl group, a substituted or unsubstituted imidazopyridinyl group, a substituted or unsubstituted imidazopyrimidinyl group, —Si($Q_1$)($Q_2$)($Q_3$), and —B($Q_4$)($Q_5$); and at least one substituent of the substituted phenyl group, substituted pentalenyl group, substituted indenyl group, substituted naphthyl group, substituted azulenyl group, substituted heptalenyl group, substituted indacenyl group, substituted acenaphthyl group, substituted fluorenyl group, substituted spiro-fluorenyl group, substituted benzofluorenyl group, substituted dibenzofluorenyl group, substituted phenalenyl group, substituted phenanthrenyl group, substituted anthracenyl group, substituted fluoranthenyl group, substituted triphenylenyl group, substituted pyrenyl group, substituted chrysenyl group, substituted naphthacenyl group, substituted picenyl group, substituted perylenyl group, substituted pentaphenyl group, substituted hexacenyl group, substituted pentacenyl group, substituted rubicenyl group, substituted coronenyl group, substituted ovalenyl group, substituted pyrrolyl group, substituted thiophenyl group, substituted furanyl group, substituted imidazolyl group, substituted pyrazolyl group, substituted thiazolyl group, substituted isothiazolyl group, substituted oxazolyl group, substituted isoxazolyl group, substituted pyridinyl group, substituted pyrazinyl group, substituted pyrimidinyl group, substituted pyridazinyl group, substituted isoindolyl group, substituted indolyl group, substituted indazolyl group, substituted purinyl group, substituted quinolinyl group, substituted isoquinolinyl group, substituted benzoquinolinyl group, substituted phthalazinyl group, substituted naphthyridinyl group, substituted quinoxalinyl group, substituted quinazolinyl group, substituted cinnolinyl group, substituted phenanthridinyl group, substituted acridinyl group, substituted phenanthrolinyl group, substituted phenazinyl group, substituted benzoimidazolyl group, substituted benzofuranyl group, substituted benzothiophenyl group, substituted isobenzothiazolyl group, substituted benzoxazolyl group, substituted isobenzoxazolyl group, substituted triazolyl group, substituted tetrazolyl group, substituted oxadiazolyl group, substituted triazinyl group, substituted dibenzocarbazolyl group, substituted thiadiazolyl group, substituted imidazopyridinyl group and substituted imidazopyrimidinyl group is selected from:

a deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amidino group, a hydrazine group, a hydrazone group, a carboxylic acid or a salt thereof, a sulfonic acid or a salt thereof, and a phosphoric acid or a salt thereof;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, and a dibenzocarbazolyl group;

a phenyl group, a naphthyl group, a pyridinyl group, a fluorenyl group, a spiro-fluorenyl group, a benzofluorenyl group, a dibenzofluorenyl group, a phenanthrenyl group, an anthracenyl group, a pyrenyl group, a chrysenyl group, and a dibenzocarbazolyl group, each substituted with at least one selected from a deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and a pyridinyl group; and —Si($Q_{31}$)($Q_{32}$)($Q_{33}$), wherein at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group and substituted monovalent non-aromatic condensed heteropolycyclic group is selected from:

a deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{11}$)($Q_{12}$)($Q_{13}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{21}$)($Q_{22}$)($Q_{23}$); and —Si($Q_{31}$)($Q_{32}$)($Q_{33}$), wherein $Q_1$ to $Q_3$, $Q_{11}$ to $Q_{13}$, $Q_{21}$ to $Q_{23}$, and $Q_{31}$ to $Q_{33}$ are each independently selected from a hydrogen, a deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group,

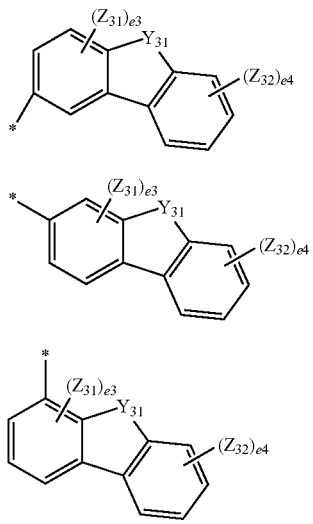

Formula 5-4

Formula 5-5

Formula 5-14 wherein, in Formulae 5-4, 5-5, and 5-14, $Y_{31}$ is O, S, $C(Z_{33})(Z_{34})$, or $Si(Z_{36})(Z_{37})$;

$Z_{31}$ to $Z_{34}$, $Z_{36}$, and $Z_{37}$ are each independently selected from:

a hydrogen, a deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group and a dibenzocarbazolyl group;

a phenyl group, a naphthyl group, a pyridinyl group, a fluorenyl group, a spiro-fluorenyl group, a benzofluorenyl group, a dibenzofluorenyl group, a phenanthrenyl group, an anthracenyl group, a pyrenyl group, a chrysenyl group, and a dibenzocarbazolyl group, each substituted with at least one selected from a deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and a pyridinyl group; and —$Si(Q_{31})(Q_{32})(Q_{33})$ wherein $Q_{31}$ to $Q_{33}$ are defined the same as the $Q_{31}$ to $Q_{33}$ above;

e3 is an integer selected from 1 to 3, e4 is an integer selected from 1 to 4, and * indicates a binding site to a neighboring atom.

2. The condensed cyclic compound as claimed in claim 1, wherein (i) a1 is 0 or (ii) a 1 is 1, 2, or 3, and each $L_1$ is independently selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group and an imidazopyrimidinylene group, each substituted with at least one selected from a deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

3. The condensed cyclic compound as claimed in claim 1, wherein (i) a1 is 0 or (ii) a1 is 1, 2, or 3, and each $L_1$ is independently a group represented by one of the following Formulae 3-1 to 3-35:

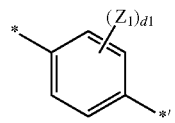

Formula 3-1

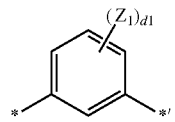

Formula 3-2

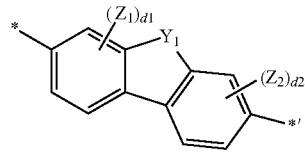

Formula 3-3

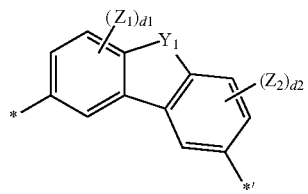

Formula 3-4

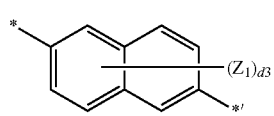

Formula 3-5

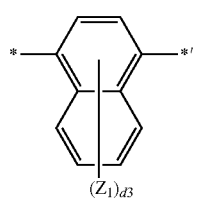

Formula 3-6

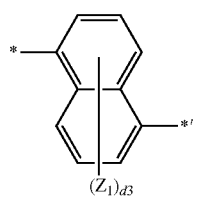

Formula 3-7

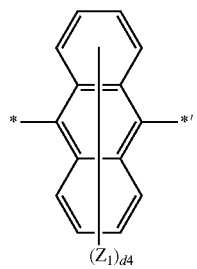

Formula 3-8

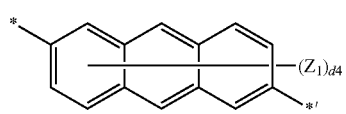

Formula 3-9

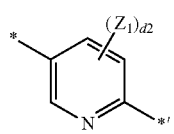

Formula 3-10

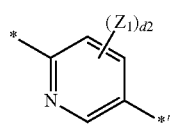

Formula 3-11

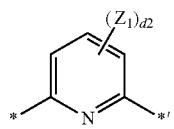

Formula 3-12

Formula 3-13
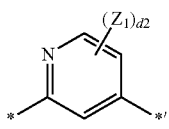
Formula 3-14
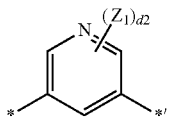
Formula 3-15
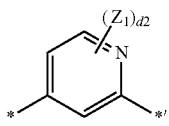
Formula 3-16
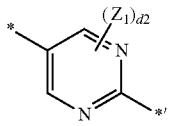
Formula 3-17
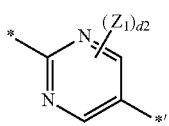
Formula 3-18
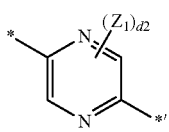
Formula 3-19
Formula 3-20
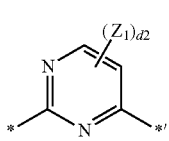
Formula 3-21
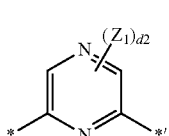
Formula 3-22
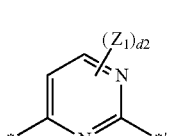
Formula 3-23
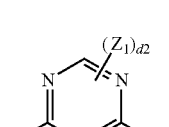
Formula 3-24
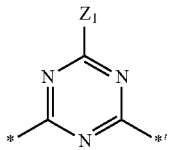
Formula 3-25
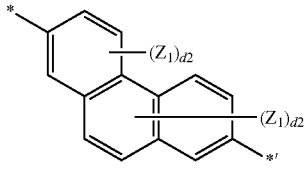
Formula 3-26
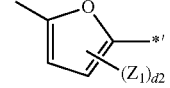
Formula 3-27
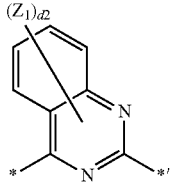
Formula 3-28
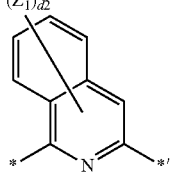
Formula 3-29
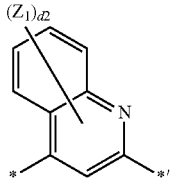
Formula 3-30
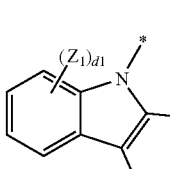
Formula 3-31
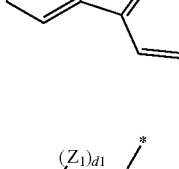
Formula 3-32

-continued

Formula 3-33
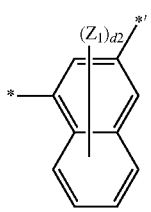

Formula 3-34
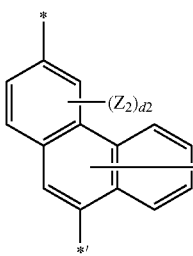

Formula 3-35
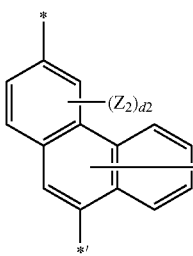

wherein, in Formulae 3-1 to 3-35,
Y$_1$ is O, S, C(Z$_3$)(Z$_4$), N(Z$_5$), or Si(Z$_6$)(Z$_7$);
Z$_1$ to Z$_7$ are each independently selected from a hydrogen, a deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group,
d1 is an integer selected from 1 to 4, d2 is an integer selected from 1 to 3, d3 is an integer selected from 1 to 6, d4 is an integer selected from 1 to 8, d5 is 1 or 2, d6 is an integer selected from 1 to 5, and * and *' each indicate a binding site to a neighboring atom.

4. The condensed cyclic compound as claimed in claim 1, wherein (i) a1 is 0 or (ii) a1 is 1, 2, or 3, and each L$_1$ is independently a group represented by one of the following Formulae 4-1 to 4-29:

Formula 4-1
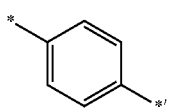

Formula 4-2
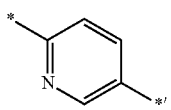

Formula 4-3
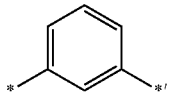

Formula 4-4
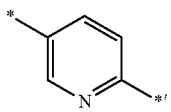

Formula 4-5
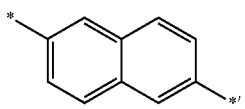

Formula 4-6
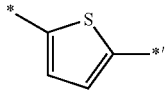

Formula 4-7
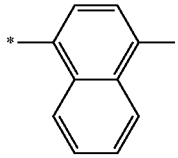

Formula 4-8
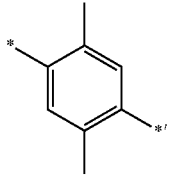

Formula 4-9
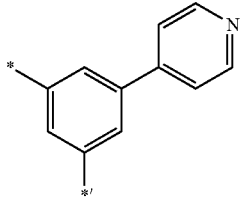

Formula 4-10
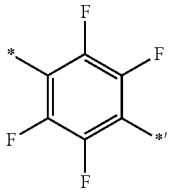

Formula 4-11
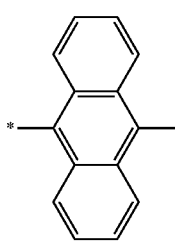

165
-continued
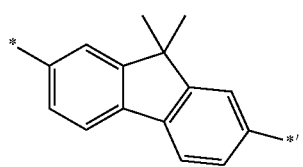
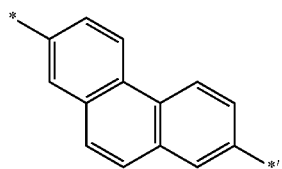
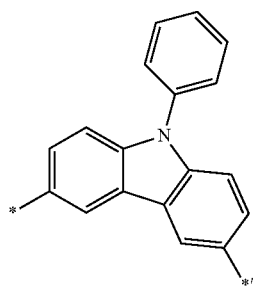
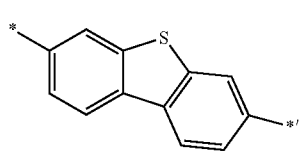
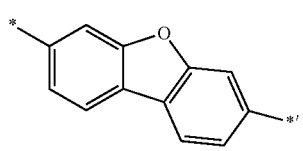
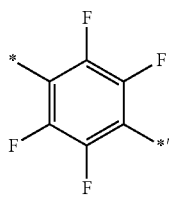
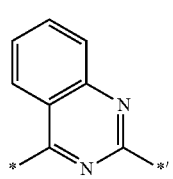
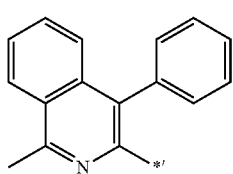
166
-continued
Formula 4-12
Formula 4-13
Formula 4-14
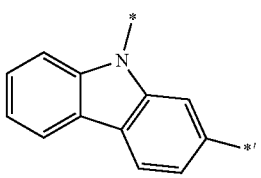
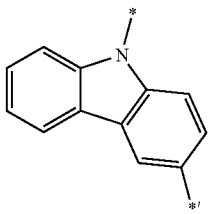
Formula 4-15
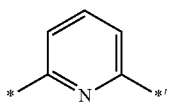
Formula 4-16
Formula 4-17
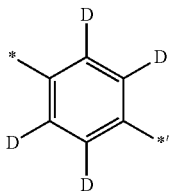
Formula 4-18
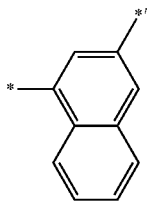
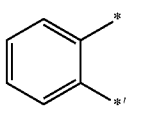
Formula 4-19
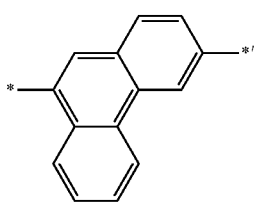
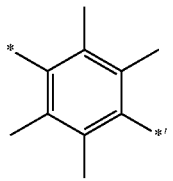
Formula 4-20
Formula 4-21
Formula 4-22
Formula 4-23
Formula 4-24
Formula 4-25
Formula 4-26
Formula 4-27
Formula 4-28

-continued

Formula 4-29

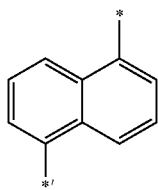

wherein, in Formulae 4-1 to 4-29, * and *' each indicate a binding site to a neighboring atom.

5. The condensed cyclic compound as claimed in claim 1, wherein (i) a1 is 0 or (ii) a1 is 1, 2, or 3, and each $L_1$ is independently selected from:

a phenylene group, a naphthylene group, a pyridinylene group, a pyrimidinylene group, and a triazinylene group; and a phenylene group, a naphthylene group, a pyridinylene group, a pyrimidinylene group, and a triazinylene group, each substituted with at least one selected from a deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a pyridinyl group, a pyrimidinyl group, and a triazinyl group.

6. The condensed cyclic compound as claimed in claim 1, wherein a1 is 0 or 1.

7. The condensed cyclic compound as claimed in claim 1, wherein $Ar_1$ and $Ar_2$ are each independently a group represented by one of the following Formulae 5-1 to 5-16:

Formula 5-1

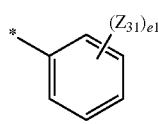

Formula 5-2

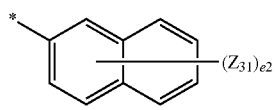

Formula 5-3

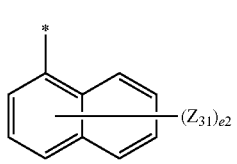

Formula 5-4

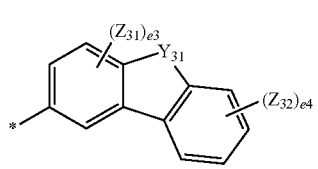

Formula 5-5

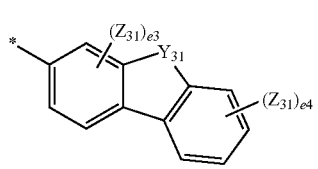

-continued

Formula 5-6

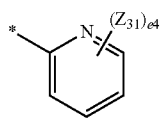

Formula 5-7

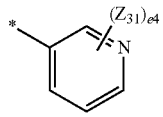

Formula 5-8

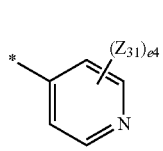

Formula 5-9

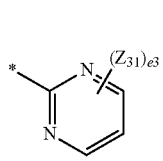

Formula 5-10

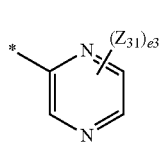

Formula 5-11

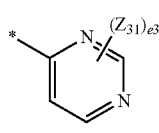

Formula 5-12

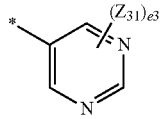

Formula 5-13

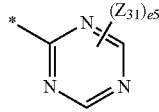

Formula 5-14

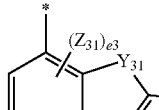

Formula 5-15

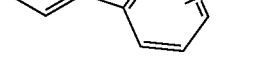

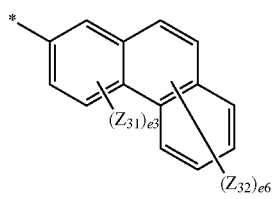

Formula 5-16

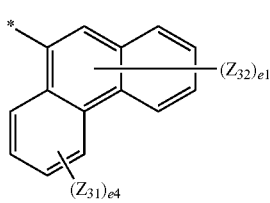

wherein, in Formulae 5-1 to 5-16, $Y_{31}$ is O, S, $C(Z_{33})(Z_{34})$, or $Si(Z_{36})(Z_{37})$;

$Z_{31}$ to $Z_{34}$, $Z_{36}$, and $Z_{37}$ are each independently selected from:

a hydrogen, a deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group and a dibenzocarbazolyl group;

a phenyl group, a naphthyl group, a pyridinyl group, a fluorenyl group, a spiro-fluorenyl group, a benzofluorenyl group, a dibenzofluorenyl group, a phenanthrenyl group, an anthracenyl group, a pyrenyl group, a chrysenyl group, and a dibenzocarbazolyl group, each substituted with at least one selected from a deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and a pyridinyl group; and —$Si(Q_{31})(Q_{32})(Q_{33})$ wherein $Q_{31}$ to $Q_{33}$ are each independently selected from a hydrogen, a deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, and a carbazolyl group;

e1 is an integer selected from 1 to 5, e2 is an integer selected from 1 to 7, e3 is an integer selected from 1 to 3, e4 is an integer selected from 1 to 4, e5 is 1 or 2, e6 is an integer selected from 1 to 6, and * indicates a binding site to a neighboring atom.

8. The condensed cyclic compound as claimed in claim 1, wherein $Ar_1$ and $Ar_2$ are each independently a group represented by one of the following Formulae 6-1 to 6-13 and 6-15 to 6-35:

Formula 6-1

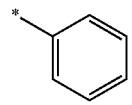

Formula 6-2

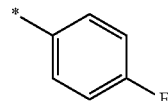

Formula 6-3

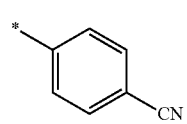

Formula 6-4

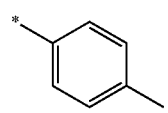

Formula 6-5

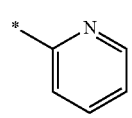

Formula 6-6

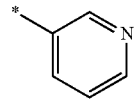

Formula 6-7

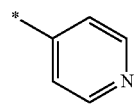

Formula 6-8

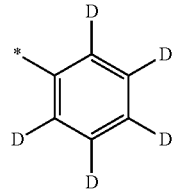

Formula 6-9

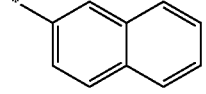

Formula 6-10

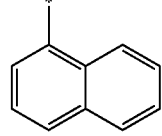

Formula 6-11

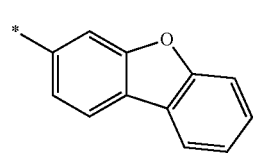

Formula 6-12

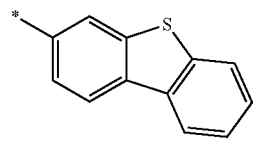

171
-continued
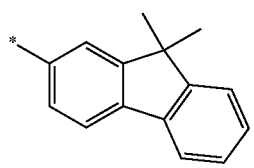
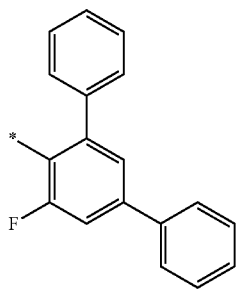
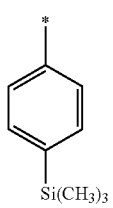
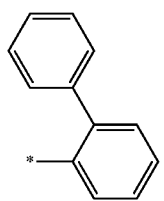
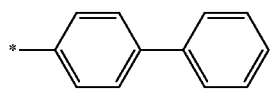
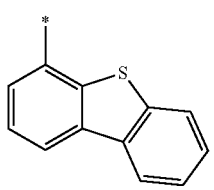
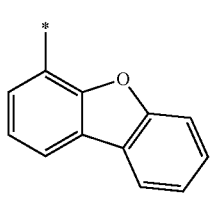
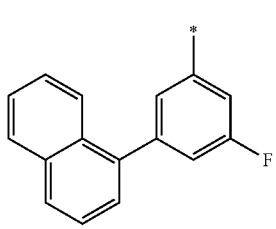
172
-continued
Formula 6-13
Formula 6-15
Formula 6-16
Formula 6-17
Formula 6-18
Formula 6-19
Formula 6-20
Formula 6-21
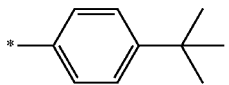
Formula 6-22
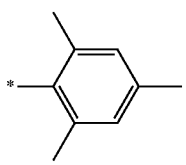
Formula 6-23
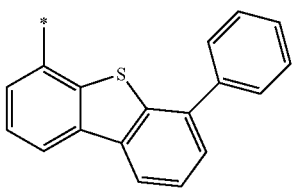
Formula 6-24
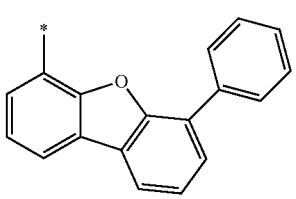
Formula 6-25
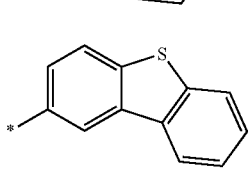
Formula 6-26
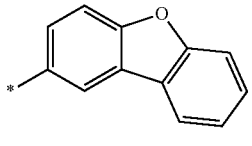
Formula 6-27
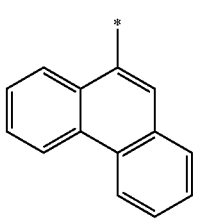
Formula 6-28
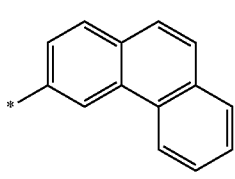
Formula 6-29
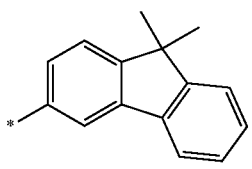
Formula 6-30

-continued

Formula 6-31
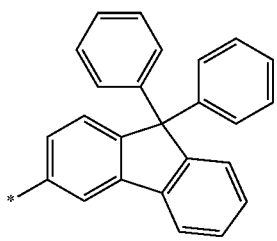

Formula 6-32
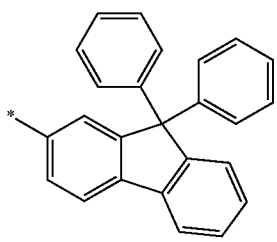

Formula 6-33
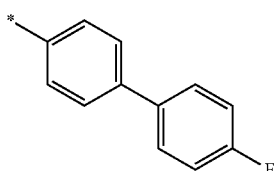

Formula 6-34
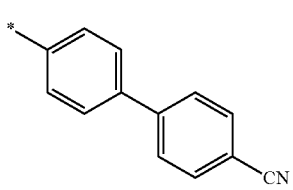

Formula 6-35
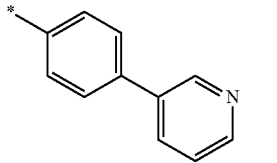

wherein, in Formulae 6-1 to 6-13 and 6-15 to 6-35, * indicates a binding site to a neighboring atom.

9. The condensed cyclic compound as claimed in claim 1, wherein $R_1$ to $R_{10}$ are each independently selected from:
a hydrogen, a deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;
a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group;
a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group, each substituted with at least one selected from a deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, an imidazopyrimidinyl group, and —Si($Q_{31}$)($Q_{32}$)($Q_{33}$); and
—Si($Q_1$)($Q_2$)($Q_3$),
wherein $Q_1$ to $Q_3$ and $Q_{31}$ to $Q_{33}$ are each independently selected from a $C_1$-$C_{10}$ alkyl group, a $C_1$-$C_{10}$ alkoxy group, a phenyl group, and a naphthyl group.

10. The condensed cyclic compound as claimed in claim 1, wherein $R_1$ to $R_{10}$ are each independently selected from:
a hydrogen, a deuterium, —F, —Cl, —Br, —I, a hydroxyl group, a cyano group, a nitro group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;
a phenyl group, a naphthyl group, a pyridinyl group, a pyrimidinyl group, and a triazinyl group;
a phenyl group, a naphthyl group, a pyridinyl group, a pyrimidinyl group, and a triazinyl group, each substituted with at least one selected from a deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, and —Si($Q_{31}$)($Q_{32}$)($Q_{33}$); and —Si($Q_1$)($Q_2$)($Q_3$)

wherein $Q_1$ to $Q_3$ and $Q_{31}$ to $Q_{33}$ are each independently selected from a $C_1$-$C_{10}$ alkyl group, a $C_1$-$C_{10}$ alkoxy group, a phenyl group, and a naphthyl group.

11. The condensed cyclic compound as claimed in claim 1, wherein the condensed cyclic compound represented by one of Formulae 1-2, 1-3, 1-5, and 1-6 is represented by one of the following Formulae 1-2(A), 1-2(B), 1-3(A), and 1-3(B):

<Formula 1-2(A)>

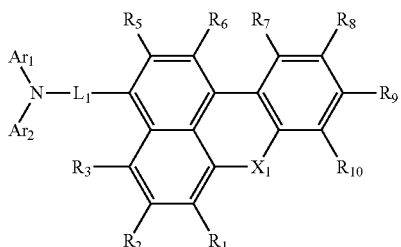

<Formula 1-2(B)>

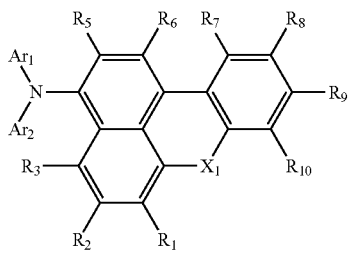

<Formula 1-3(A)>

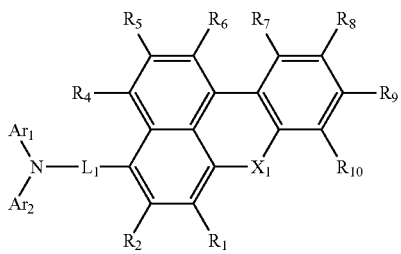

<Formula 1-3(B)>

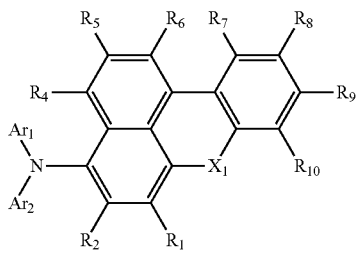

wherein, in Formulae 1-2(A), 1-2(B), 1-3(A), and 1-3(B), $X_1$, $L_1$, $Ar_1$, $Ar_2$, and $R_1$ to $R_{10}$ are defined the same as $X_1$, $L_1$, $Ar_1$, $Ar_2$, and $R_1$ to $R_{10}$ of Formulae 1-2, 1-3, 1-5, and 1-6.

12. The condensed cyclic compound as claimed in claim 1 wherein the condensed cyclic compound represented by Formula 1 is one of the following Compounds 1 to 45, 61 to 75, and 91 to 102:

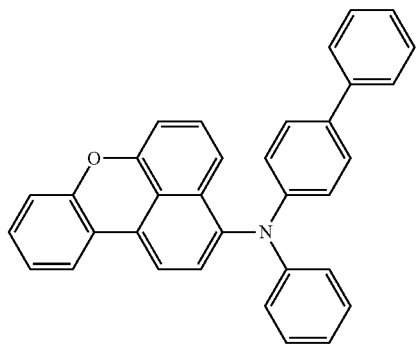

1

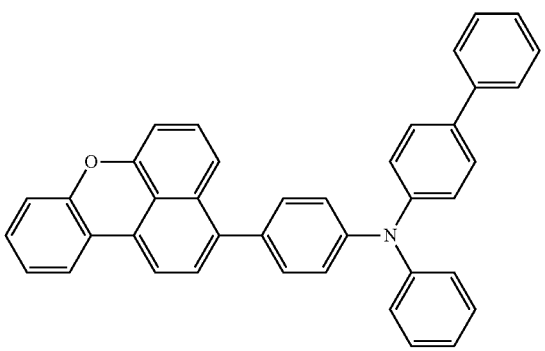

2

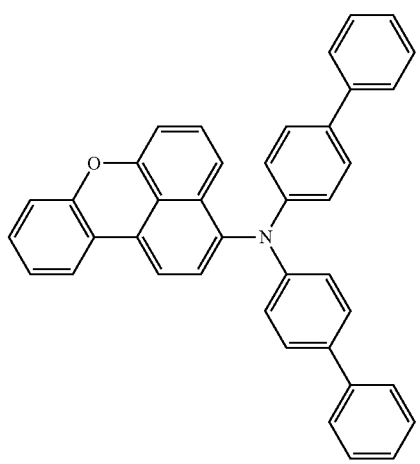

3

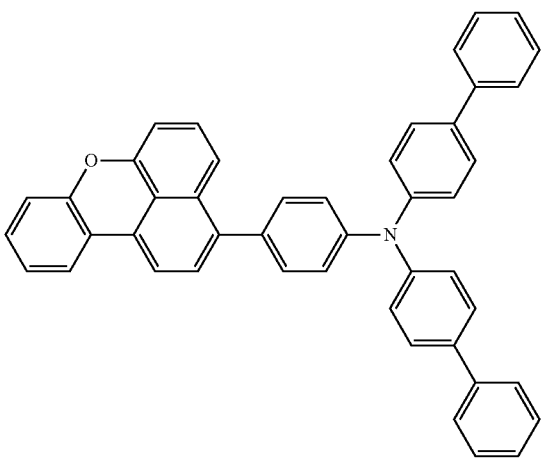

4

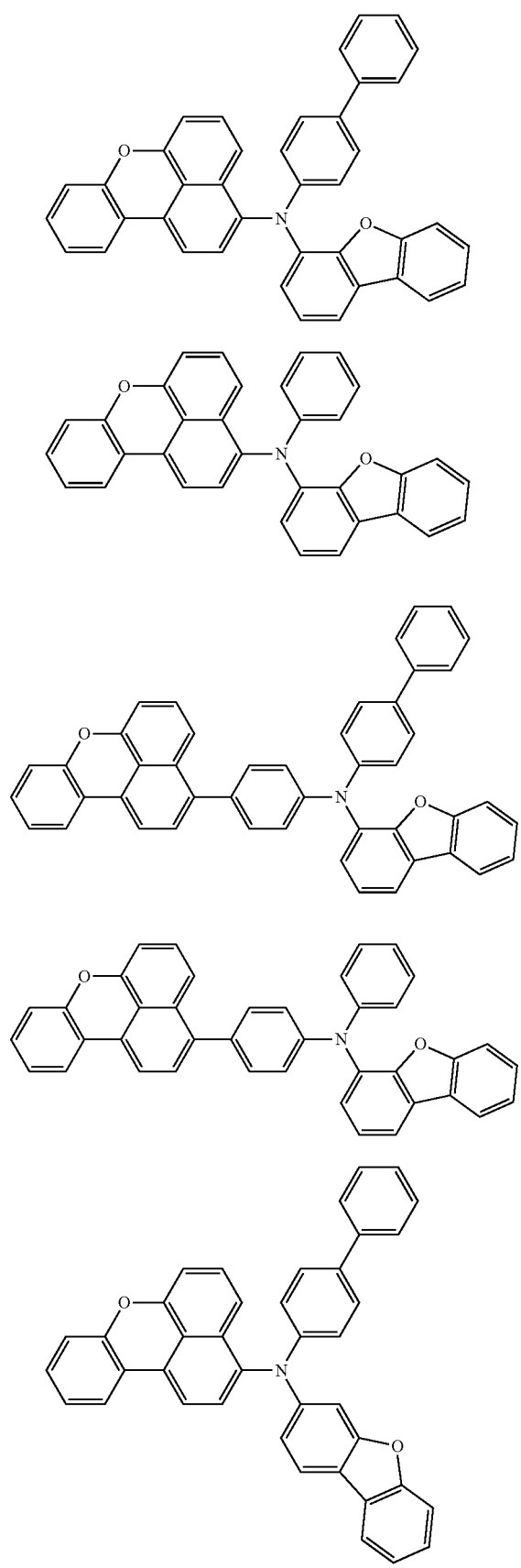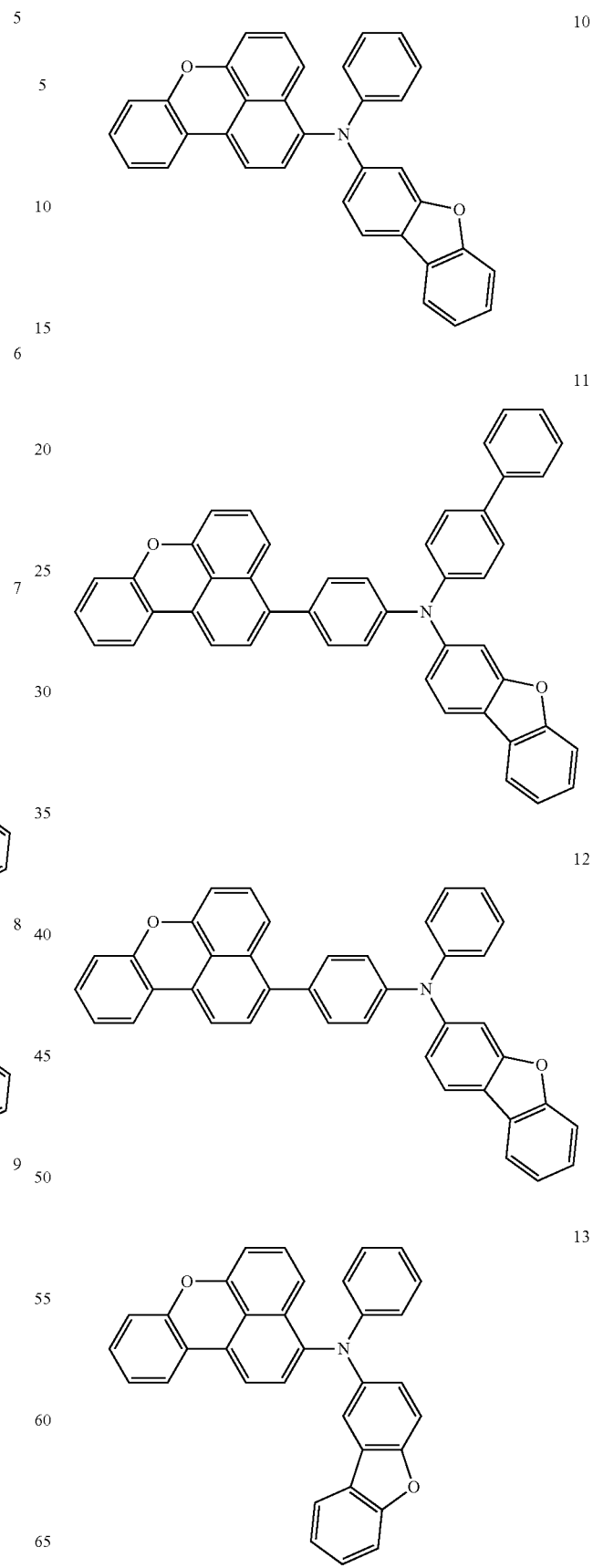

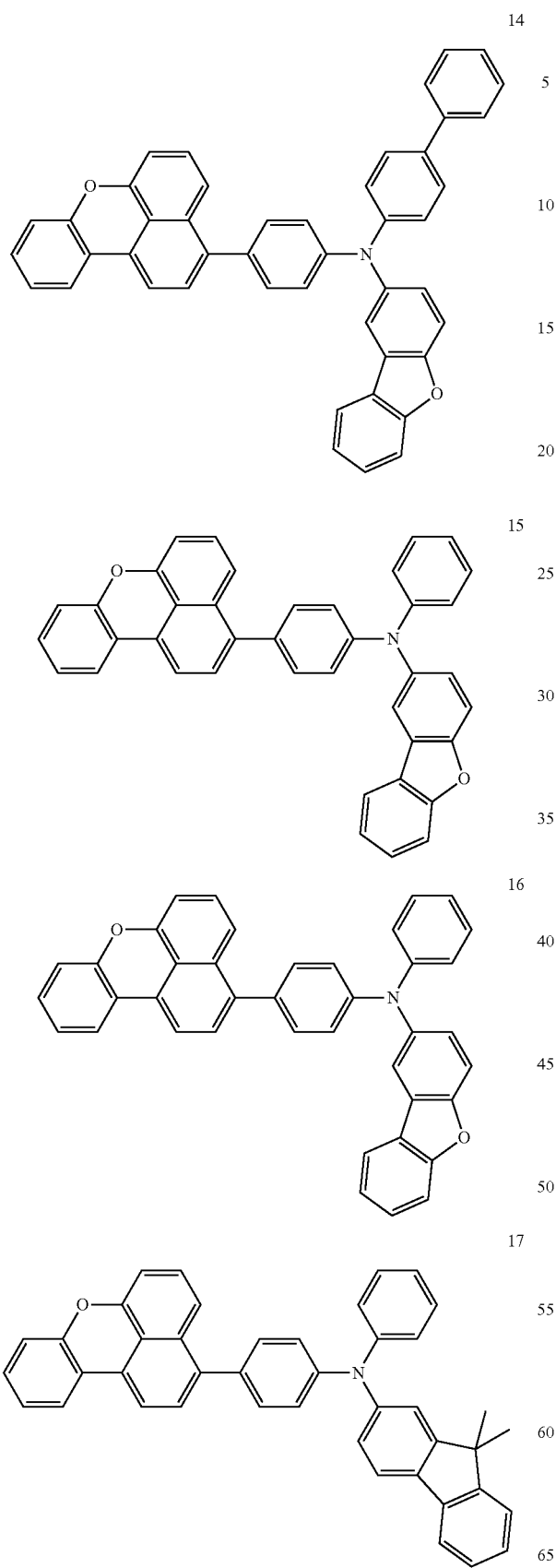
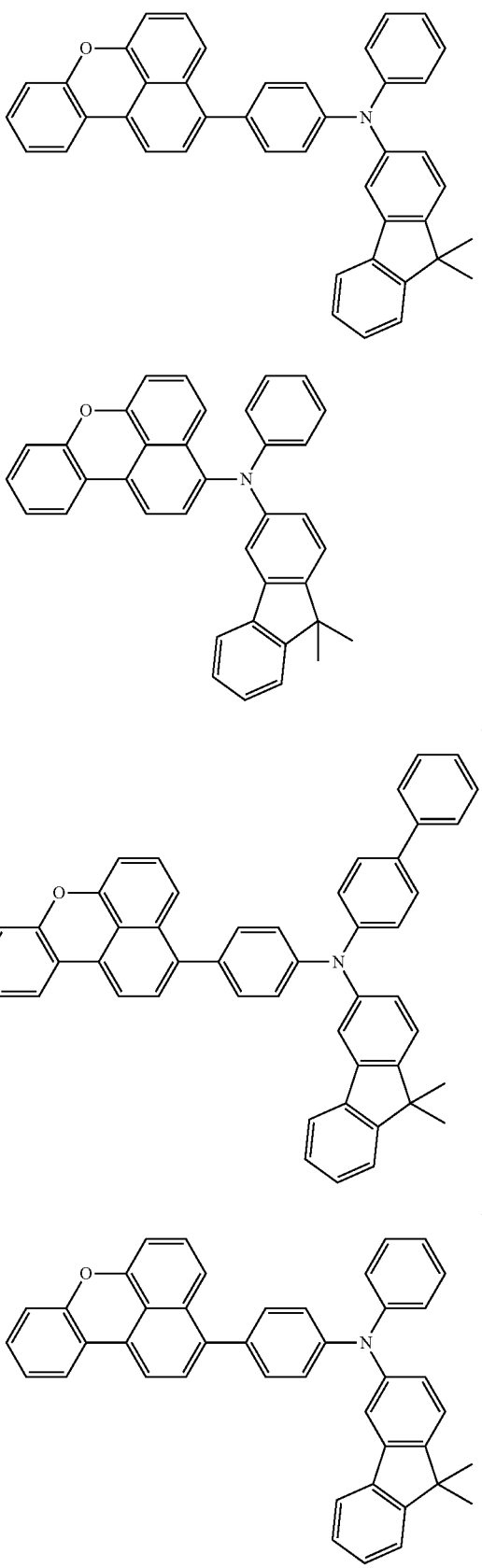

181
-continued
22
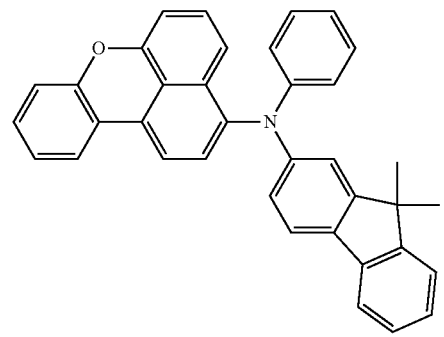
23
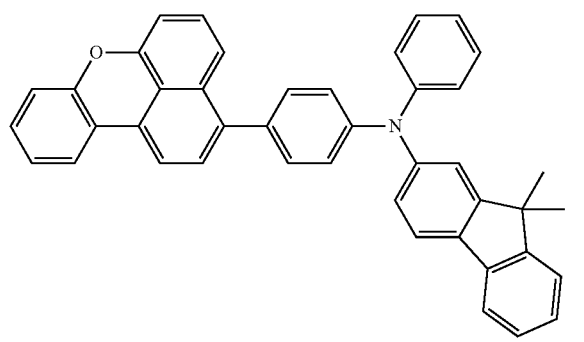
24
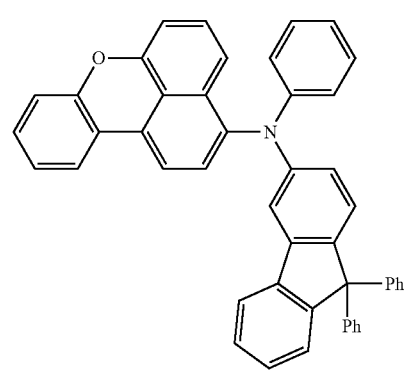
25
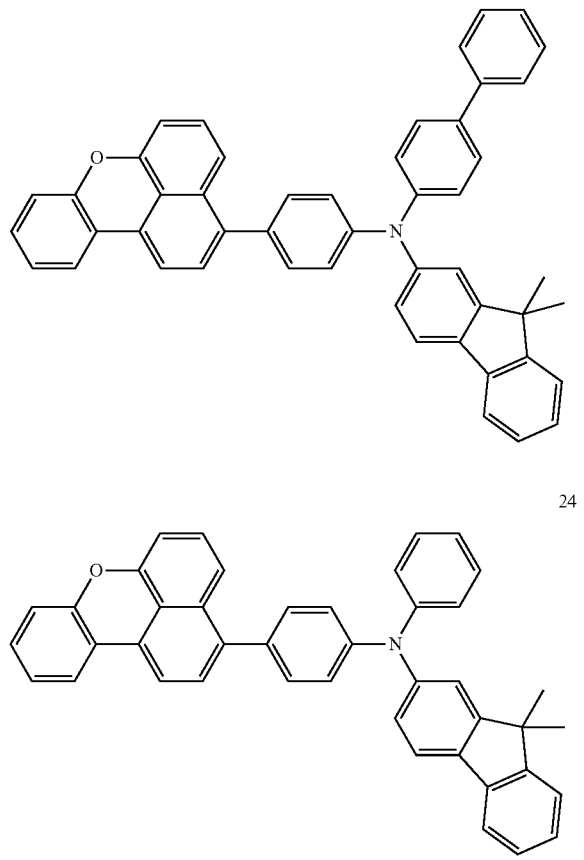
182
-continued
26
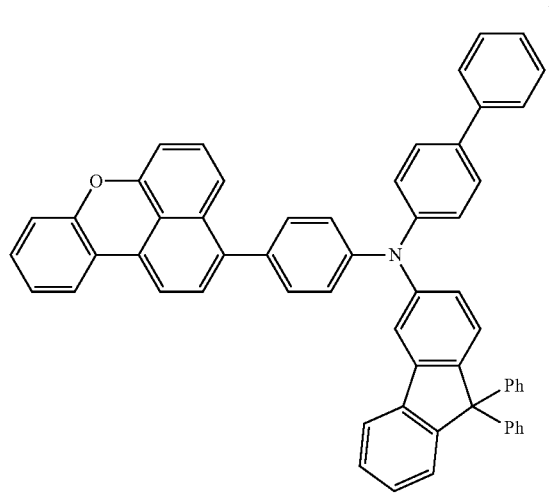
27
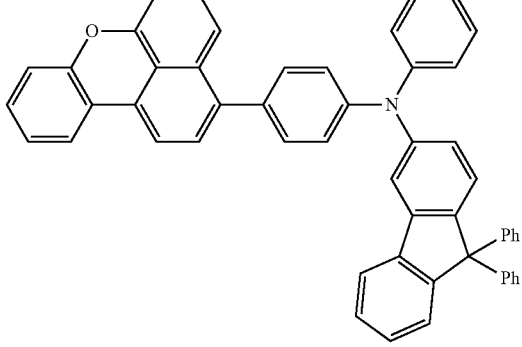
28
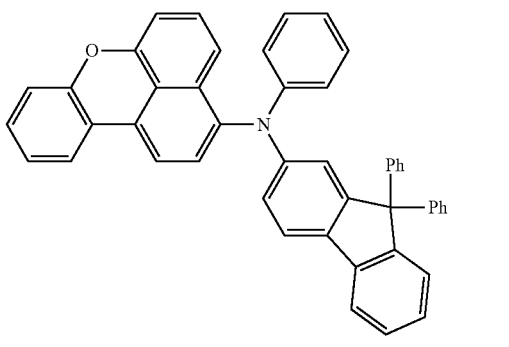

29
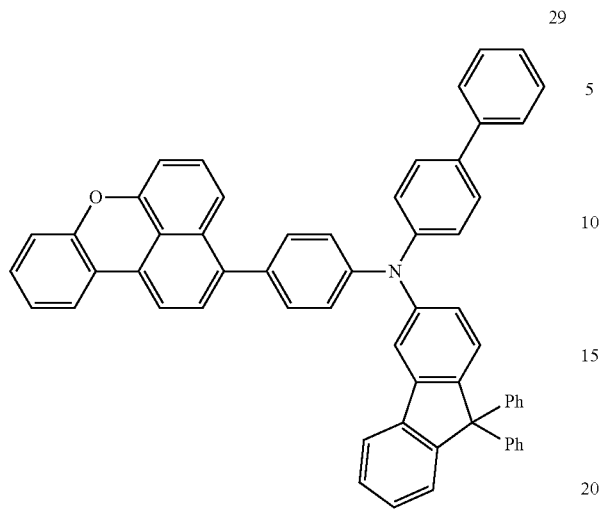
33
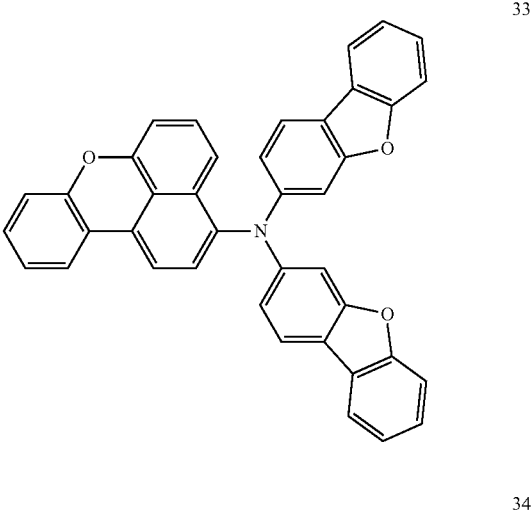
30
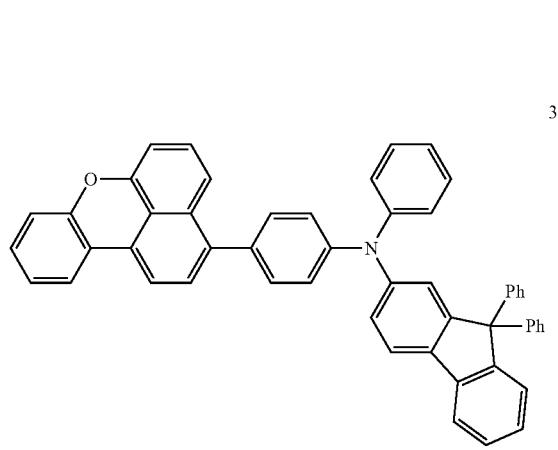
34
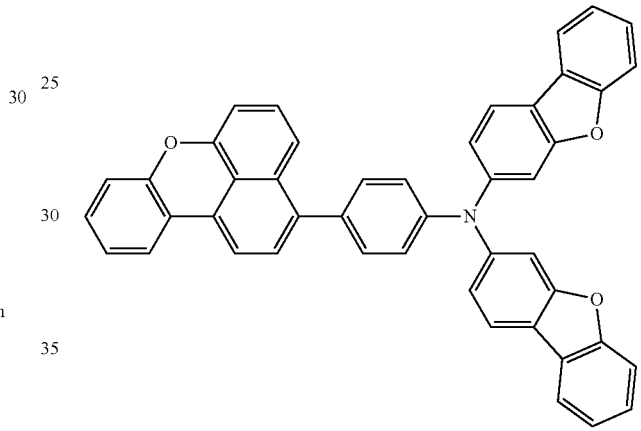
31
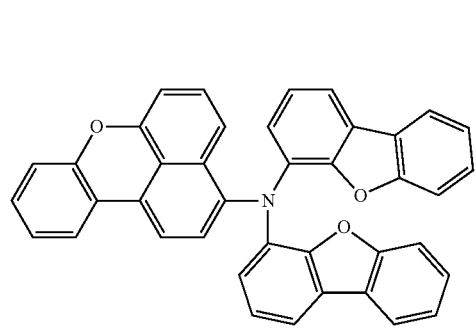
35
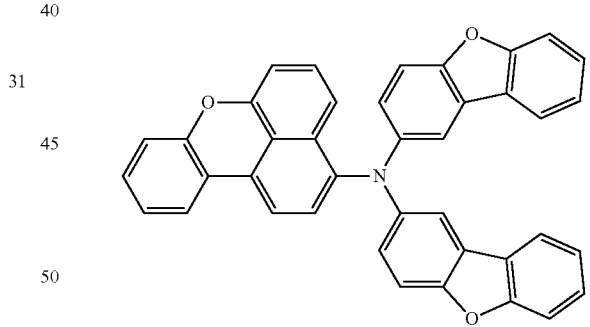
32
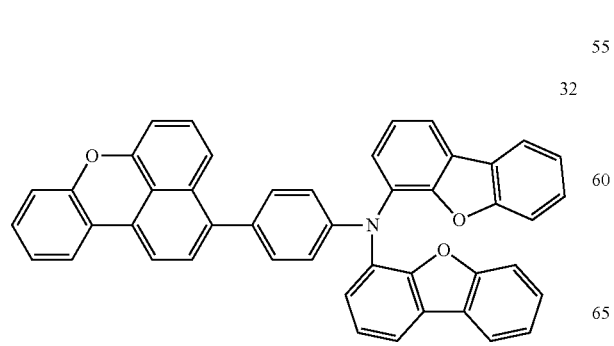
36
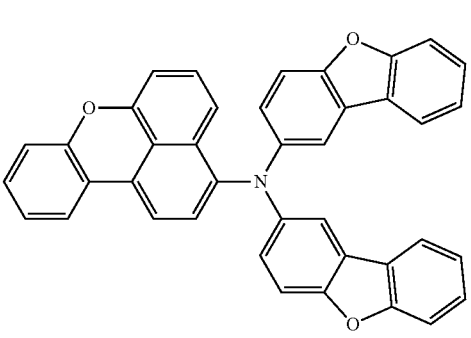

37
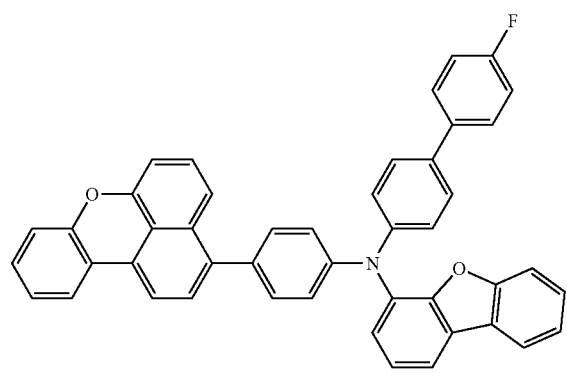
38
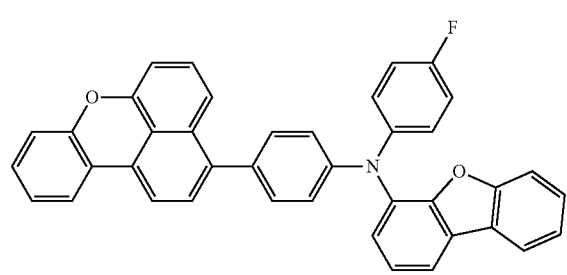
39
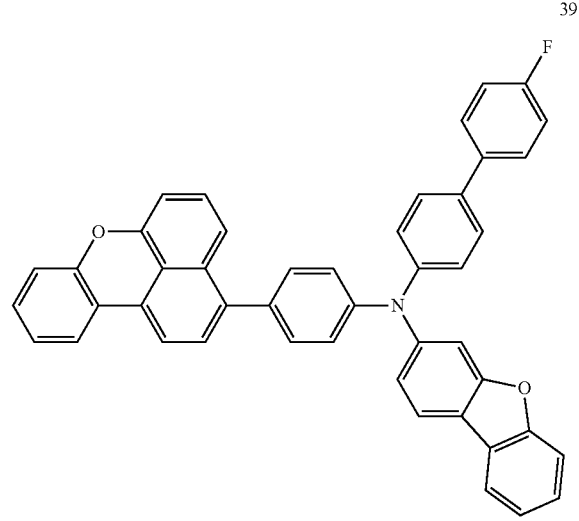
40
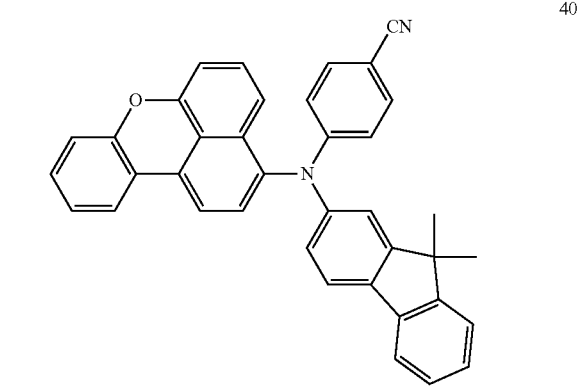
41
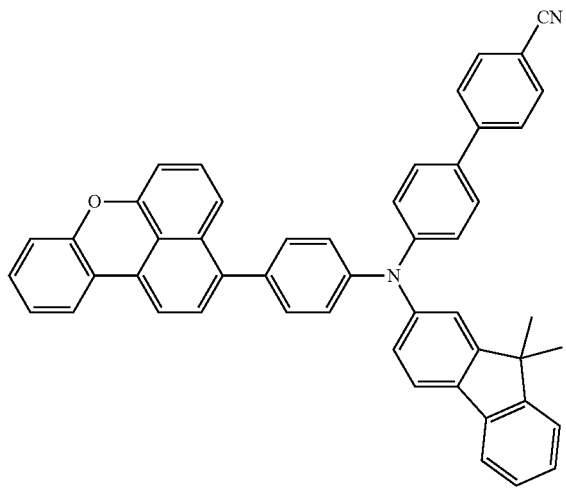
42
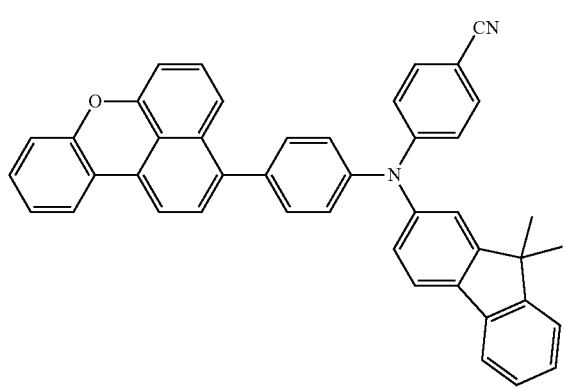
43
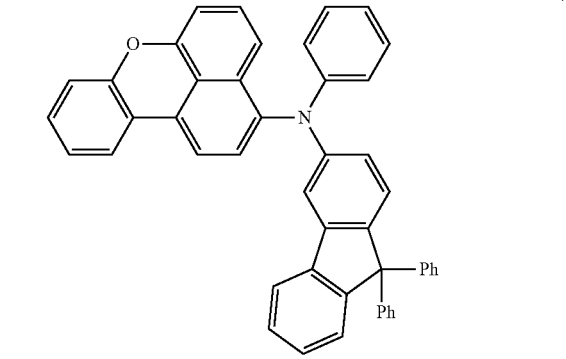
44
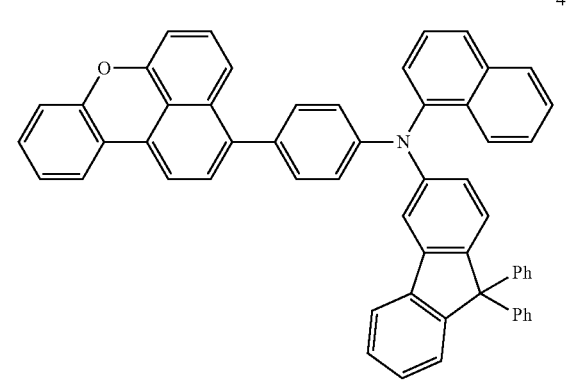

45
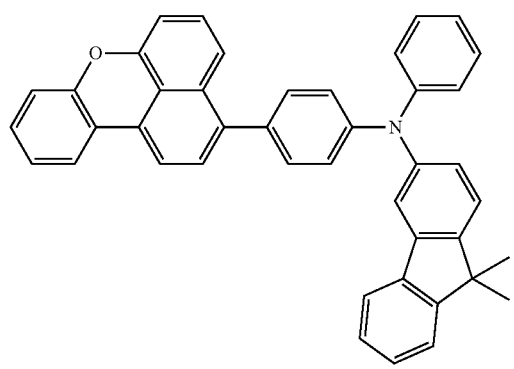
46
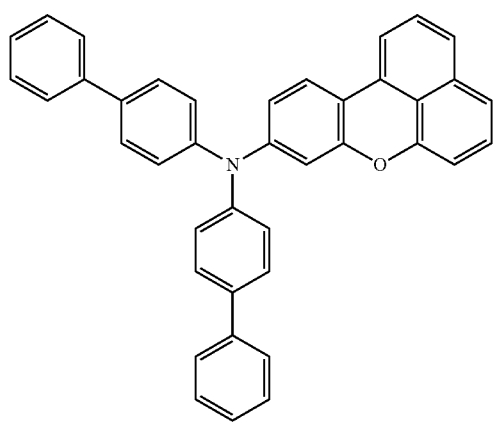
47
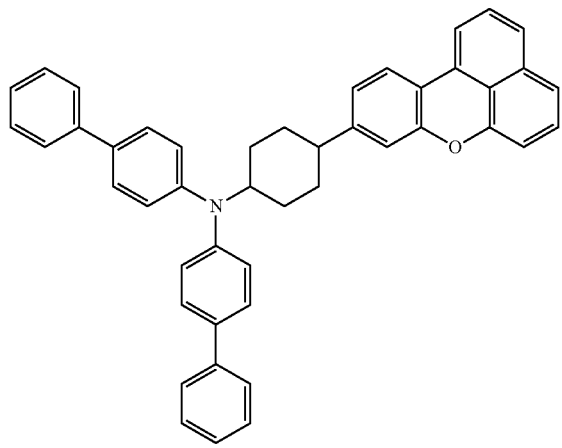
48
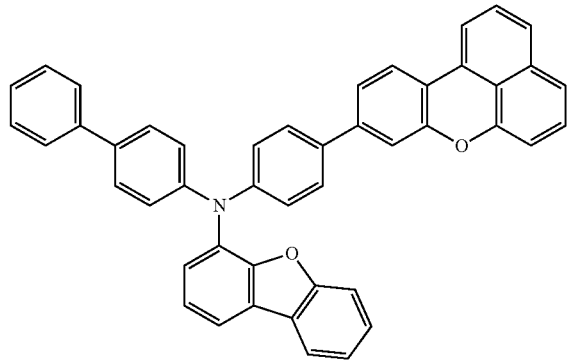
49
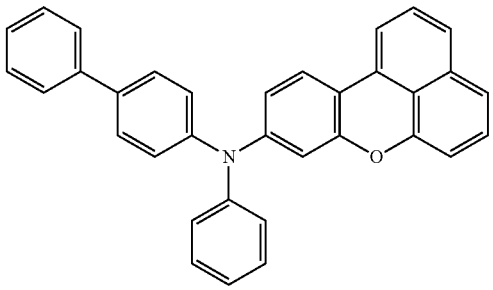
50
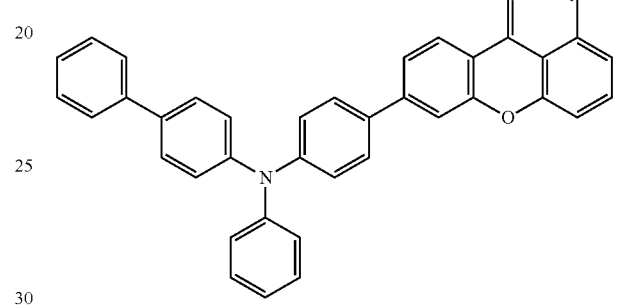
51
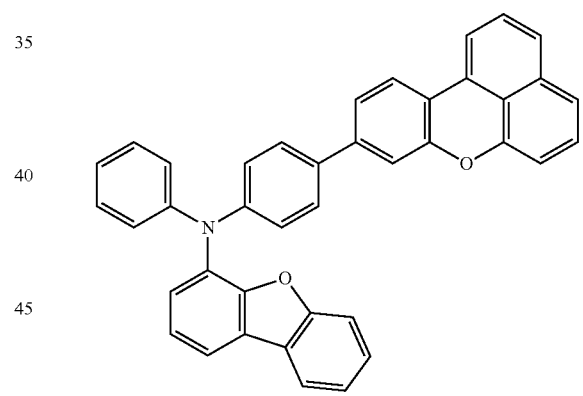
52
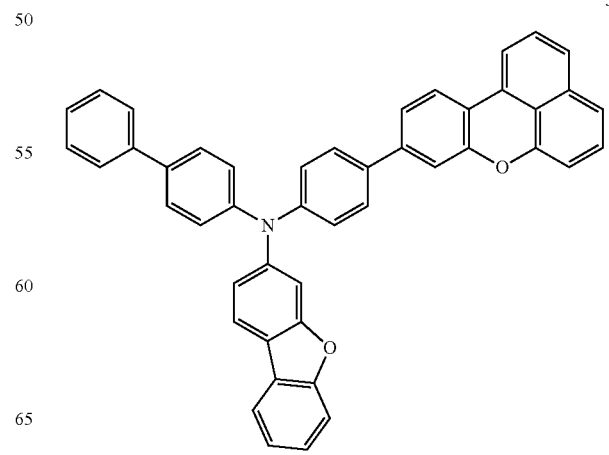

-continued
53
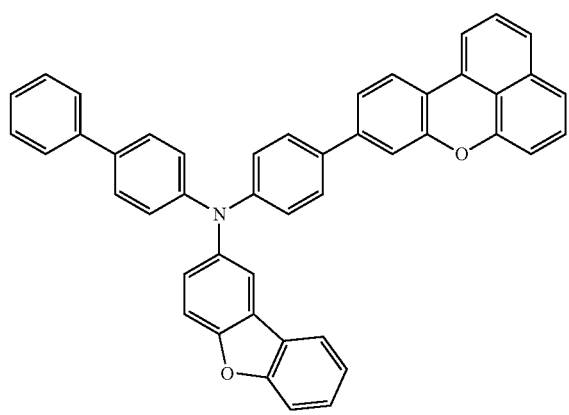
54
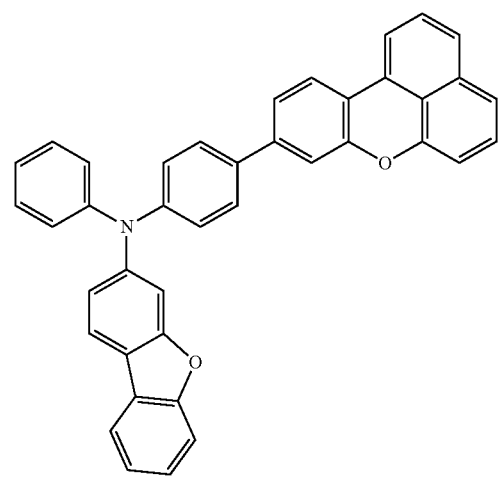
55
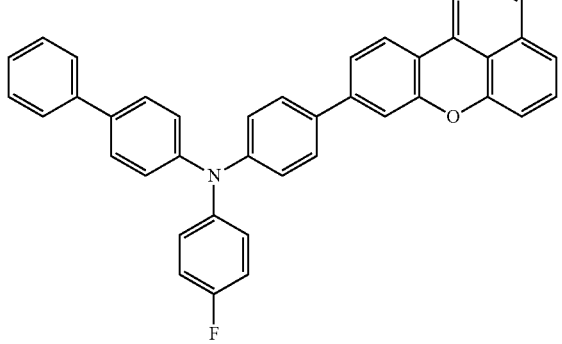
-continued
56
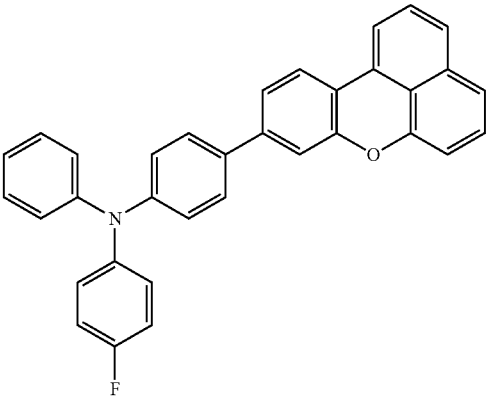
57
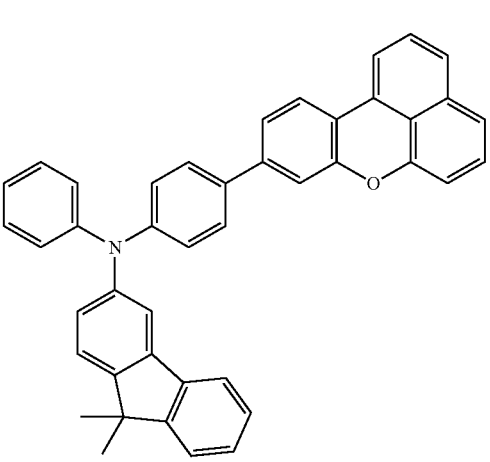
58
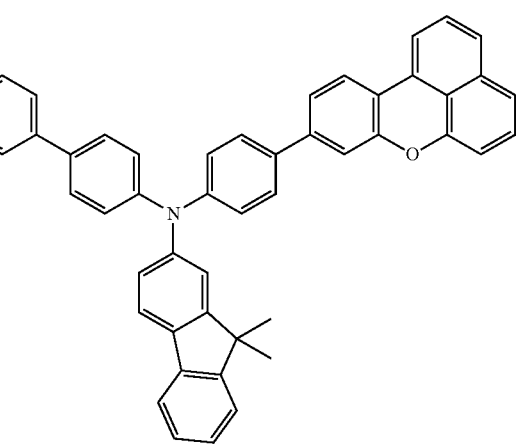

59
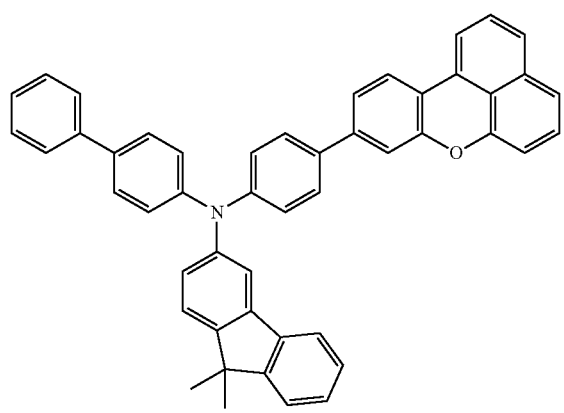
60
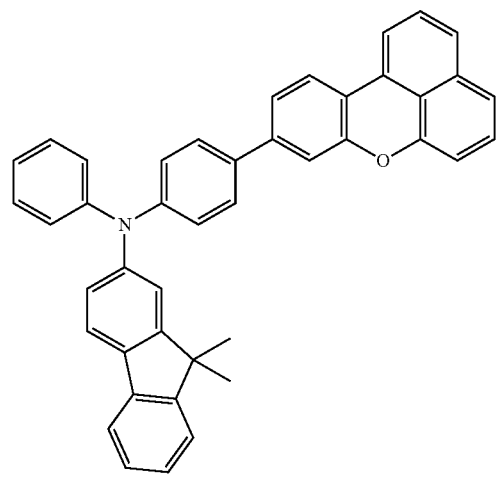
61
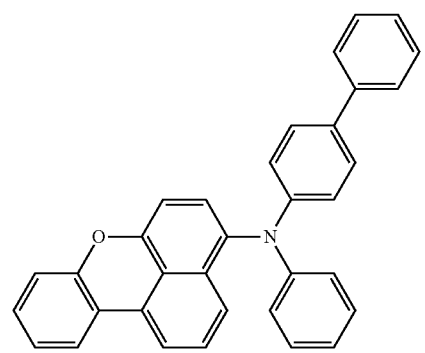
62
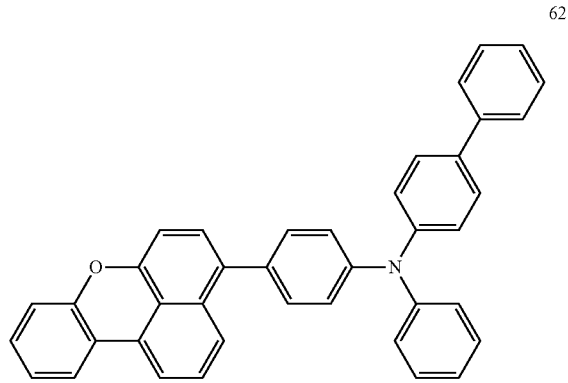
63
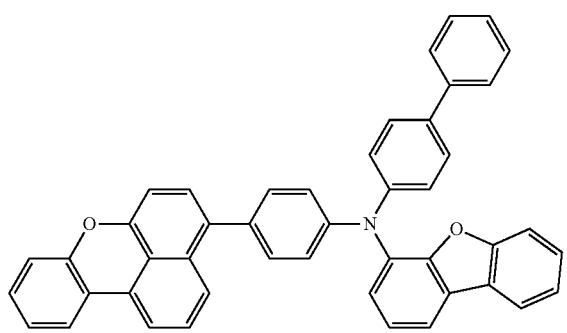
64
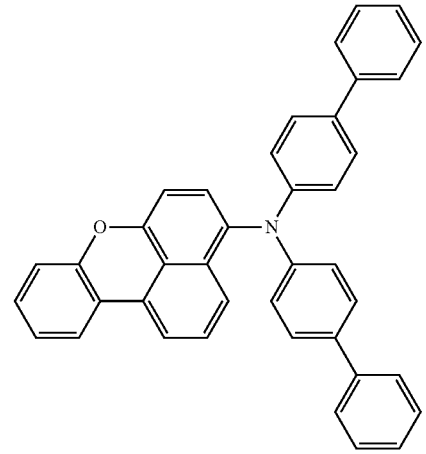
65
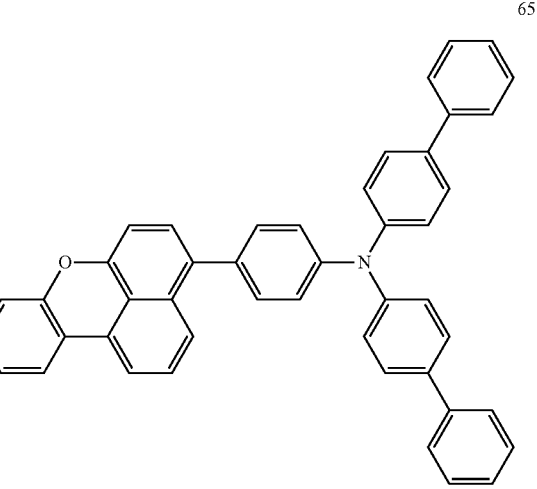

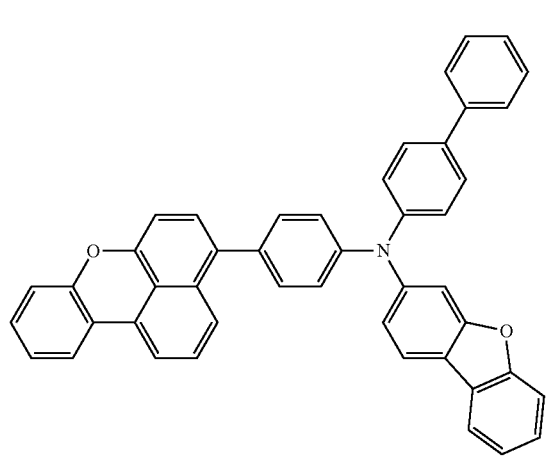
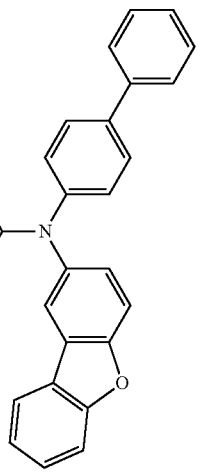
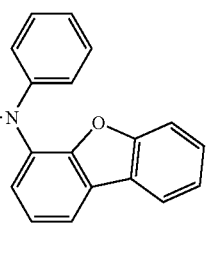
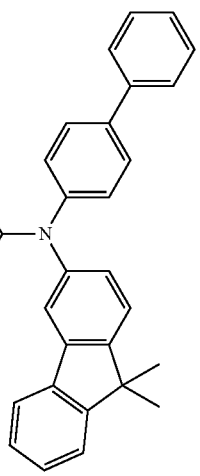

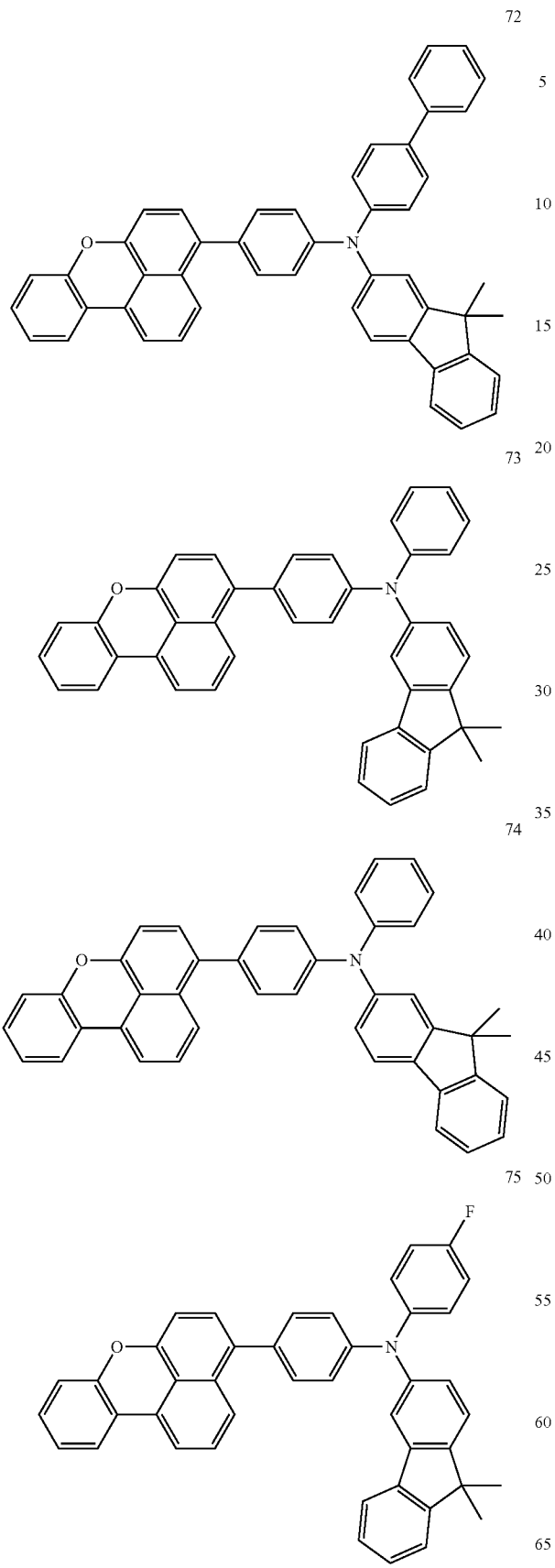
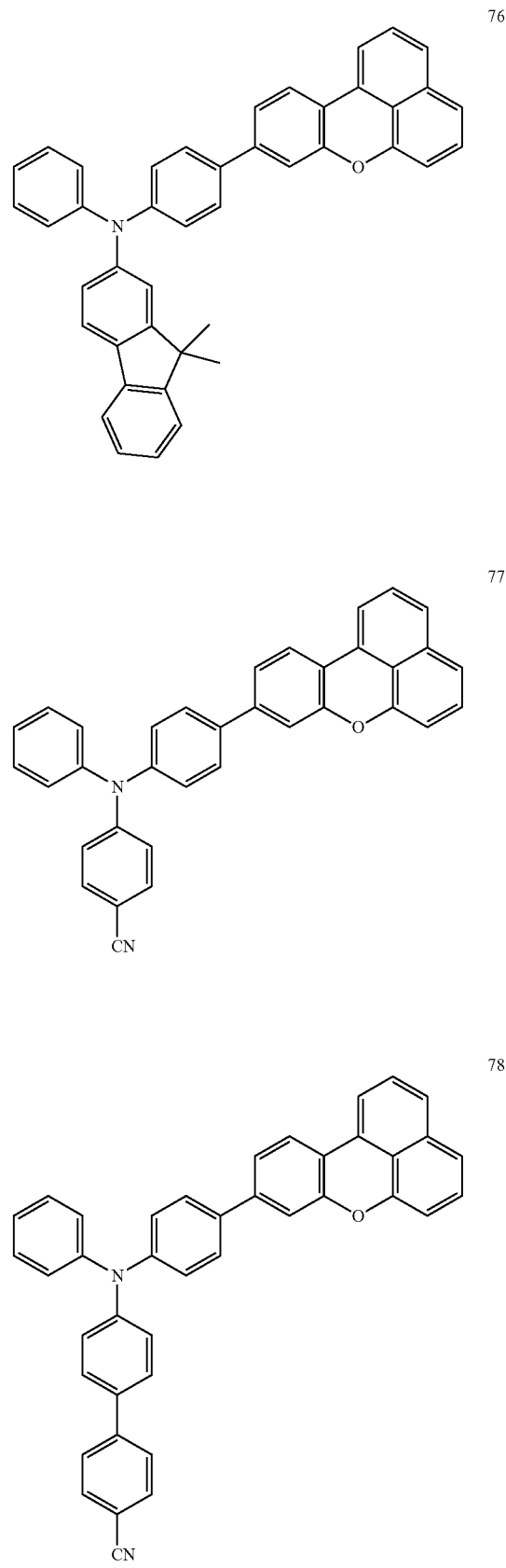

-continued
79
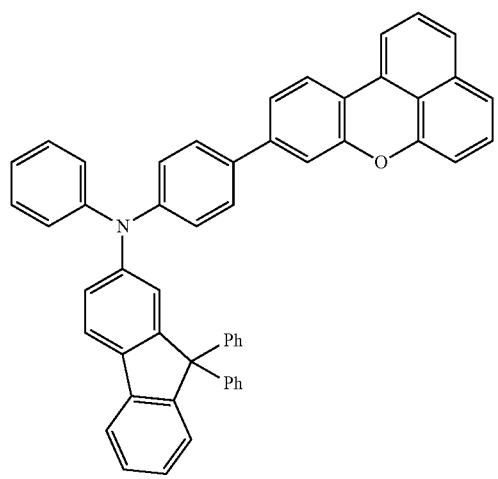
80
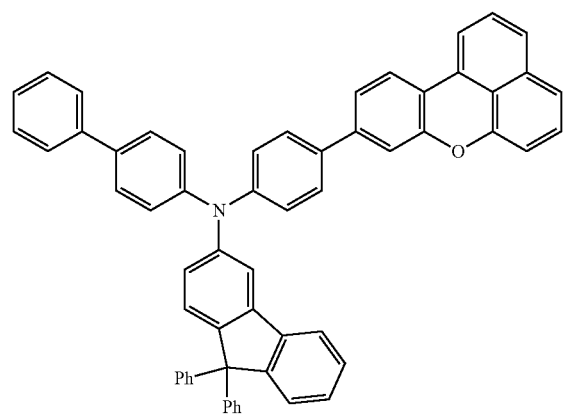
81
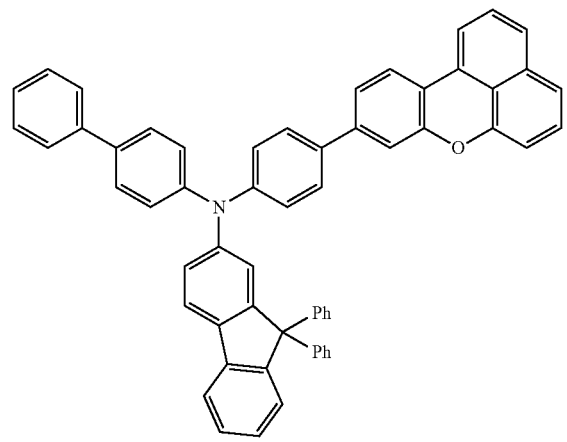
-continued
82
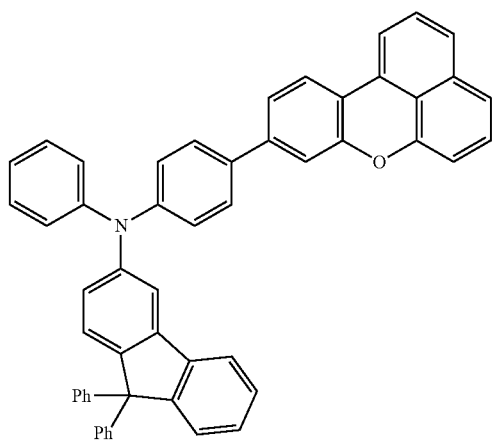
83
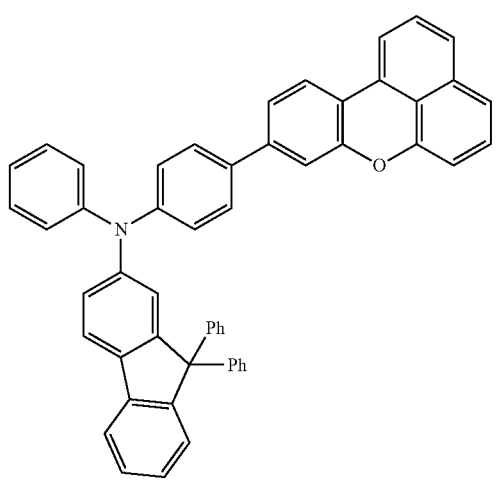
84
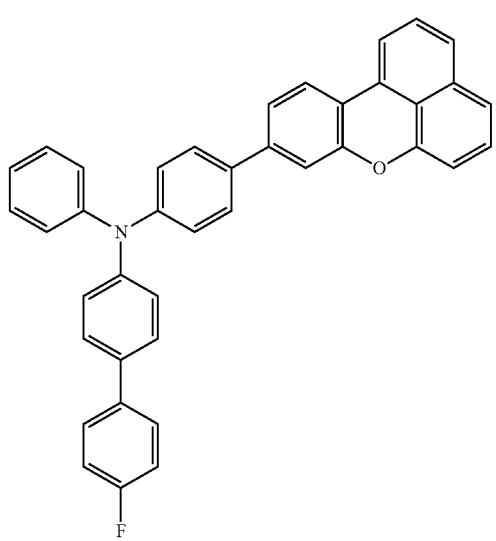

85
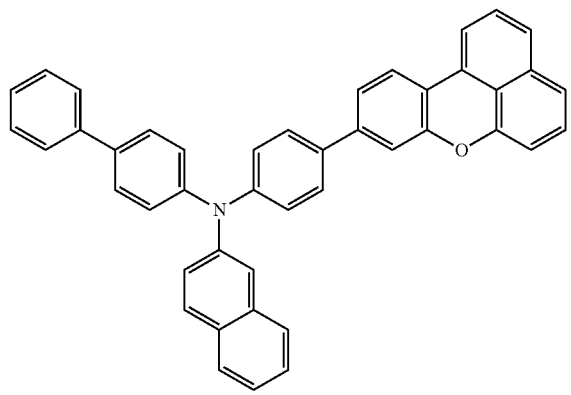
86
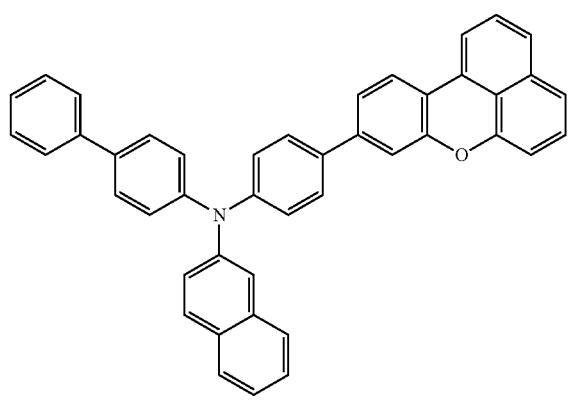
87
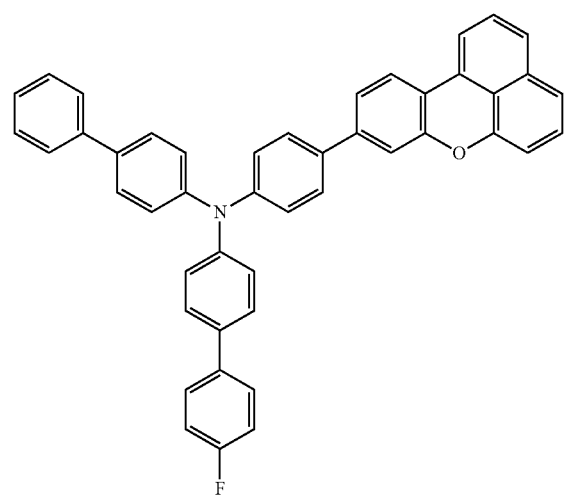
88
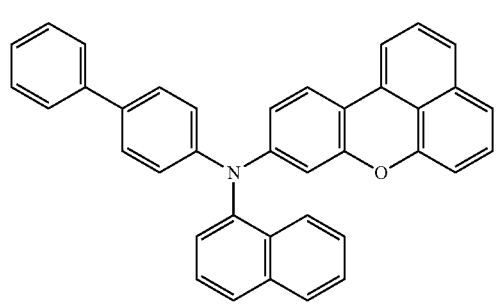
89
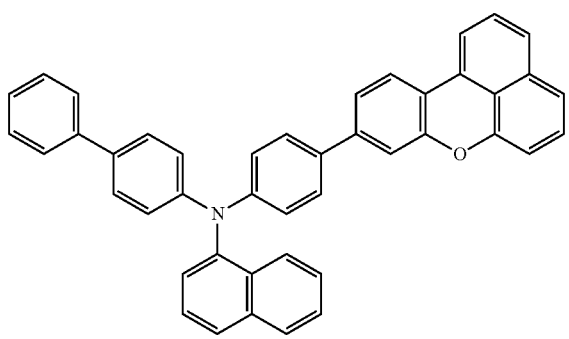
90
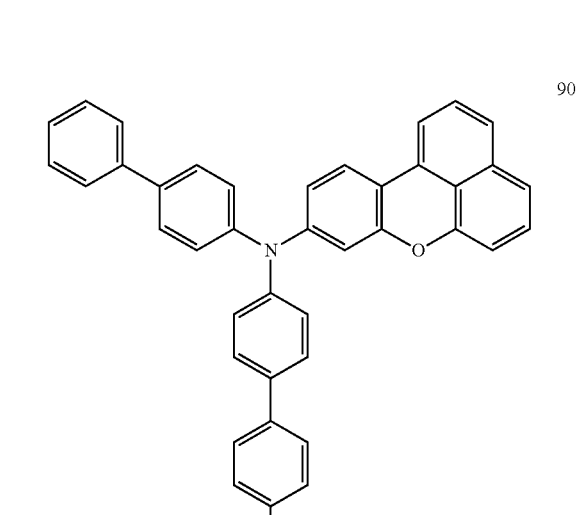
91
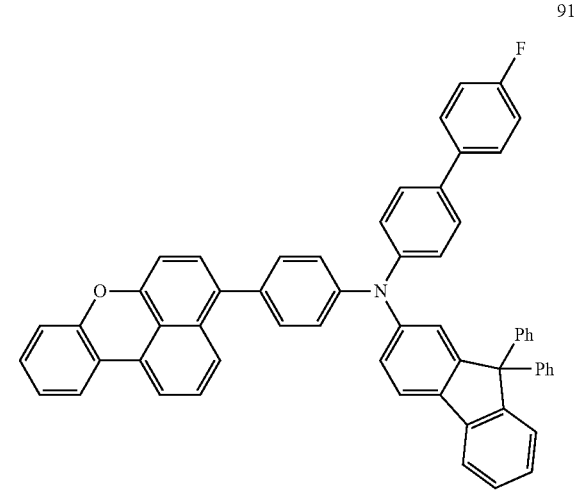

201
-continued
92
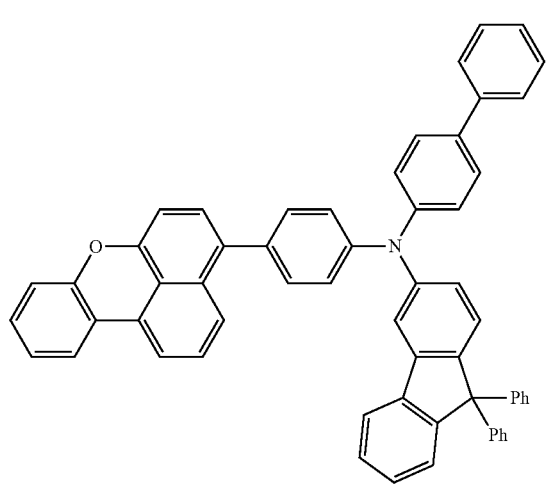
93
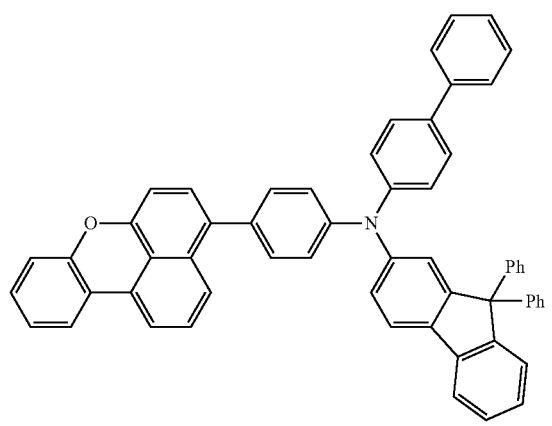
94
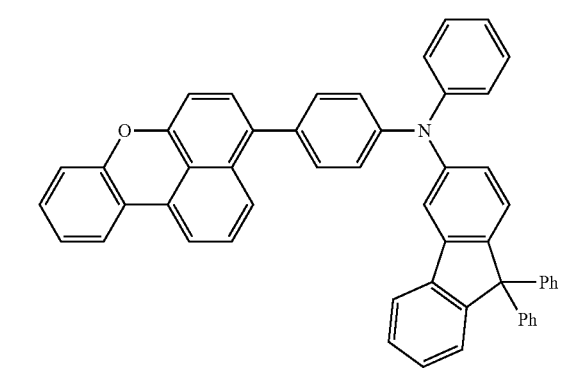
95
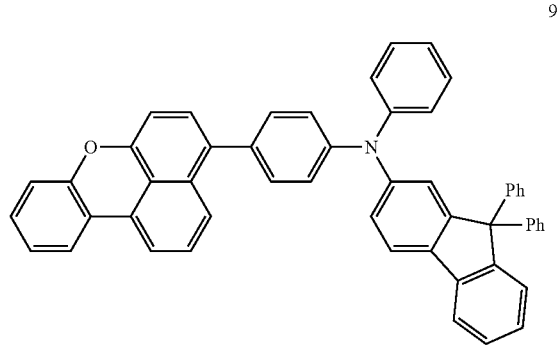
202
-continued
96
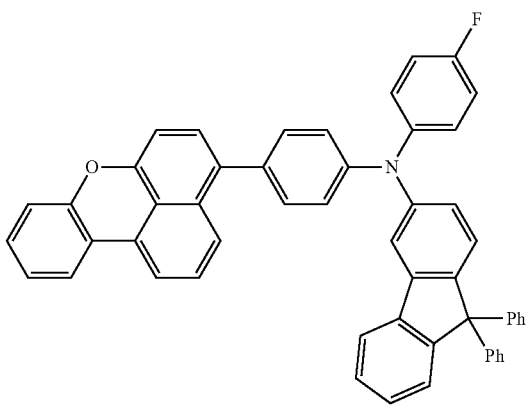
97
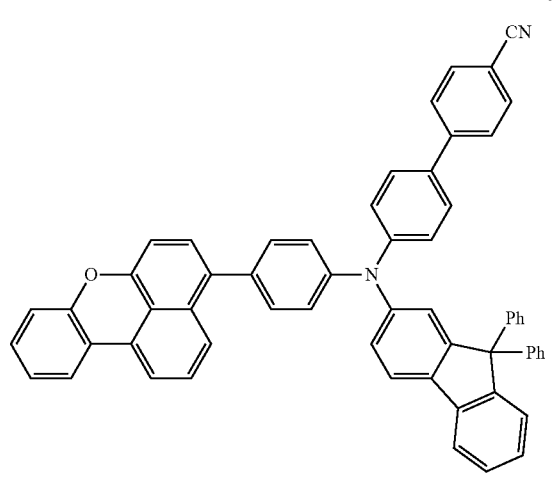
98
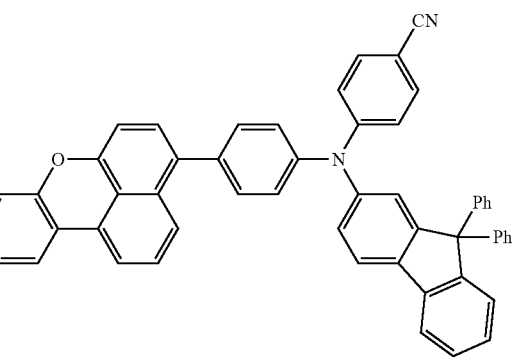
99
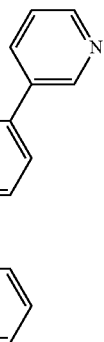

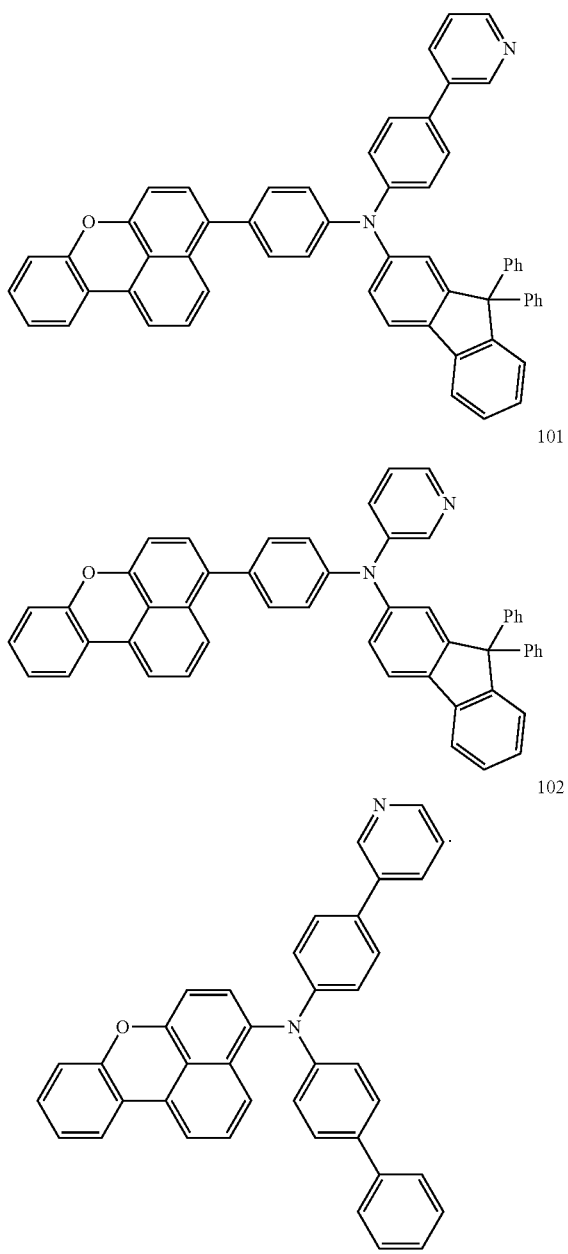

13. An organic light-emitting device, comprising:
a first electrode;
a second electrode facing the first electrode; and
an organic layer between the first electrode and the second electrode, the organic layer including an emission layer,
wherein the organic layer includes the condensed cyclic compound as claimed in claim 1.

14. The organic light-emitting device as claimed in claim 13, wherein:
the first electrode is an anode,
the second electrode is a cathode, and
the organic layer includes:
a hole transport region between the first electrode and the emission layer, the hole transport region including at least one selected from a hole injection layer, a hole transport layer, a buffer layer, and an electron blocking layer, and
an electron transport region between the emission layer and the second electrode, the electron transport region including a hole blocking layer, an electron transport layer, and an electron injection layer.

15. The organic light-emitting device as claimed in claim 14, wherein the hole transport region includes the condensed cyclic compound.

16. The organic light-emitting device as claimed in claim 15, wherein the hole transport region further includes a charge-generation material.

17. A condensed cyclic compound represented by one of the following Formulae 1-2(A), 1-2(B), 1-3(A), and 1-3(B):

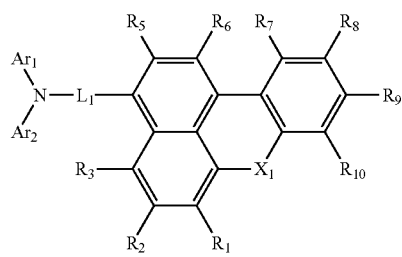

<Formula 1-2(A)>

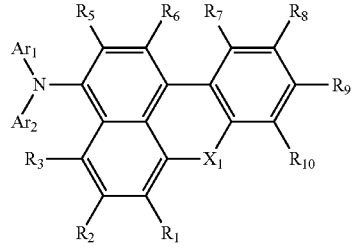

<Formula 1-2(B)>

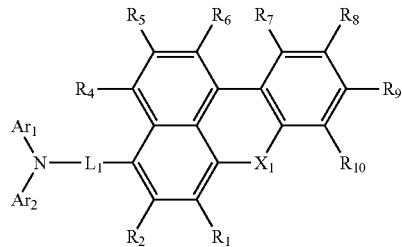

<Formula 1-3(A)>

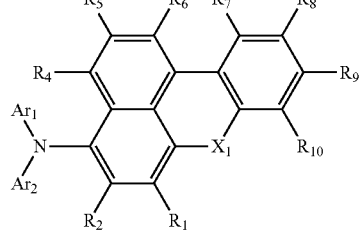

<Formula 1-3(B)> wherein, in Formulae 1-2(A), 1-2(B), 1-3(A), and 1-3(B):
$X_1$ is O,
$R_1$ to $R_{10}$ are each a hydrogen,
$L_1$ is a group represented by one of the following Formulae 4-1 to 4-29, and
$Ar_1$ and $Ar_2$ are each independently a group represented by one of the following Formulae 6-1 to 6-13 and 6-15 to 6-35,

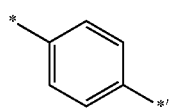
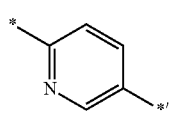
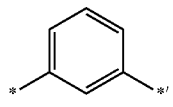
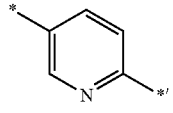
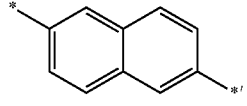
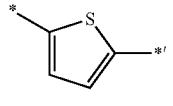
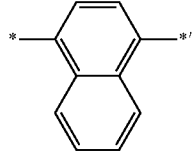
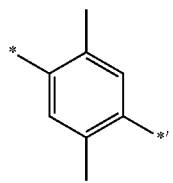
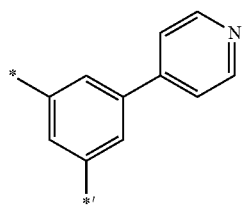
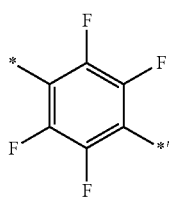
Formula 4-1
Formula 4-2
Formula 4-3
Formula 4-4
Formula 4-5
Formula 4-6
Formula 4-7
Formula 4-8
Formula 4-9
Formula 4-10
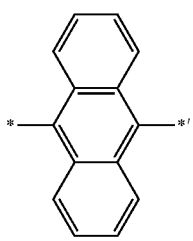
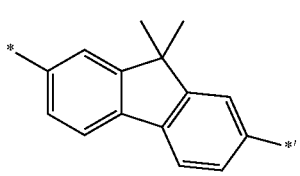
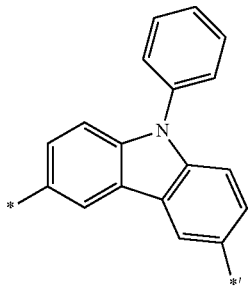
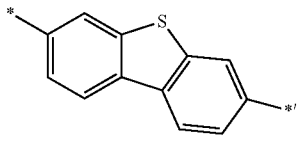
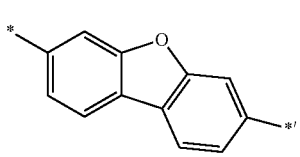
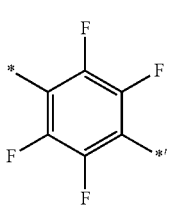
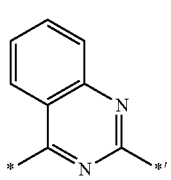
Formula 4-11
Formula 4-12
Formula 4-13
Formula 4-14
Formula 4-15
Formula 4-16
Formula 4-17
Formula 4-18

Formula 4-19
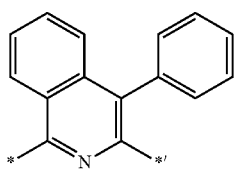
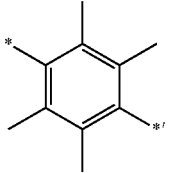
Formula 4-20
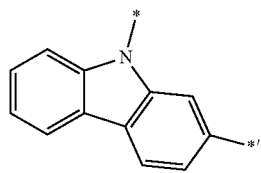
Formula 4-21
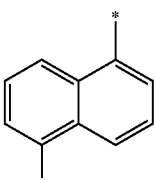
Formula 4-22
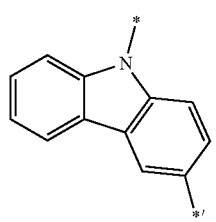
Formula 4-23
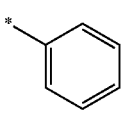
Formula 4-24
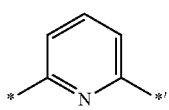
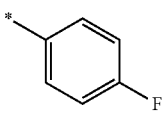
Formula 4-25
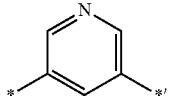
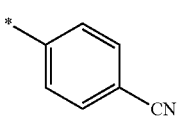
Formula 4-26
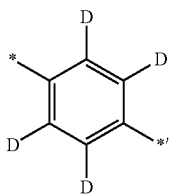
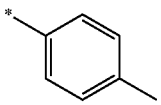
Formula 4-27
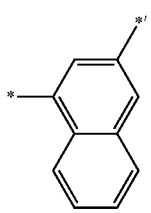
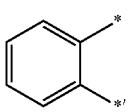
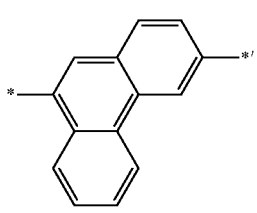
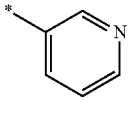
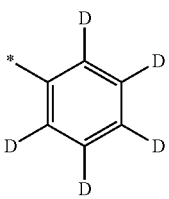
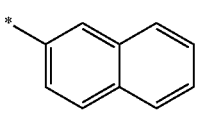
Formula 4-28
Formula 4-29
Formula 6-1
Formula 6-2
Formula 6-3
Formula 6-4
Formula 6-5
Formula 6-6
Formula 6-7
Formula 6-8
Formula 6-9

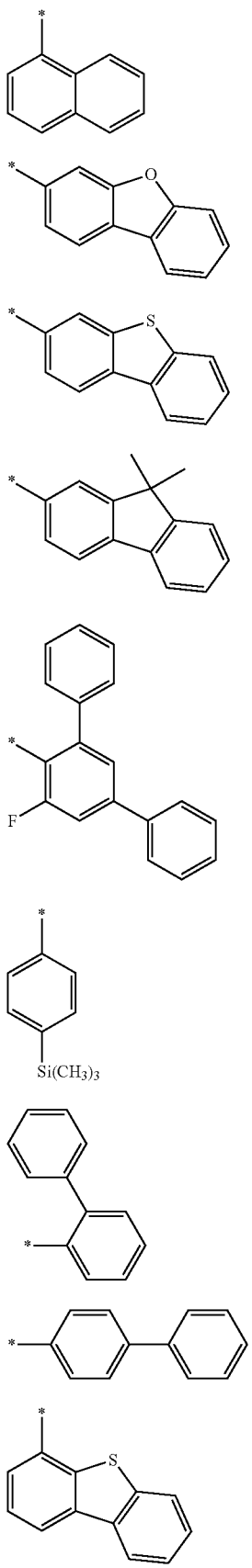
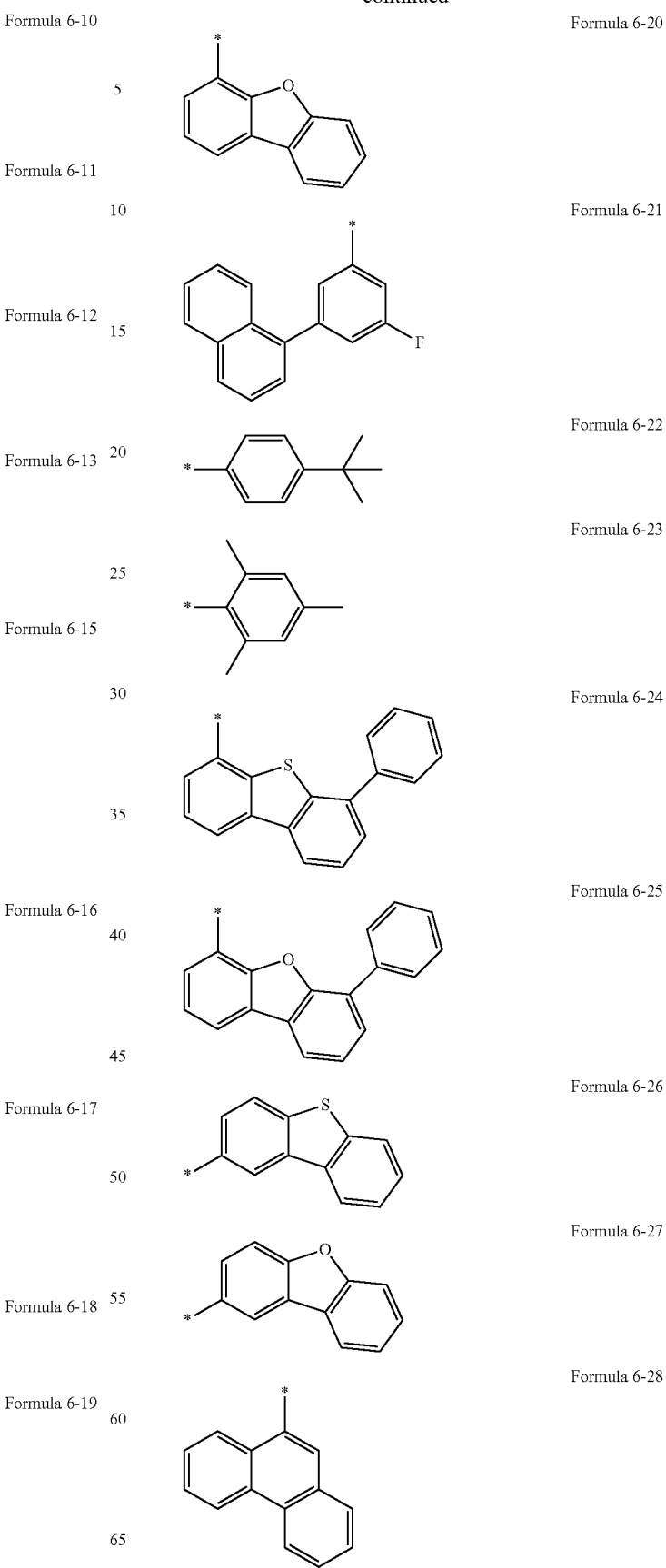

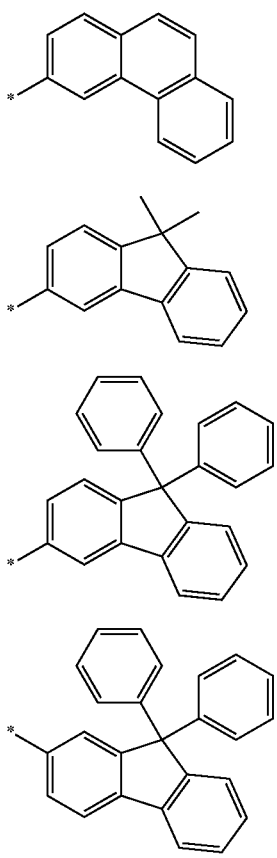
Formula 6-29
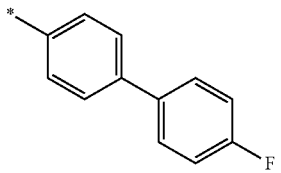
Formula 6-33
Formula 6-30
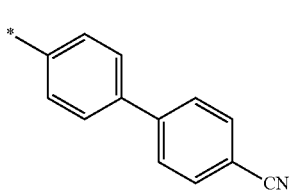
Formula 6-34
Formula 6-31
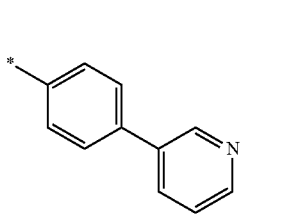
Formula 6-35
Formula 6-32
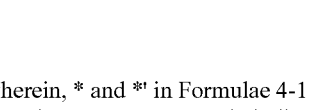
wherein, * and *' in Formulae 4-1 to 4-29 and 6-1 to 6-13 and 6-15 to 6-35 each indicate a binding site to a neighboring atom.
* * * * *